US012016687B2

(12) United States Patent
Vlasov et al.

(10) Patent No.: US 12,016,687 B2
(45) Date of Patent: Jun. 25, 2024

(54) IMPLANTABLE PROBES AND METHODS OF FABRICATION

(71) Applicant: The Board of Trustees of the University of Illinois, Urbana, IL (US)

(72) Inventors: Yurii Vlasov, Urbana, IL (US); Yan Zhang, Urbana, IL (US); Christopher Kenji Brenden, Urbana, IL (US); Prasoon Kumar Jha, Urbana, IL (US); Yifei Yan, Urbana, IL (US); Sungho Kim, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 116 days.

(21) Appl. No.: 17/356,062

(22) Filed: Jun. 23, 2021

(65) Prior Publication Data

US 2021/0393175 A1 Dec. 23, 2021

Related U.S. Application Data

(60) Provisional application No. 63/042,856, filed on Jun. 23, 2020.

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/0075* (2013.01); *A61B 5/14503* (2013.01);
(Continued)

(58) Field of Classification Search
CPC ............. B01L 3/5027; B01L 3/502715; A61B 10/0045; A61B 5/14503; A61B 2010/007;
(Continued)

(56) References Cited

U.S. PATENT DOCUMENTS 6,464,892 B2 10/2002 Moon et al.
6,768,107 B2 6/2004 Schultz et al.
(Continued)

FOREIGN PATENT DOCUMENTS

WO WO 2000/050880 A2 8/2000
WO WO 2007/081386 A2 7/2007
WO WO 2018/202994 A1 11/2018

OTHER PUBLICATIONS

Ngernsutivorakul, T. (2018). Microfabricated Sampling Probes for Monitoring Brain Chemistry at High Spatial and Temporal Resolution (Doctoral dissertation). (Year: 2018).*
(Continued)

*Primary Examiner* — Yi-Shan Yang
*Assistant Examiner* — Kyle W. Kretzer
(74) *Attorney, Agent, or Firm* — Leydig, Voit & Mayer, Ltd.

(57) ABSTRACT

Provided are implantable probes for analyzing biological fluids and related methods of using and making. The probe is formed with an integrated on-chip probe body that provides for collection and storage of analyte from biological fluid and facilitates subsequent analysis, including by a mass spectrometer (MS). The analysis has high spatial accuracy as the probe tip that collects biological fluid sample is small, including less than 100 μm with an opening less than 10 μm. Temporal information can be obtained by storing the analyte from the biological fluid as a train of droplets separated by an immiscible fluid. The probe body can be electrically energized to facilitate sample ionization and transfer to a MS analysis device. In this manner, the integrated on-chip probe body facilitates analyte collection, storage and subsequent analysis within a single probe body material, including a doped silicon material.

22 Claims, 38 Drawing Sheets

(51) Int. Cl.
*A61B 10/00* (2006.01)
*B01L 3/00* (2006.01)

(52) U.S. Cl.
CPC ...... *A61B 5/14507* (2013.01); *A61B 10/0045* (2013.01); *B01L 3/502715* (2013.01)

(58) Field of Classification Search
CPC .............. A61B 5/14546; A61B 5/0075; A61B 5/14507
See application file for complete search history.

(56) References Cited

U.S. PATENT DOCUMENTS

| | | | |
|---|---|---|---|
| 6,904,309 | B2 | 6/2005 | Derendorf et al. |
| 7,105,810 | B2 | 9/2006 | Kameoka et al. |
| 7,608,064 | B2 | 10/2009 | Putz |
| 8,431,888 | B2 | 4/2013 | Kennedy et al. |
| 8,530,832 | B2 | 9/2013 | Mordehai et al. |
| 8,703,537 | B2 | 4/2014 | Pellinen et al. |
| 9,490,111 | B2 | 11/2016 | Abell et al. |
| 9,957,554 | B1 | 5/2018 | Wu et al. |
| 11,014,047 | B2 | 5/2021 | Kennedy et al. |
| 2006/0193748 | A1 | 8/2006 | Tai et al. |
| 2007/0128078 | A1 | 6/2007 | Sarrut et al. |
| 2011/0084014 | A1 | 4/2011 | Chen et al. |
| 2014/0011226 | A1* | 1/2014 | Bernick ............ C12M 47/06 435/283.1 |
| 2017/0065764 | A1* | 3/2017 | Cho ..................... A61M 5/158 |
| 2018/0272287 | A1* | 9/2018 | Kennedy ............. C25D 11/045 |
| 2018/0355350 | A1 | 12/2018 | Link et al. |

OTHER PUBLICATIONS

Aris, Rutherford. "On the dispersion of a solute in a fluid flowing through a tube." Proceedings of the Royal Society of London. Series A. Mathematical and Physical Sciences 235.1200 (1956): 67-77.
Bucher et al. "Electrochemical Analysis of Neurotransmitters" Annual review of analytical chemistry 2015, 8, 239-261.
Croushore et al. "Microfluidic systems for studying neurotransmitters and neurotransmission." Lab on a Chip 13.9 (2013):1666-1676.
Cubaud, Thomas, and Thomas G. Mason. "Capillary threads and viscous droplets in square microchannels." Physics of Fluids 20.5 (2008): 053302.
De Menech, M., et al. "Transition from squeezing to dripping in a microfluidic T-shaped junction." Journal of fluid mechanics 595 (2008): 141-161.
Ferri et al. "Elastic nanomembrane metrology at fluid-fluid interfaces using axisymmetric drop shape analysis with anisotropic surface tensions: deviations from Young-Laplace equation." Soft Matter 8.40 (2012): 10352-10359.
Garstecki et al. "Formation of droplets and bubbles in a microfluidic T-junction—scaling and mechanism of break-up." Lab on a Chip 6.3 (2006):437-446.
Kennedy, Robert T. "Emerging trends in in vivo neurochemical monitoring by microdialysis" Current opinion in chemical biology 2013, 17, 860-867.
Nandi et al. "Recent trends in microdialysis sampling integrated with conventional and microanalytic systems for monitoring biological events: A review" Anal Chim Acta 2009, 651, 1-14.
Ngernsutivorakul et al. "In Vivo Chemical Monitoring at High Spatiotemporal Resolution Using Microfabricated Sampling Probes and Droplet-Based Microfluidics Coupled to Mass Spectrometry" Analytical chemistry 2018, 90, 10943-10950.
Petit-Pierre, et al. "In vivo neurochemical measurements in cerebral tissues using a droplet-based monitoring system" Nat. Commun. 8, 1239, 2017.
Robinson et al. "Detecting Subsecond Dopamine Release with Fast-Scan Cyclic Voltammetry in Vivo" Clinical chemistry 2003, 49(10), 1763-1773.
Shazia et al. "Simulations of microfluidic droplet formation using the two-phase level set method." Chemical Engineering Science 66.20 (2011): 4733-4741.
Slaney et al. "Push-Pull Perfusion Sampling with Segmented Flow for High Temporal and Spatial Resolution in Vivo Chemical Monitoring" Analytical chemistry 2011, 83, 5207-5213.
Song et al. "Mass Spectrometry 'Sensor' for in Vivo Acetylcholine Monitoring" Analytical chemistry 2012, 84, 4659-4664.
Thorsen et al. "Dynamic Pattern Formation in a Vesicle-Generating Microfluidic Device" Phys. Rev. Lett., 2001, 86, 4163.
Utada et al. "Dripping to jetting transitions in coflowing liquid streams." Physical review letters 99, No. 9 (2007): 094502.
Van Steijn et al. "Predictive model for the size of bubbles and droplets created in microfluidic T-junctions." Lab on a Chip 10.19 (2010): 2513-2518.
Zhang et al. "Droplet-assisted phase separation by integrated silicon electrospray nano-emitter for neurochemical sensing." Lab Chip (2021). 22: pp. 40-46.
Zhang et al. "Picoliter Droplet Generation for Fast Monitoring the Brain Chemistry with Scaled Silicon Nanodyalisis Probe." In Jun. 23-27, 2019 20th International Conference on Solid-State Sensors, Actuators and Microsystems and Eurosensors XXXIII, Transducers 2019 and Eurosensors XXXIII pp. 209-212.
Zhu et al. "Passive and active droplet generation with microfluidics: a review." Lab on a Chip 17.1 (2017): 34-75.

* cited by examiner

IMPLANTABLE PROBES AND METHODS OF FABRICATION

CROSS-REFERENCE TO RELATED APPLICATIONS

This application claims the benefit of U.S. Provisional Application No. 63/042,856, filed on Jun. 23, 2020, which is incorporated by reference herein in its entirety to the extent not inconsistent herewith.

STATEMENT REGARDING FEDERALLY SPONSORED RESEARCH OR DEVELOPMENT

This invention was made with government support under Award Number NS107677 awarded by the National Institutes of Health (NIH). The government has certain rights in the invention.

BACKGROUND OF INVENTION

Brain chemistry is important for understanding brain function. Brain chemistry, however, is challenging to measure in vivo. Most neuromodulators are present at relatively low concentrations, such as less than about nM. This means that measurements of the neuromodulators require high sensitivity and selectivity. Furthermore, it is often important to measure the neuromodulators temporally. Conventional methods for in vivo measurement include microdialysis and low-flow push-pull perfusion.

Those methods, however, suffer from severe limitations. For example, they do not have high temporal resolution. When a pipette draws up brain chemicals, shear-induced dispersion and diffusion causes significant smearing across the flow direction, which disrupts the concentration at a specific time. That problem can be addressed by using a separate oil droplet generator to periodically introduce oil into the pipette sampling channel during sampling, to isolate each specific sample and preserve temporal resolution. Issues, however, remain, including: (1) there is still diffusion within the channel between droplet generator and the pipette sampling; and (2) obtaining high recovery rates with conventional methods requires a low flow rate that inherently degrades temporal resolution.

Additional problems relate to sample analysis after the biological fluid is collected. The conventional methods require bulky peripheral devices which makes implantation risky and impractical. The problematic peripherals include: (1) droplet generators to generate oil plugs; and (2) electrospray ionization emitters to transfer the sample for Mass Spectrometry (MS) analysis. This increases the cost and complexity of analysis and impacts channel size, with larger capillaries required than in the pipette probe. Such mismatched size can result in intermixing and sample loss.

There is a need in the art for implantable devices having the ability to reliably collect, store and facilitate analysis of analytes within the fluid biological sample, including in a manner that maintains temporal information. Provided herein are devices, and related methods of making and using, that address this need by integrating the various required components in an on-chip configuration having a small form factor suitable for implantation.

SUMMARY OF THE INVENTION

Provided herein are probes having integrated functionality for biological fluid sampling and storage, transfer, and interfacing with a high-sensitivity analyzer, and integrated in a manner that implantation into biological systems is possible with minimal tissue disruption and adverse biological events. In this manner, analytes in a biological fluid can be collected in vivo and over a time course, with high-resolution and sensitivity, both in a spatial sense (e.g., precise control over where the sample is obtained) and temporal (how the sample may change over time, including analytes within the sample). Deploying an array of any of the devices provided herein, facilitates mapping of biological sample characteristics, such as a spatial map of analyte concentration that can temporally vary. The solution to providing multiple functionality corresponding to each of sampling, storage and emission (for subsequent analysis) in a small package suitable for in-vivo implantation in a living subject, such as a human, animal, plant or other living material where probing is desired organism, is achieved by forming the probe from a unitary material. This avoids a need for separate add-on components that otherwise complicate the device, increases fragility and handling difficulty, and/or makes the device overly bulky and difficult for in-vivo use or accessing of a fluid sample. The devices and methods provided herein are, more generally, a useful platform to measure an analyte in a liquid, such as waste water, treated water, or industrial processes, including for quality-control monitoring.

The aforementioned advantages are achieved herein by a specially configured probe having a small footprint suitable for implantation. The small footprint configured for insertion into biological tissue is obtained by integrated fluidic components for analyte collection, specialized analyte storage in a fluid (e.g., water-based fluid, such as buffered saline, artificial cerebral spinal fluids and the like) and analyte analysis in a single chip (substrate) configuration. This reflects that the probe is formed from a unitary material, including a doped silicon substrate, and use of a plurality of different materials is avoided. The probe can use a single port for collection of fluid sample and/or analyte from the biological fluid (e.g., port is an outlet that is also used for introduction of biological fluid or analyte, thereby forcing analyte into the probe) and subsequent analysis (e.g., port is an inlet for forcing stored fluid out of the probe). Alternatively, the probe can have a separate port distinct from the inlet port for subsequent analysis. Alternatively, the probe can be manipulated by a force that provides a controlled fracture location to effectively generate an ionization port at a time when analysis is desired. Integrated immiscible fluid and fluid introduction provides a stored analyte fluid train of droplets, thereby preventing Taylor dispersion, to achieve high temporal resolution. In embodiments, the probe tip can serve a dual-function of biological fluid and/or analyte collection and, subsequently, electrospray ionization emitter for analysis of analytes in the biological fluid by mass spectrometry (MS). Of course, the probes and methods provided herein are compatible with other types of fluids, including in non-biological settings. For example, the sampling may be in an application associated with an industrial process, manufacturing process, quality control, water-quality application, such as in a sewage or treatment system used to monitor for materials of interest, including heavy metals.

Since the probe is small, the sample consumption amount can be minute, which provides a universal platform for trace detection circumstances, including in-vivo detection; compatible with various applications, including but not limited to neurochemical sampling. The probe geometry that can be configured to ensure minimal tissue damage makes long-term monitoring possible for a range of applications.

Examples include, glucose monitoring, blood analyte monitoring, vitamin level monitoring, hormone monitoring, cancer marker monitoring, disease state monitoring, including pathogen monitoring for bacterial or viral infection, and any of a range of chemicals that impact physiological function. Basically, any analyte that is part of a fluid that can be accessed by the probe distal tip end and introduced to the microfluidic channel can be stored in the probe for subsequent analysis, as desired, including by extremely sensitive and reliable analyzers, such as by MS, including a fluid that is associated with a biological application or a non-biological application.

Also provided herein are methods of using and methods making any of the implantable probes described herein. In an embodiment, the method relates to processing of a silicon substrate, including a silicon-on-insulator (SOI) wafer. Repeated masking and etching steps ensures precise microfluidic layout, including a flow junction between microchannels to form a train of stored biological samples along with a probe having a small-sized tip end for obtaining biological samples without substantially damaging biological tissue.

In an embodiment, the invention is an implantable biomedical probe for sampling a biological fluid. The probe comprises: an integrated on-chip probe body having a distal tip end, a proximal end and a microfluidic channel extending between the distal tip end and proximal end, wherein the microfluidic channel is embedded within a probe body cross-section configured for implantation into biological tissue with a cross-sectional area less than or equal to 10,000 pmt. The probe is compatible with various size ranges, but it is particularly desired to have as small a cross-sectional area as possible to minimize tissue damage, while also achieving reliable sample collection, storage and release for subsequent analysis. A microchannel opening at the distal tip end provides a transport of biological fluid to the microfluidic channel. For subsequent ionization upon release of biological fluid for analysis, the microchannel opening is preferably small. As described herein, however, the ionization can occur at a separate ionization port, so that the small size of the opening may be relaxed in certain embodiments. An immiscible fluid microchannel fluidically connects with the microfluidic channel to form a microfluidic junction for segmenting biological fluid into a train of segmented biological fluid, wherein adjacent biological fluid segments from the microchannel opening are separated by an immiscible fluid introduced by the immiscible fluid microchannel. In this manner, temporal information is maintained for the stored train of biological fluids. A fluid outlet is positioned at the probe body proximal end and in fluidic contact with the microfluidic channel. This facilitates sample collection. Optionally, a flow (or pressure) controller is connected to the fluid outlet and is configured to generate a negative pressure, so that fluid flows in the microchannel and biological sample enters the microchannel opening. In this manner, biological fluid is collected in the microfluidic channel. A biological fluid storage system provides for temporary storage of a train of the segmented biological fluid, wherein the storage maintains temporal collection of the biological fluid collected into the fluidic channel. The storage system may correspond to the microfluidic channel itself.

In this manner, the implantable biomedical probe can provide a desired total collection time by selection of sample inflow volumetric flow-rate, immiscible fluid flow-rate, and volume of microchannel. For example, a total collection time of biological fluid of up to 20 hours, 5 hours, 1 hour, including between 1 minute and 5 hours, and sub-ranges thereof, including between 30 minutes and 1 hour.

In an embodiment, the invention is a method of analyzing an analyte in a biological sample with any of the probes provided herein implanted in a biological tissue.

In an embodiment, the invention is a method of making any of the probes described herein, including by processing a silicon-on-insulator (SOI) wafer so that the probe body has the described micro-sized or less dimensions suitable for biological implantation.

In an embodiment, provided herein is an implantable biomedical probe for sampling a biological fluid or an analyte of a biological fluid. The probe comprises an integrated on-chip probe body having a distal tip end, a proximal end and a microfluidic channel extending between the distal tip end and proximal end. The microfluidic channel is embedded within a probe body, including in at least the distal end having a cross-section configured for implantation into biological tissue. The configured for implantation refers to a sufficiently small cross-section to avoid undue tissue damage. For example, the cross-sectional area can be less than or equal to 10,000 $\mu m^2$, and more preferably less than or equal to 1,000 $\mu m^2$. In this manner, the probe is configured for long-term in vivo implantation without substantial tissue damage, including in a brain.

A microchannel opening at the distal tip end provides an entry point for biological fluid or the analyte of the biological fluid to the microfluidic channel. For embodiments where the bulk biological fluid is of interest, the biological fluid may be pulled into the microchannel by a flow controller that provides a negative pressure relative to the pressure of the biological fluid surrounding the distal tip end. For embodiments where only analyte suspending in the biological fluid is desired, the pressure at the distal tip end opening and the biological fluid may be equalized, so that analyte enters the microchannel by passive diffusion. Depending on analyte concentration, the fluid flow in the microchannel is adjusted so that a desired amount of analyte is contained in the fluid flowing in the microchannel.

An immiscible fluid microchannel fluidically connects with the microfluidic channel to form a microfluidic junction for segmenting the biological fluid or the analyte of the biological fluid into a train of a sample-containing fluid, wherein adjacent sample-containing fluid segments from the microchannel opening are separated by an immiscible fluid introduced by the immiscible fluid microchannel. A fluid outlet is positioned at the probe body proximal end and in fluidic contact with the microfluidic channel. A flow controller is fluidically connected to the microfluidic channel and the immiscible fluid microfluidic channel to control flow of the sample-containing fluid segments separated by the immiscible fluid in the microfluidic channel and to collect the sample-containing fluid segments separated by the immiscible fluid in the microfluidic channel. The flow controller may control pressure at various locations in the microfluidic channel, including as confirmed by one or more pressure sensors and/or flow rate sensors. Multiple separate flow control may be utilized to provide further adjustability, including independent flow control of immiscible fluid and fluid flow.

A fluid storage system is fluidically connected to the microfluidic channel for temporary storage of a train of the sample-containing fluid segments separated by the immiscible fluid, wherein the storage maintains temporal collection of the biological fluid or the analyte of the biological fluid collected into the microfluidic channel.

In this manner, the integrated on-chip probe provides sampling, storage and sample emission and/or detection for the biological fluid or analyte of the biological fluid in a unitary material that forms the probe body. This provides the ability to reliably sample at a precise spatial location in tissue, with no or minimal tissue damage, store sample, including over any of a short to a long-term collection window, and analyze at a later time, at convenience, all while maintaining good temporal resolution and without any long-term adverse impact to the animal or individual. The probes provided herein are a powerful platform that can be readily customized depending on the application of interest. For example, the sample emission may correspond to forced ejection of the train of samples for subsequent analysis, including electrostatic emission where fluid droplets are forced out of the probe under an electric field applied to the probe or doped portion thereof; the fluid samples may also be ionized, such as at an ionization port, for subsequent analysis. The detection may be independent of the emission, such as by an optical detector that optically detects analyte in the probe. In this manner, the integrated on-chip probe is configured to provide sampling, storage, and sample emission and/or detection for the analyte in a unitary material that forms the probe body.

For example, depending on desired collection time and/or temporal resolution, the fluid storage system can be customized to collect and store different total liquid volumes. For example, the fluid storage system may comprise a fluidic channel to accommodate a desired total sample volume. To maintain a desired relatively small footprint, different geometries may be utilized. For example, the fluid storage systems may comprise a serpentine channel having an effective channel length. Another example of maximizing channel length in a confined area is a channel having a spiral geometry. The effective channel length may be selected to provide a total collection time of the biological fluid or the analyte up to 20 hours, including up to 5 hours or 1 hour, depending on the application of interest.

The implantable biomedical probe is compatible with a range of immiscible fluids, so long as there is not substantial mixing of the immiscible fluid and the fluid in which collected analyte is stored. For example, the immiscible fluid may be oil, and the fluid in the microchannel is a biological fluid or an ionic solution in which the analyte is preserved. For example, the biological fluid may be extracellular brain fluid and the analyte is a chemical in the extracellular brain fluid that enters the microfluidic channel by diffusion.

The implantable biomedical probe can provide a range of volumes for each sample containing segment, such as a segment volume that is less than or equal to 50 pL.

The microfluidic channel may have an average diameter less than or equal to 50 µm.

The implantable biomedical probe may further comprise a high-voltage source for electrically energizing the probe body to electrically eject and ionize the biological fluid from the biological fluid storage system.

The implantable biomedical probe may have a sample collection mode and a sample analysis mode. The sample collection mode has a sample flow in a collection direction from the distal tip toward the proximal end; and the sample analysis mode has a sample flow in an analysis direction opposite to the collection direction and from the proximal end toward the distal tip. The distal tip end may correspond to a direct electrospray emitter to transfer the train of segmented biological fluid into a mass spectrometer, including an ESI emitter or an ionization port.

The implantable biomedical probe may further comprise an ionization port in fluidic contact with the fluid storage system for ejection and ionization of the train of segmented biological fluid. The ionization port may be positioned at the probe body proximal end.

The probe body may be formed from silicon that is heavily-doped, including portions thereof so as to locally confine high-electric field hot spots, including to regions at and immediately adjacent to the emitter used to introduce sample to an analyzer. In this manner, the entire probe body or a specific location on the distal probe end may be electrically energized so as to provide an appropriate ionized sample to a MS. This can greatly simplify the analysis while maintaining a small probe footprint. Localized doping of the tip rather than uniform doping of the entire probe body provides even further localized control of electric field hot spots. In an aspect, 75% or less of the distal probe end longitudinal length is doped.

The implantable biomedical probes are compatible with membrane dialysis applications, including by providing a membrane in fluidic contact with the microfluidic channel for membrane dialysis. The membrane may be configured to selectively pass only analyte of interest while ensuring unwanted material does not enter the microfluidic channel. This can further improve probe selectivity and sensitivity.

The implantable biomedical probe sample emission may comprise an electrospray emitter, such as an electrospray ionization (ESI) emitter or an ionization port for introduction of ions into a mass spectrometer, including an ionization port for direct infusion of ions into the mass spectrometer. The electrospray emitter may also provide droplet ejection without ionization to deposit by electric field controlled droplet deposition onto a substrate for MALDI-MS.

The implantable biomedical probe can be configured to detect an analyte in the biological fluid at a concentration of less than or equal to 100 nM. This is achieved by a combination of various parameters, such as flow rates, microfluidic channel size and length, and relative flow rates.

The implantable biomedical probe may detect two or more analytes in the biological fluid. This is achieved by collecting two or more analytes and then selecting appropriate analyzers that can reliably distinguish between the two or more analytes, including an appropriate MS detecting appropriately resolved peaks.

The implantable biomedical probe may further comprise a mass spectrometer (MS) operably connected to an ESI emitter located on the probe body for analyte detection. Of course, other analyzers may be used, including those based on Raman spectroscopy, flow cytometers, coulter counters, and optical-detection analyzers such as fluorescent detectors or particle detectors.

The implantable biomedical probe may have a distal tip geometry and the microchannel a fluidic characteristic to provide a temporal resolution of 1 second or better and a spatial resolution of 100 µm or better. The tip geometry may be an orifice area, effective diameter, and/or shape. The fluidic characteristic of the microchannel may be length, cross-sectional area, effective diameter, flow-rate and/or relative flow-rate between the immiscible fluid channel and the fluid channel.

Any of the implantable biomedical probes may have a unitary material that comprises a silicon substrate, including a silicon-on-insulator (SOI) substrate.

The implantable biomedical probe may further comprise an accessible element positioned between the probe body distal tip end and the proximal end, wherein an ionization port is formed upon access of the accessible element for providing an ionized analyte to a mass spectrometer.

Also provided herein are methods of analyzing an analyte from a biological fluid using any of the implantable biomedical probes described herein. For example, the method may comprise the steps of: implanting the implantable biomedical probe into a biological tissue; collecting the analyte from the biological fluid in the microfluidic channel; segmenting the collected analyte in a fluid sample in the microfluidic channel into a train of segmented analyte fluid samples, with adjacent segmented analyte fluid samples separated by an immiscible fluid; storing the train of segmented analyte fluid samples in a fluid storage system so that the train of segmented analyte fluid samples are maintained; and electrically energizing the stored train of segmented analyte fluid samples to eject (e.g., for MALDI) and ionize (e.g., for ESI) the analyte fluid sample from the fluid storage system and toward a mass spectrometer. In this manner, one or more analytes in the biological fluid sample are analyzed.

The method of may further comprise the steps of: removing the probe from the biological tissue; and accessing an accessible location on the probe body at a location between the distal tip end the proximal end to form an ejection and ionization port, wherein the step of electrically energizing ionizes the train of segmented analyte fluid samples that exits the probe at the fracture location.

Also provided herein are methods of making any of the biomedical probes described herein. For example, the method of making may comprise making the probe body by the steps of: providing a silicon-on-insulator (SOI) wafer having a silicon device layer thickness less than or equal to 20 µm; depositing a photoresist (PR) layer on top of the silicon device layer; patterning the PR at a distal tip region of the probe body to define a locally doped region; local doping of the silicon device layer to a sheet resistance that is less than or equal to 0.1 Ohm*cm; stripping the PR layer; depositing a mask layer formed of silicon oxide or silicon nitride on the silicon device layer surface; depositing PR layer on the mask layer; patterning the PR layer on the mask layer with a series of round openings, the round openings having a diameter less than or equal to 1 µm, wherein the series of round openings are arranged in lines having a separation distance from adjacent holes less or equal to 10 µm (see, e.g., FIG. 7 (panel A), where holes start to merge to make a microchannel) to expose a mask pattern for formation of microfluidic interconnected channels; etching the exposed mask pattern to expose a top surface of a silicon device layer; etching the exposed pattern into the silicon device layer to a depth that is less than the SOI device layer thickness that enables adjacent holes in the silicon device layer to merge laterally into a microfluidic channel; stripping PR layer from the mask layer; depositing a layer of silicon oxide or silicon nitride of less than or equal to 5 µm thickness to overgrow the round openings in the mask layer; applying and patterning a PR on a top overgrown layer to define a device perimeter; etching the top overgrown layer to expose a top silicon device layer; etching the exposed silicon device layer to expose the SOI buried oxide layer (BOX); stripping the PR layer; applying a PR to a backside handle silicon layer of the SOI; patterning the PR on the backside SOI handle silicon layer to define a proximal end perimeter, a distal end perimeter, and an ionization port perimeter; etching the backside handle to expose the BOX layer to isolate the proximal end perimeter, to undercut the distal end perimeter, and undercut the ionization port perimeter from the rest of the wafer; stripping the backside handle PR to obtain the probe supported on the wafer by bridges that connect the probe to the wafer at the probe corners; and releasing the probe from the wafer by breaking the bridges at the probe corners; thereby making the probe body of the implantable probe.

In an embodiment, the biomedical probe is configured as a disposal cartridge. In other words, the sample is collected and stored in the probe body, and at the desired time the sample is released from the probe body for analysis and at least the probe body is disposed of. Integration of microfluidic channels, sampling area, droplet-segmentation devices, droplet storage delay lines, and ionization ports, on a single monolithic silicon chip enables chip-scale disposable cartridges. Such cartridges facilitate wide dissemination of the technology for applications that may not have immediate access to high-performance MS capabilities. The chip-scale silicon cartridge is first used to sample in-vivo analytes from biological fluids and then, once the sampling is complete, remove the probe from the tissue and store it in a controlled environment (i.e. freezer). Such cartridge can be sent to an outside facility that has all the equipment necessary for high-performance chemical analysis (I.e. ESI-MS or MALDI-MS). The cartridge then delivers the time-preserved droplet sequence to the highly sensitive MALDI-MS or ESI-MS analysis by reversing the fluid flow.

In this manner, the implantable biomedical probes are made to have a robust temporal and a chemical resolution, including for very small total sample volumes, such as on the order of less than or equal to 10 pL. Such small sample volumes can be important for implant locations where it is desired to minimize total sample collected, such as for brain implantation for collecting biological fluid containing neurochemicals.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 10A: θ=90°, FIG. 10B: θ=120°, FIG. 10C: θ=150° FIG. 10D: Corresponding filling radius-junction angle plot.

DETAILED DESCRIPTION OF THE INVENTION

Figure 1A:
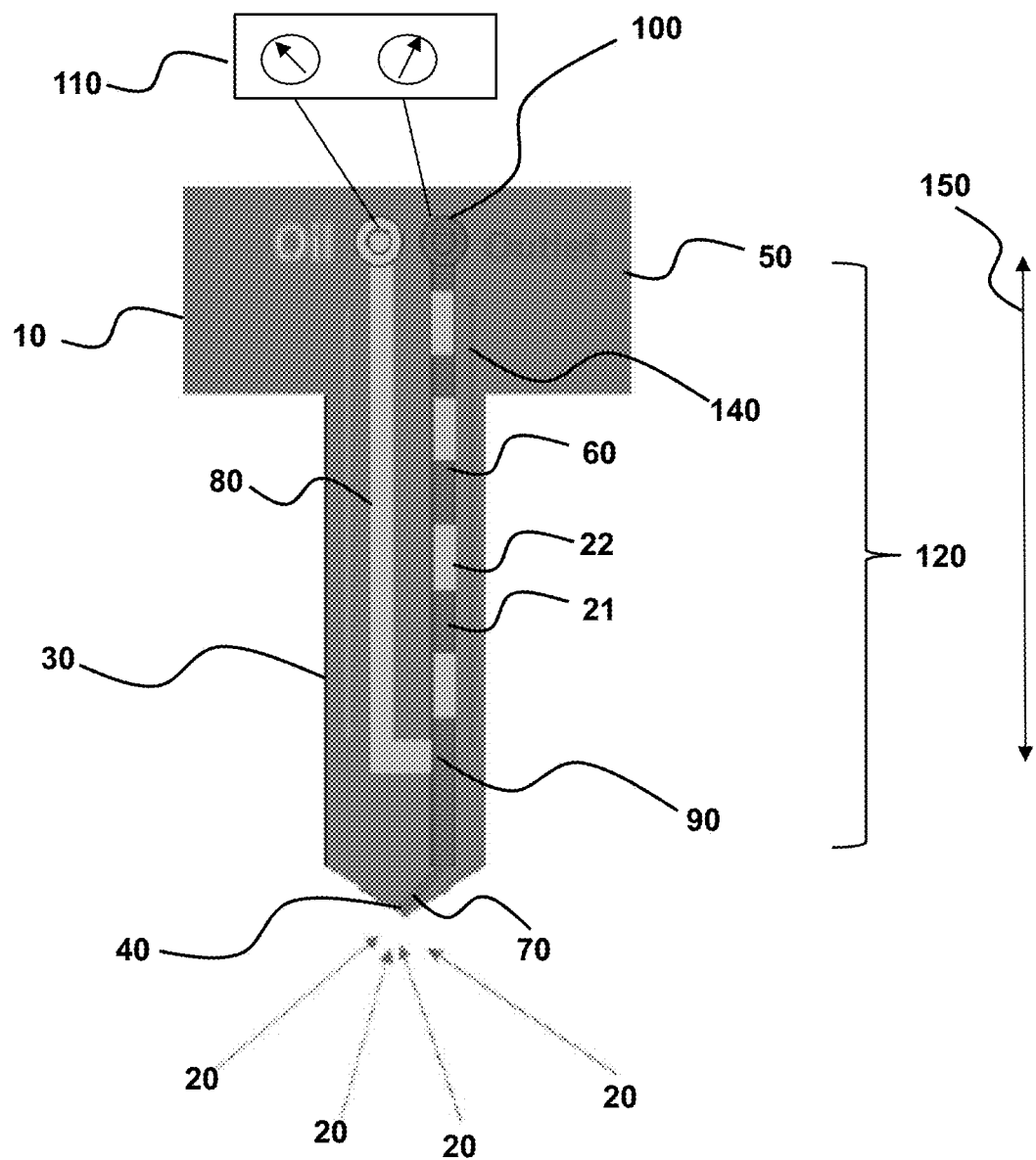
FIG. 1A is a schematic illustration of a probe for chemical sampling pulling, followed by immediate segmentation of inert oil to prevent Taylor Dispersion.

In the following description, numerous specific details of the devices, device components and methods of the present invention are set forth in order to provide a thorough explanation of the precise nature of the invention. It will be apparent, however, to those of skill in the art that the invention can be practiced without these specific details.

In general, the terms and phrases used herein have their art-recognized meaning, which can be found by reference to standard texts, journal references and contexts known to those skilled in the art. The following definitions are provided to clarify their specific use in the context of the invention.

The term "implantable" refers to the device that is configured to cause minimal or no observable damage during or after implantation into a biological tissue. The term recognizes that any act of implantation will cause minor irritation or disruption to tissue, but such disruption is not necessarily observable to the naked eye. Furthermore, there is no significant and prolonged immune response, clotting activity, or the like. In other words, the probe can be implanted for a time period and then removed, without lasting or permanent damage to the subject. This is in contrast to conventional devices, where the size of the system required to accommodate all the components provided herein can result in observable adverse events, at least in part due to the size of the device. This may include blunt force trauma and associated tissue damage, including blood vessel damage, immune response, scarring and up to an including observable tissue damage and death. Such damage can be quantified by measuring tissue damage markers, including proteins, enzymes and immune cells, depending on the biological tissue type. The damage/no damage may be quantifiably defined, such as a difference of at least 5%, 10% or 20% of one or more biomarkers in the implantation region compared to the value before the implantation. The probes provided herein provide the functional benefit of having small cross-sectional areas of insertion while still being "integrated" in that each of the collection, storage and analysis functionality is maintained by a probe body formed of one material, preferably highly-doped silicon.

"Integrated on-chip" refers to the probe body that is formed from a common starting substrate, such as a silicon or SOI wafer. The fluidic components for droplet generation and biological sampling are formed by processing the SOI wafer, including by repeated use of photoresist layer(s) (PR), patterning and etching. The ability to store analytes from a fluid, such as a biological fluid, as a train of droplets and subsequently, as desired, provides the analytes for analysis by, for example, mass spectrometry (MS), are also integrated with the common starting substrate without a need for other separate components. Accordingly, the term "unitary material" is used herein to refer to a single material that forms the common starting substrate, such as silicon, doped silicon, including SOI wafer.

"Probe body cross-section" refers to the cross-section of the probe that is configured for insertion into biological tissue. Depending on the application of interest, it preferably has a very small area, such as less than 10,000 $\mu m^2$, less than 1,000 $\mu m^2$ and even less than 500 $\mu m^2$ or 100 $\mu m^2$. The relatively high strength silicon provides the necessary strength to ensure the probe does not break during use. Depending on the tissue type, the cross-sectional area for insertion may be relaxed. For example, for brain insertion, the cross-sectional area may be on the small side to minimize brain injury; for skin insertion, the cross-sectional area may be larger as the risk of adverse impact due to skin injury is less than for brain. Accordingly, a portion of the probe body (e.g., the proximal end) may be relatively large because that portion need not be implanted, with another portion (e.g., the distal end or distal tip end) may be relatively small as that portion is implanted.

"Biological fluid" is used broadly herein to refer to fluid that is collected by the probe during implantation. The fluid can be intracellular fluid, extracellular fluid, synovial fluid, sweat, blood, saliva, tears, urine, and any other fluid associated with a biological tissue. "Analyte" and "chemical" are intended to be used interchangeably and refer to a substance within the biological fluid that is to be analyzed, preferably by a MS. For example, in brain tissue the analyte may be a neurotransmitter and/or metabolites thereof.

"Immiscible fluid" refers to a fluid that when combined with biological fluid, does not mix. Instead, there are immiscible fluid regions within the biological fluid. In this manner, there is a "train" of biological fluid samples, with adjacent biological fluid samples separated by immiscible fluid. Biological fluids tend to be water-based, and so a natural immiscible fluid is oil. Of course, other immiscible fluids may be used, so long as at the flow junction the train of biological fluid samples is obtained. For example, the immiscible fluid may be a gas, such as air, nitrogen, or other inert gas, particularly in view of the microchannel having small effective diameters so that the gas-biological fluid interface is maintained.

"Accessible element" is used broadly herein to refer to a location on the probe body that, once analysis of the collected analyte is desired, is able to provide collected analyte to an analyzer, including a mass spectrometer (MS). The special configuration of the probe unitary body formed from doped Si is particularly advantageous in one embodiment in that the probe body can be electrically energized to ionize sample containing analyte and/or pressure-drive flow can be used to force droplets out of the probe for subsequent analysis. In one basic embodiment, the accessible element refers to a structure and geometry at a location that facilitates controlled breakage or fracture. For example, the probe body may be fractured at a location between the probe body distal tip end and the proximal end to form an ionization port upon application of an electric potential to the probe body and the fracture location. Of course, other accessible elements are compatible, including microfluidic components such as a valve and port. The accessible element may be facilitated by a range of processes that provide access to a specified location, including by etching, focused ion milling, laser cutting, scribing and cutting of Si wafer material. In this manner, a well-controlled access to a specific location on the probe body is achieved such that collected samples are readily provided to an analyzer, such as a MS.

"Heavily-doped" refers to a semiconductor, such as silicon, having $10^{17}$ $cm^{-3}$ or greater, including an impurity concentration of about $10^{17}$ $cm^{-3}$ to $10^{20}$ $cm^{-3}$, and any subranges thereof.

The invention can be further understood by the following non-limiting examples.

The brain physiology of awake and behaving animals is, to a great extent, mediated by the chemical interactions between networks of neurons as well as between neurons and glia cells. These chemical messengers are basically neurotransmitters and neuromodulators, ranging from gases to small molecules and peptides. Since cell-to-cell signaling via these neurochemicals is the fundamental basis for brain functionalities, insights into the dynamics of neurotransmitters and their metabolites, in terms of spatial and temporal neurochemical concentration transients in the brain extracellular space, is a prerequisite for understanding the functionality of neural circuits and for implementing strategies for treatment of neural disorders.

While brain chemistry has proven indispensable in better understanding brain functions, the implementation of its measurement in vivo is actually a formidable project. First, many neuromodulators of interest are present at low basal concentrations below 100 nM. Therefore, chemical sensitivity and selectivity are crucial to the implementation of neurochemical measurements. Besides chemical resolution, restriction upon the size of invasive probes is imposed by requirements of minimal tissue damage and spatial resolution. Finally, to capture dynamics of the neurochemical levels, it's critical for a neural probe to respond to the time-varying chemical signals from the microenvironment, i.e. excellent temporal resolution (sub-second). These major performance metrics (temporal resolution, chemical resolution, spatial resolution and invasiveness) constitute significant challenges in aspects of both engineering and science, because these requirements tend to dictate mutually exclusive restrictions, and thus fundamental engineering tradeoffs for the design would come as expected in various developed devices.

Electrochemical sensors[1,2] have remained predominant for in vivo neurochemical monitoring. Such methods rely on use of microelectrodes. Typically penetrating microelectrodes were carbon fibers or conductive metal wires housed in glass pipettes to be insulated except at the tip. For example, fast-scan cyclic voltammetry (FSCV) detects electroactive molecules (e.g., dopamine and serotonin) via a redox reaction at the exposed electrode site. Although FSCV provides high temporal (<<1 sec) and spatial (<1 μm) resolution, it's only applicable to some specific neuromodulators (e.g. dopamine) with electroactive response. Moreover, the detected signal of interest might be masked by background interference from other electroactive metabolites also present in the cortical extracellular fluid at higher concentrations. That is to say, the limit of detection (LOD) is subject to degradation. Even worse, to collect detectable signal, the requirement of analyte accumulation on electrode results in limiting throughput and temporal resolution.

Microdialysis sampling[3-5] is an alternative sampling method for in vivo studies of analytes from the ECF. The microdialysis probe, is composed of sheathing inlet and outlet capillaries, and semi-permeable membrane. During sampling, a buffer resembling ECF is infused via the inlet. Analytes are collected by diffusive transport through the membrane following concentration gradients. Such dialysate is subsequently collected in fractions for future chemical analysis. The popularity of microdialysis lies in its favorable properties: The membrane prevents channel clogging by rejecting large molecules and debris from being collected. Besides, membrane-based devices are amenable to coupling to various downstream analytical techniques, e.g. LC-MS and CE-LIF, enabling neurochemical measurement with excellent sensitivity and selectivity. Promising as microdialysis sounds, it conventionally suffers from poor spatial resolution limited by the probe size typically approaching several mm, which is too large to measure local concentration gradient and also results in severe brain injuries.

Miniaturization of the neural probes, such as low-flow push-pull perfusion[6], promises to achieve better spatial resolution. Two microchannels are mounted side-by-side sheathed with an outer tubing. Tissue sample is withdrawn via outlet tube, while artificial cerebrospinal fluid (aCSF) is infused through inlet tube placed beside as make-up fluid at the same flow rate. Under such condition, the active sampling area is limited to the narrow spacing between the inlet and outlet. Therefore, its spatial resolution is inherently improved.

However, high temporal resolution does not come naturally with either low-flow push-pull sampling or conventional microdialysis. In particular, temporal resolution tends to be limited by Taylor shear-induced dispersion that leads to significant smearing out of the concentration distribution in the flow direction. Recent developments' attempt to solve this problem by segmentation of dialysate flow into a series of droplets spaced by immiscible oil phase. As analytes travel along the channels, diffusion is confined to a single droplet and thereby dispersion is minimized. Such flow segmentation is also applied to microdialysis with electrospray ionization MS (ESI-MS)[8] for in vivo monitoring of acetylcholine, demonstrating feasibility of real-time analysis on the brain physiological dynamics. However, temporal resolution was demonstrated to be still limited by residual Taylor dispersion in the long connecting tubing between the sampling tip and exterior droplet-generation device. Furthermore, such direct push-pull configuration exerts significant shear stress on surrounding brain tissue and is prone to clogging.

The probes and related methods provided herein are fundamentally different from previous droplet-based push-pull or microdialysis, which is still subject to Taylor dispersion in the long connecting tubing between sampling tip and exterior droplet-generation device. The probes provided herein integrate many discrete functionalities on a single micro-chip. In this aspect, "integrated" refers to a single chip that collects, stores, and provides an interface platform for introducing analytes from the chip to analytical MS systems. The is achieved by integrating: a) implantable neural sampling microdialysis probe (ether a direct sampling, a push-pull or with a microdialysis membrane), b) on-chip droplet segmentation, c) on-chip droplet storage device, and d) on-chip storage electrospray emitter All of these functional elements are integrated on a silicon-on-insulator (SOI) substrate using fabrication steps described herein. Silicon microfabrication enables buried microfluidic channels with a radius as small as about 5-7 μm, that can support ultraslow flow-rates in the range from sub-nL/min to 10 nL/min and droplet generation in the 1 pL to 20 pL regime.

Table 1 is a comparative summary to emphasis certain differences from the probes provided herein from conventional systems.

TABLE 1

Comparison with representative neurochemical sampling and detection methods:

| Conventional methodology | Working Principles | Exemplary difference from instant probes and methods |
| --- | --- | --- |
| Electrochemical sensors | Redox reaction at the exposed electrode site | Our methods inherit the traits of droplet-based push-pull, in terms of impressive spatial resolution, not limited to certain molecules (e.g. electroactive chemicals for Electrochemical sensors), and amenability to coupling to various downstream analytical techniques to achieve superior detection sensitivity and resolution. |
| Microdialysis | Diffusive transport through membrane | |
| Low-flow push-pull perfusion | Microchannels mounted side-by-side; Directly withdraw samples via one outlet and compensate as | |

TABLE 1-continued

Comparison with representative neurochemical sampling and detection methods:

| Conventional methodology | Working Principles | Exemplary difference from instant probes and methods |
|---|---|---|
| Droplet-based push-pull or Microdialysis | make-up fluid at the same flow rate Segmentation of dialysate flow to minimize dispersion | Different from previous droplet-based push-pull or microdialysis, which is still subject to Taylor dispersion in the long connecting tubing between sampling tip and exterior droplet-generation device, the instant probes and methods integrate droplet generation at the probe tip, and store the chemical droplets on the chip. The samples are collected, stored and detected directly all on the chip, by an integrated electrospray tip, which eliminates the residual Taylor dispersion and dead volumes. |

REFERENCES (1) Bucher, E. S.; Wightman, R. M. *Annual review of analytical chemistry* 2015, 8, 239-261.
(2) Robinson, D. L.; Venton, B. J.; Heien, M. L.; Wightman, R. M. *Clinical chemistry* 2003, 49, 1763-1773.
(3) Westerink, B. H.; Cremers, T. I. Handbook of microdialysis: methods, applications and perspectives; Elsevier, 2007.
(4) Nandi, P.; Lunte, S. M. *Anal Chim Acta* 2009, 651, 1-14.
(5) Kennedy, R. T. Current opinion in chemical biology 2013, 17, 860-867.
(6) Slaney, T. R.; Nie, J.; Hershey, N. D.; Thwar, P. K.; Linderman, J.; Burns, M. A.; Kennedy, R. T. *Analytical chemistry* 2011, 83, 5207-5213.
(7) Ngernsutivorakul, T.; Steyer, D. J.; Valenta, A. C.; Kennedy, R. T. *Analytical chemistry* 2018, 90, 10943-10950.
US20180272287, U.S. Pat. No. 8,431,888; U.S. Ser. No. 11/014,047; US20180272287
(8) Song, P.; Hershey, N. D.; Mabrouk, O. S.; Slaney, T. R.; Kennedy, R. T. *Analytical chemistry* 2012, 84, 4659-4664.

Example 1: Method and Structure for Single Chip Integrated Implantable Probe for Chemical Analysis of Biological Liquids In-Vivo Using Mass Spectrometry While brain chemistry has proven indispensable in better understanding brain functions, the implementation of its measurement in vivo is formidable. While typical concentration of excitatory neurotransmitters like glutamate (Glu) is high in the cortical extracellular fluid (ECF) reaching micromolar (μM) levels, many neuromodulators of interest are present at lower basal concentrations, such as below 100 nM. Accordingly, chemical sensitivity and selectivity are crucial to the implementation of neurochemical measurements.

Microdialysis and low-flow push-pull perfusion stands out as popular sampling methods for in vivo studies of brain chemicals. However, high temporal resolution does not come naturally with those methods. Taylor shear-induced dispersion leads to significant smearing out of the concentration distribution along flow direction. Efforts at addressing this problem include by segmentation of dialysate flow into a series of droplets spaced by immiscible oil phase, by which diffusion is confined to a single droplet containing the interface and thereby minimizing dispersion. However, temporal resolution remains limited by residual Taylor dispersion in the long connecting tubing between sampling tip and exterior droplet-generation device. Even worse, to achieve high recovery rate with standard microdialysis techniques, low flow rates are needed. Such low flow rates significantly impacts temporal resolution, resulting in an inability to reliably distinguish events occurring over time frames of about one minute or less.

Another problem is with sample analysis. Sensitive analytical chemistry methods (liquid chromatography, capillary electrophoresis, mass spectrometry (MS)) coupled with microdialysis allows the detection of multiple neurochemicals simultaneously and can yield attomole limit of detections (LODs). Recently, matrix assisted laser desorption ionization (MALDI)-MS was used to detect acetylcholine and choline in dialysate samples; however, this method is only compatible with offline analysis and 60 s temporal resolution. Electrospray Ionization-Mass Spectrometry was also demonstrated to monitor neurotransmitter, metabolite, and drug in the brain of live rats at 5 s temporal resolution. However, besides neural probe, additional sophisticated peripheral devices were required, including droplet generator and ESI emitter, which is bulky and prone to sample loss during transfer.

Most importantly, while segmentation of dialysate flow into pL-volume droplets helps to achieve very high temporal resolution below 1 second, packaging of the existing neural probes require connection to large and bulky glass capillaries that typically have dimensions much larger than microchannels carved on the probe itself. This results in intermixing of droplets and their merging into much larger volumes. Therefore, the ultimate time resolution of the method is not achieved.

Figure 1B:
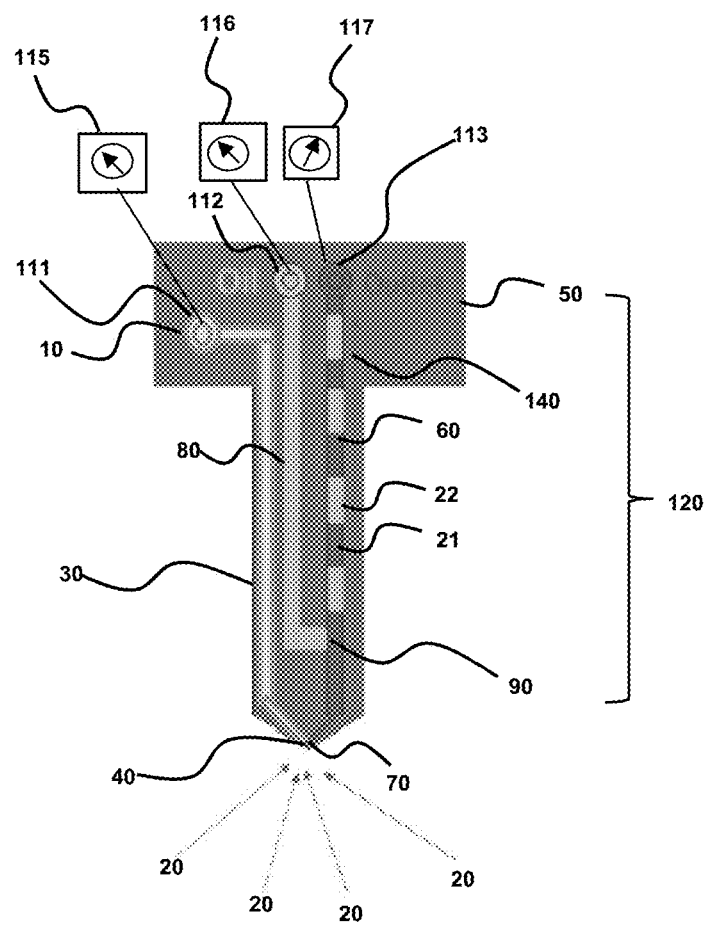
FIG. 1B schematically illustrates an embodiment where analyte within a biological fluid diffuses into a probe without substantial fluid flow into the probe from the biological fluid.
Figure 1C:
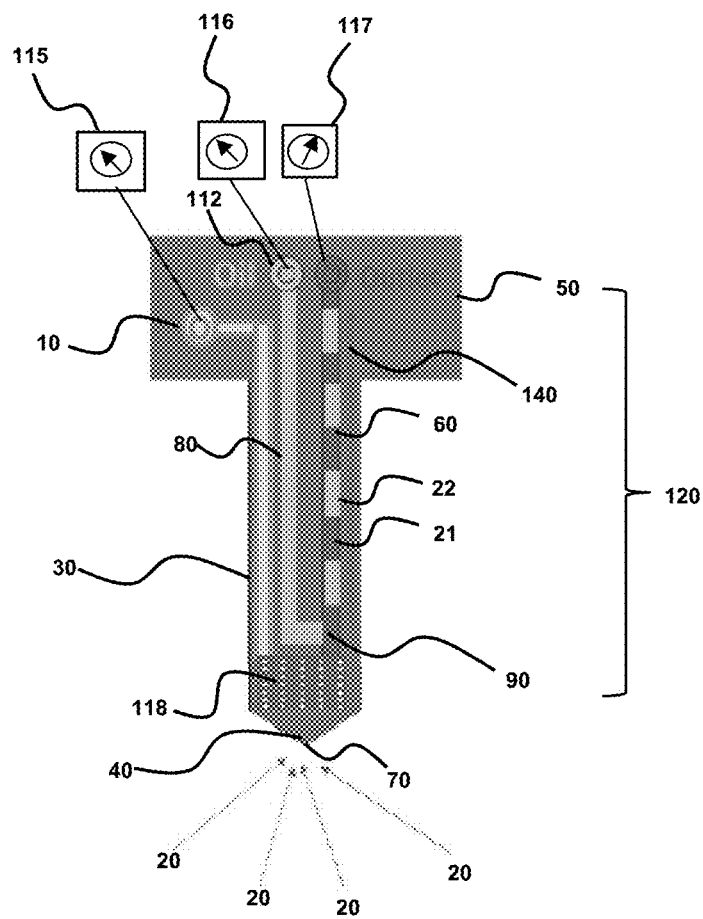
FIG. 1C schematically illustrates a membrane for microdialysis.

Provided herein is a platform that integrates functionalities of chemical sampling, transfer and interfacing to MS instruments, including ESI-MS, all on a single chip silicon neural probe. In this manner, in one probe the sample is obtained, stored and then later analyzed, all in a manner that achieves high temporal sensitivity, including on the order of less than one minute, less than 30 s, less than 10 s and less than 1 s, such as between 0.5 ms and 10 s. FIGS. 1A-1C illustrate various embodiments of an implantable biomedical probe 10 for sampling a biological fluid 20. A probe body 30 has a distal tip end 40 and a proximal end 50, with a microfluidic channel 60 extending therebetween. A microchannel opening 70 at the distal tip end 40 provides biological fluid from the surrounding environment to the microfluidic channel 60 and/or analyte in the biological fluid, including analyte by passive diffusion without substantial exchange of liquid. For example, analyte 20 may diffuse into microchannel via the opening 70 without a substantial amount of fluid entering the microfluidic channel. As explained in FIG. 1B, this can be accomplished by setting the pressure in the microchannel at the opening to substantially equal the fluid pressure in the surrounding environment outside the opening (e.g., about atmospheric pressure). The surrounding environment can be biological tissue or an organ, including brain. In this manner, the probe body is configured to have a geometric shape, size and orientation to minimize tissue damage and facilitate implantation. For example, the overall probe footprint (surface area) may be less than 1 cm$^2$, less than 25 mm$^2$, or less than 5 mm$^2$, with a cross-sectional area of a portion that enters the biological tissue less than 5 pmt.

To ensure the temporal aspect of the biological fluid is maintained, such as wherein analyte(s) within the biological fluid may change over time, an immiscible fluid microchannel 80 is fluidically connected to the microfluidic channel 60, such as a microfluidic junction 90. FIG. 1A illustrates junction at a right-angle configuration. Depending on the application of interest, the probe is compatible with other angles and geometries, including acute or obtuse angles. See, e.g., FIGS. 4, 5, 8-12. In this manner, biological fluid 20 is stored in the biological fluid storage system 120 as a train of segmented biological fluid 21 separated by immiscible fluid 22. The storage system 120 is illustrated, for clarity, as a straight-line fluid conduit. The probe is compatible, however, with other geometries, such as serpentine, meandering and/or helical, and/or other geometry that effectively increases channel length while minimizing probe footprint. In particular, for applications where high temporal sensitivity is desired over relatively long timeframes, a larger channel length is desirable. Flow controller 110 is schematically illustrated as providing independently adjustable control of pressure and/or flow-rate at a fluid outlet 100 for obtaining biological fluid or ejecting fluid sample for analysis (see, e.g., FIG. 2), so that the flow direction 140 is reversible and controllable. The oil inlet flow may be independently controllable, as indicated by separate pressure control (e.g., flow controller) at the oil inlet. Other flow control configurations are illustrated in FIGS. 1B-1C. The controller may be a microcontroller, and use electronically-controlled solenoids for precise pressure and/or flow-control. Various other components may be incorporated to provide reliable control of flow in any of the microchannels, such as valves, actuators, micropumps, transducers, sensors and the like, including to obtaining a desired train of stored samples, obtaining a fluid sample, storing a fluid sample, and for subsequent analysis of fluid sample. Exemplary flow controllers include, but are not limited to, pumps, such as micro-syringe pumps, to more simple devices such as forcing of fluid flow generated by a difference in the height of a flow inlet relative to a flow outlet. Of course, more complex and automated flow controllers are compatible with the probes provided herein, including flow and/or pressure sensors with automatic feedback loops to ensure desired flow-rate is achieved.

With respect to use of the device of FIG. 1A, during sampling a negative pressure is applied at the outlet 100, which actuates the pulling of a fluid sample from the surrounding environment, including chemicals from brain, into the channels embedded at probe tip. Once the chemicals enter, they are immediately segmented by the oil 22 at microfluidic junction 90, which halts the Taylor dispersion. Thereby, each droplet of biological fluid 21 carries the information of chemicals (also referred herein as analytes), with full fidelity, to downstream, and is stored temporarily in the long serpentine channels for later analysis.

Referring to FIG. 1A, the microfluidic channel 60 is illustrated as having a straight geometry and an effective channel length as illustrated by arrow 150. As desired, that straight geometry can be replaced with a serpentine geometry, wherein the longitudinal axis can curve back onto itself in a periodic manner, thereby increasing the effective storage volume and, thereby, the time course over which the analytes may be measured. For example, a serpentine geometry that doubles back on itself three times, would have an effective channel length of at least three-fold of length 150, with a corresponding increase in temporal analysis for a time course of at least three-fold of the geometry illustrated in FIG. 1A. In this manner, the time course over which chemical analysis occurs can be effectively increased while avoiding a corresponding increase in the probe body surface-area footprint.

Additional configurations and operation modes are illustrated in FIGS. 1B and 1C, including for applications where this is no or insignificant liquid exchange across the microchannel opening (sampling inlet) 70. FIG. 1B illustrates a push-pull configuration where the inlet pressure is equal to the outlet pressure at the microchannel opening 70. In this aspect, there is no direct fluid exchange as there is no pressure difference across the sampling inlet positioned at distal tip end. Analyte in biological fluid is sampled by diffusion (as indicated by direction of arrows 20) of analyte from relatively higher concentration outside the probe tip toward the lower concentration in the microfluidic channel in the probe body. Temporally-relevant storage is maintained by controlling fluid flow in microfluidic channel 60, such as by adjusting pressure(s) at fluid inlet 10 by fluid inlet flow controller 115, fluid outlet 113 by fluid outlet flow controller 117 to achieve a desired fluid flow rate in the microfluidic channel 60. Immiscible fluid introduction into the fluid flowing in the microfluidic channel 60 is controlled by immiscible (labeled as oil) inlet flow controller 116. As analyte 20 diffuses into microfluidic channel the flow of liquid in the channel conveys analyte downstream toward microfluidic junction 90 where an immiscible fluid (e.g., oil) is introduced into the liquid containing analyte 20, thereby generating a train of segmented fluid 21, with each segment corresponding to a well-defined temporal time point or range within the overall sampling. As desired, flow control (e.g., pressure control) can be provided upstream and/or downstream of junction 90 to provide a well-controlled fluidic characteristics (e.g., liquid flow, length of immiscible fluid segments 22 and/or length of liquid containing analyte 21), which, in turn, defines temporal sensitivity and overall sampling time. For example, lower flow-rates can be used to facilitate longer-term monitoring. Higher flow-rates and/or more frequent introduction of immiscible fluid facilitates increased temporal sensitivity for applications where it is desired to have a more fine temporal resolution.

FIG. 1C illustrates a microdialysis configuration wherein a dialysis membrane 118 is positioned at the probe body distal tip end for microdialysis. In this configuration, there is substantially no fluid exchange, but instead there is sampling by analyte diffusion.

The probes provided herein are compatible with a range of biological fluids and analytes within the biological fluids, and is configured for implantation in a number of biological tissues or organs. The probe may be inserted into a tissue to collect interstitial fluid. The probe may be configured for insertion in the brain and used to collect brain-related fluid. In this manner, brain-related chemicals may be analyzed, such as neurotransmitters for time-course analysis of neurotransmitter levels. The probe is further compatible with a variety of operation modes.

Figure 2:
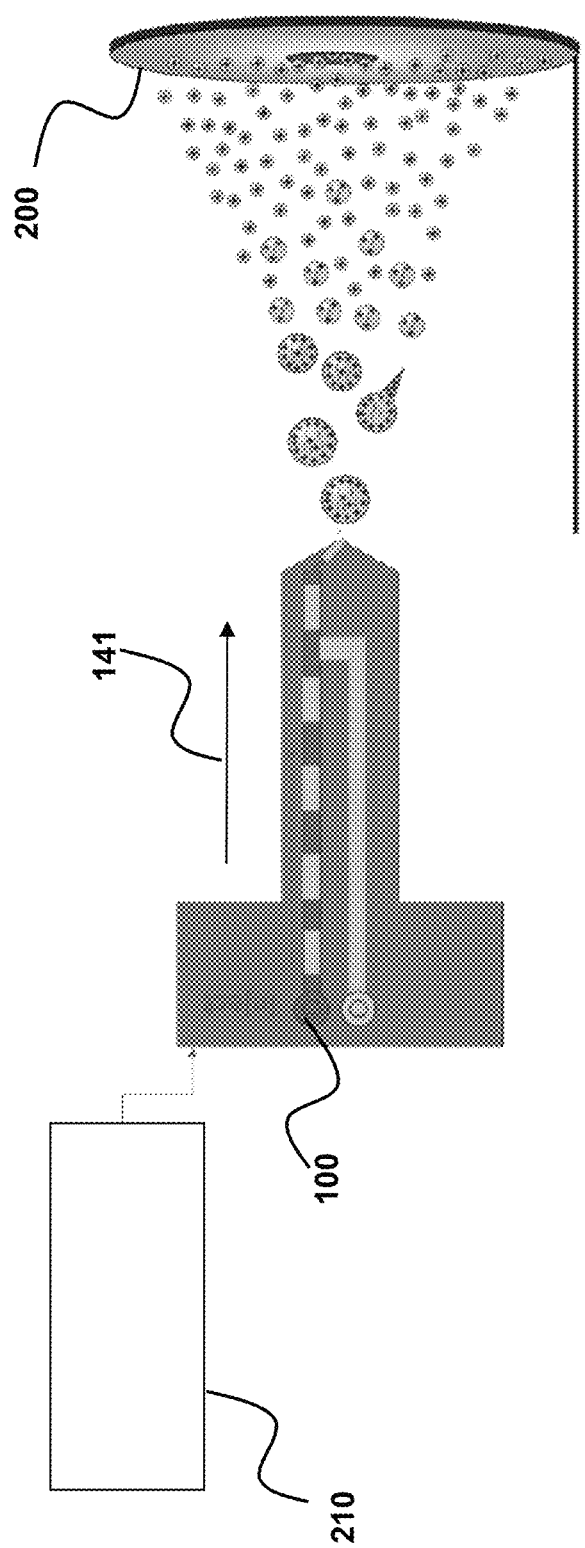
FIG. 2. Illustration of a probe distal tip end employed as a direct electrospray ionization (ESI) emitter to transfer the on-probe-stored droplet trains into a mass spectrometer (MS).

One operation mode is exemplified in FIG. 2. During detection, the fluid outlet 100 can functionally be used as a type of inlet, so that the pre-stored train of droplets 21 illustrated in FIG. 1A are reversely pushed to the probe distal tip end 50. Due to high flow resistance along the oil channel 80, the droplets tend not to enter that immiscible fluid microchannel 80 and, instead, flow out through the probe distal tip end 40 via the microchannel opening 70. In this manner, the microfluidic channel accommodates flow in a forward direction 140 during sample collection (FIG. 1A) and a reverse direction 141 during sample analysis (FIG. 2).

A high-voltage source 210 is used to apply high voltage to the probe body. FIG. 2 illustrates the high-voltage source 210 electrically connected toward the proximal end of the probe body, including at a wide base of the probe. In this manner, the probe substrate is preferable formed of a low resistance material so that voltage loss on the probe is minimal, particularly for an electrical contact point that is relatively distant from the region where biological sample is forced out of the probe and ionized for analysis by MS. In an embodiment, heavily-doped Silicon is used as the probe substrate, so the voltage loss on probe is minimal, and a high voltage between probe tip and MS is expected, which facilitates electrospray, as illustrated in FIG. 2. Therefore, the stored droplets are correspondingly sequentially ionized and transferred to MS for online analysis.

Figure 3:
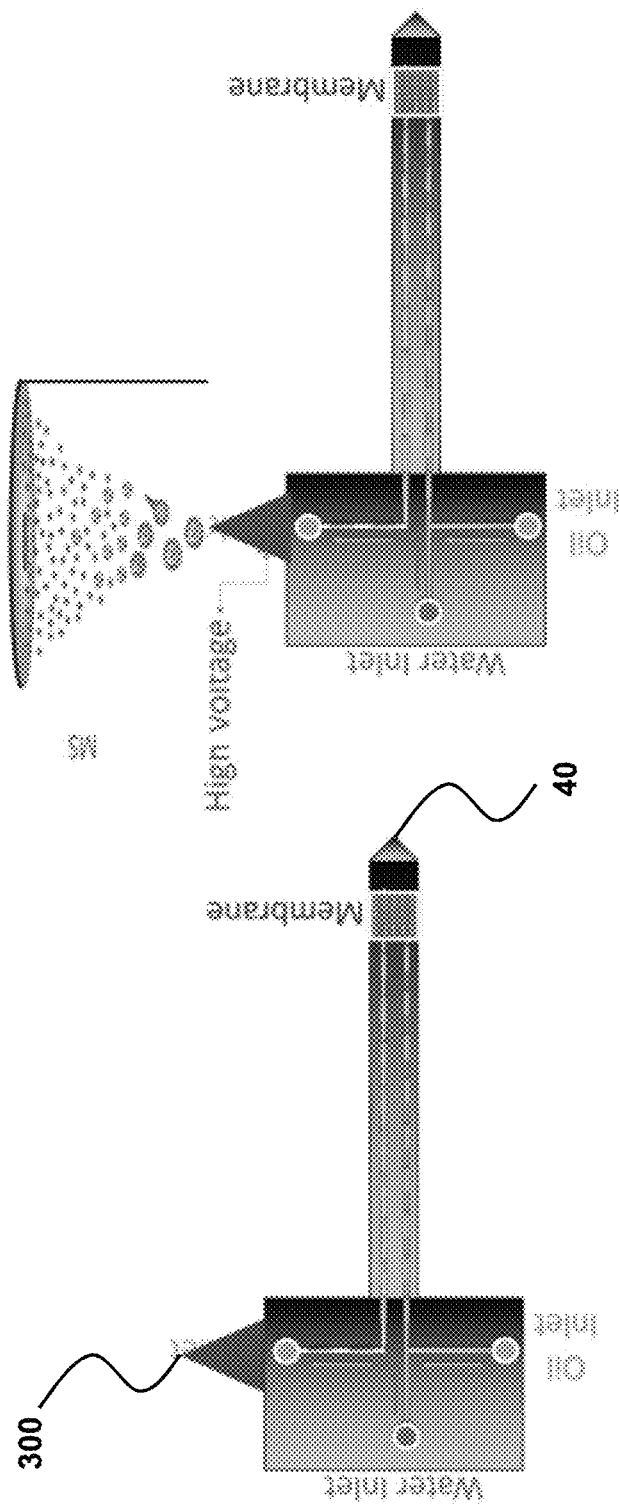
FIG. 3. Illustration of a probe tip on the outlet of the probe. In chemical sampling mode (left panel), a series of droplets are stored on the chip, while in the analysis mode (right panel) these droplets are released from the outlet and electrosprayed to transfer the on-probe-stored droplet trains into MS.

Another operation mode is for a probe having an additional ionization port 300 to which the flow of segmented droplets is directed in the reverse flow (FIG. 3). This facilitates probe compatibility with other, less invasive, methods for sampling biological fluids including push-pull and membrane dialysis.

The devices and methods provided herein have a number of advantages, including:

1. All in one: The neural probe integrates all functions, including chemical sampling, storing and electrospraying, on a single monolithic substrate. Integrated electrospray emitter eliminates complex external ionization interfaces and external droplet generators as in prior demonstrations. In this manner, ultimate temporal and chemical resolution can be achieved since droplets retain their initial volumes and time sequence. Moreover, there is no or very minimal loss of analytes during transfer to mass spectrometry analysis. Furthermore, the silicon microfabrication enables the channel orifice to be small in a controllable manner, and thus ESI emitter's performance can be improved. For example, the microchannel opening 70 can be less than 10 μm in effective diameter. Since the probe is small, the sample consumption amount can be minute, on the scale of just a few pL, which makes it a universal platform for trace detection circumstances or in-vivo detection; compatible with various applications, including but not limited to neurochemical sampling.

2. Sample recovery rate and resolution: Since all the analytes are stored in situ within the probe body storage system, there is no risk of sample loss or dilution, compared with conventional methods of sample transfer out for offline analysis. Furthermore, because analytes are immediately compartmented within a segmented fluid sample once they are collected, Taylor dispersion is halted which preserves the temporal resolution regardless of flow rate. Moreover, sample degradation due to active enzyme attack, is also minimized due to limited enzyme concentrations within a single droplet.

Furthermore, methods like microdialysis depend on a concentration gradient to enable diffusion, which naturally means that the collected concentration in the channel is lower, and is especially unfavorable for low-concentration detection. In contrast, the probes and some of the methods provided herein directly sample the analytes without analyte loss, which preserves the analyte resolution.

Example 2: Picoliter Droplet Generation for Fast Monitoring of Brain Chemistry with Scaled Silicon Nanodialysis Probe Introduction: Chemical signaling is the basis of all neural computations in the brain [1]. However, the analysis of in-vivo real-time response of neural activity to release of neurochemicals is hindered by limitations of current approaches to monitor chemical dynamics in extracellular space with sufficient spatial and temporal resolution, and with high chemical sensitivity and selectivity.

Microdialysis is widely used as a powerful sampling method for in vivo studies of neurochemicals [2]. Dialysates are diffused through a membrane and are subsequently collected for further chemical analysis. To minimize brain tissue damage, the implantable neural probe needs to be scaled down by at least 100× with respect to conventional microdialysis probes. This also improves significantly spatial resolution, enabling measurements of local concentration gradients instead of a bulk average.

However, microdialysis is typically limited by poor time resolution, due to Taylor shear-induced dispersion that tends to smear out the concentration gradients of the analytes [3]. Segmentation of dialysate flow into a series of droplets spaced by immiscible oil phase can confine the analyte diffusion within a single droplet, thus preserving temporal resolution.

A significant challenge, however, relates to integrating a specifically designed droplet generator that can reliably segment the dialysate into pL-volume droplets in such a scaled space-limited neural probe. To achieve monodisperse droplets generation, T-junction is widely adopted due to its geometrical simplicity and function robustness, where typically the dispersed and continuous phases are being fed orthogonally to each other. While this classical T-junction geometry is a routine design in typical PDMS-based microfluidics with hydrodynamic channel diameters up to tens of micrometers at μL/min flow rates [4], it is, however, very challenging to achieve reliable droplet generation within scaled channels. First, scaled channels restrict droplet volume, while, to collect enough molecules of interest from cortical extracellular fluid for downstream analysis, the target droplet volume should exceed 50 pL. Second, among various break up modes, squeezing regime is expected, since it enables generation of droplets with larger volume and high monodispersity. However, to realize such a regime within size-limited channels, flow rates have to be within sub-nL/min that makes it difficult to control.

While segmentation mechanism was previously discussed in relation to fluid physical properties and flow rate [5], this paper reveals how junction angles modulate droplet generation, in terms of break-up mode transition and droplet volume control.

Figure 4:
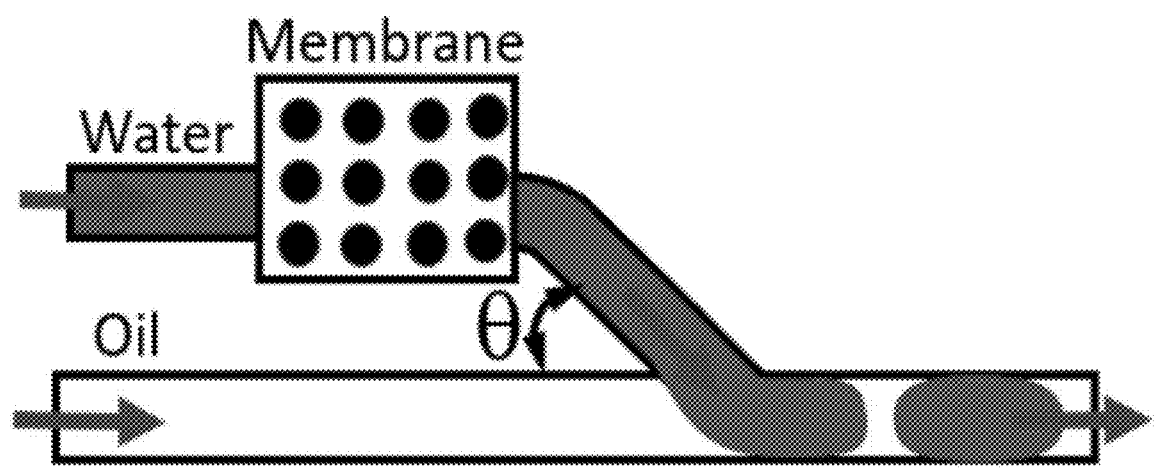
FIG. 4. Schematics of the droplet generation in a nanodialysis probe having a membrane.
Figure 5:
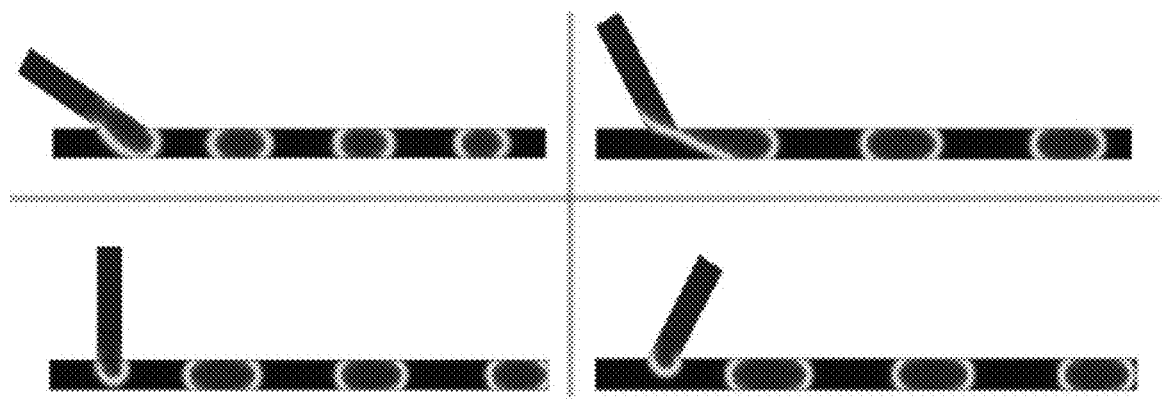
FIG. 5. COMSOL simulation of droplet generation within various angled T-junctions.

Design and Experiments: Simulation model. FIG. 4 illustrates the schematics of the integrated T-junction (e.g., "microfluidic junction") for droplet generation. We adopted the two-phase level set method [6] to perform finite element analysis of droplet formation in the T-junction to track the geometric evolution of the fluidic interfaces between two immiscible fluids. The level set function $\phi$ is configured such that water-oil interfaces are located by the 0.5 contour of $\phi$. The horizontal main channel is set to be initially filled with continuous phase (octanol), while the dispersed phase (water) is placed in the side inlet channel as shown in FIG. 4. The governing equations consist of the incompressible N-S equation (1), continuity equation (2) to satisfy the condition of mass conservation for incompressible flows, and the level set equation (3) for $\phi$ advection:

$$\rho \frac{\partial u}{\partial t} + \rho(u \cdot \nabla)u = \nabla \cdot [-pI + \eta(\nabla u + (\nabla u)^T)] + \sigma\kappa\delta n, \quad (1)$$

$$\nabla \cdot u = 0, \quad (2)$$

$$\frac{\partial \phi}{\partial t} + u \cdot \nabla \phi = \gamma \nabla \cdot \left[\epsilon \nabla \phi - \phi(1-\phi)\frac{\nabla \phi}{|\nabla \phi|}\right], \quad (3)$$

where u is velocity field, $\rho$ is the fluid density, $\eta$ is dynamic viscosity, $\sigma$ is surface tension, $\delta$ is the function concentrated at the interface, and $\kappa$ is the curvature of the interface. p denotes pressure, and $\gamma$ and $\epsilon$ are the numerical stabilization parameters. Simulation was carried out for T-junctions of different intersection angles ($\theta$) as shown in FIG. 5. Droplet shape and size, pressure evolution, and shear stress were extracted for different flow rate ratios.

Fabrication: The fabrication of silicon nanofluidic structures is comprised of channel fabrication and plumbing holes, including as summarized in FIG. 6. To fabricate fluidics channels, a pattern of 1.5-μm holes spaced 4 μm apart is etched into the oxide by contact lithography followed by plasma etching, as in (A-D). After stripping photoresist (PR) mask, hollow channels are formed in silicon by $XeF_2$ etching through the structured oxide mask. Etching parameters, e.g. etching rate and duration are specifically calibrated to etch until ~5 μm channel radius is achieved. Inlet and outlet plumbing holes on the back side of the probe are fabricated by deep reactive ion etching (DRIE) of silicon all the way through from the bottom side of the wafer, masked by the patterned photoresist, as illustrated in (G-H). Once the breakthrough is completed, PR is stripped, and the top surface of the wafer is bonded with a PDMS layer, mediated by plasma surface treatment and heating of both materials, to hermetically seal the holes in overcladding $SiO_2$ layer above the channel, as in (J). Capillaries with 250 μm ID are inserted to deliver fluids.

Figure 7:
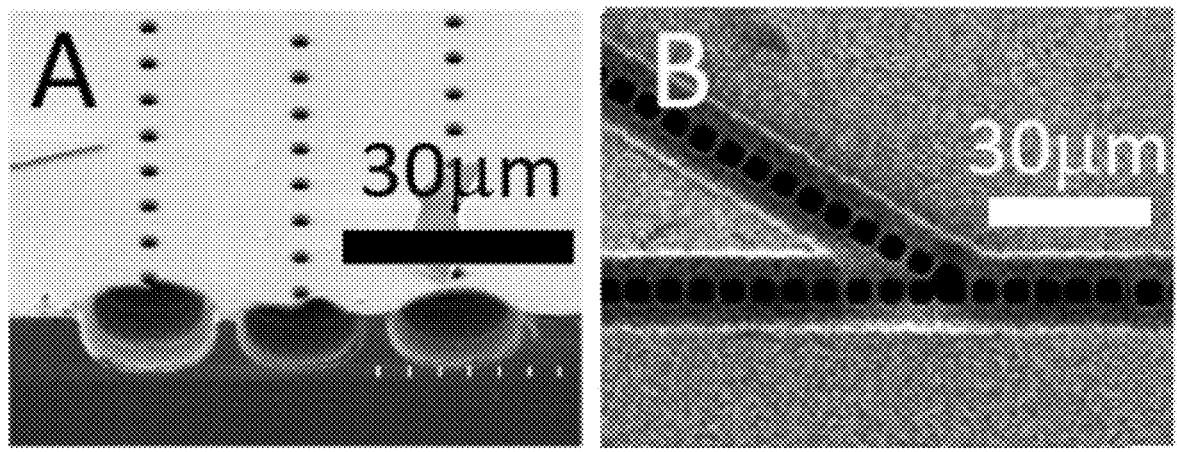
FIG. 7. A. SEM cross-section of nanofluidic channels. B. SEM top-down view of a T-junction. Channel radius is approximately 5 µm. [0047] The microfluidic channel cross-section is defined by patterning the PR layer with a series of round openings having less or equal to 1 µm diameter arranged in lines with separation distance between neighboring openings of less or equal to 10 µm as shown in FIG. 7 (top panel A). During the subsequent directional etching step of FIG. 6 (panel F) and isotropic silicon etch of FIG. 6 (panel H), the silicon device layer is etched to the depth of less than the device layer thickness that enables nearby holes in silicon device layer to merge laterally into a continuous microfluidic channel as shown in FIG. 7.

A series of devices with varying angle ($\theta$) of the T-junction are fabricated and characterized. A representative structure is illustrated in FIG. 7 ($\theta=30°$).

Figure 8:
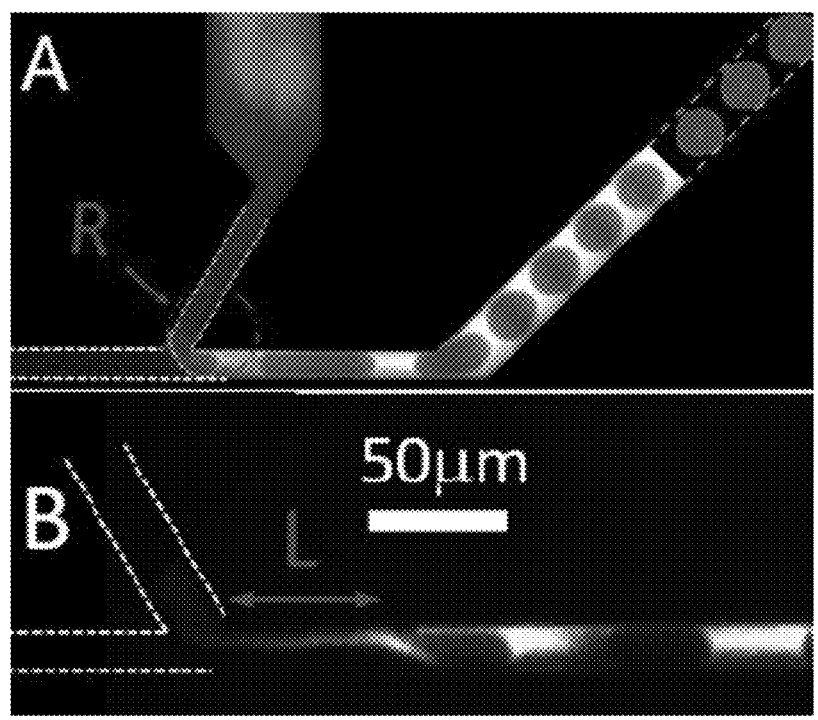
FIG. 8. Top panel A. Filling radius R and droplet volume measurements V in squeezing regime. Filled red circles depict fitted droplet volume. Bottom Panel B. Length of the neck L in jetting regime.

Computer vision for droplet size characterization: FIG. 8 (top panel A) illustrates the fluorescent image of droplet generation (water with fluorescent dye as dispersed phase; octanol as continuous phase). FIG. 8 (bottom panel B) shows appearance of intact jet prior to droplet formation that occurs at some certain flow rates, indicating transition from squeezing to jetting regimes. The intact jet length L is measured by counting pixels in images from the CCD camera, as in FIG. 8 (bottom panel B). Filling radius R, which refers to the curvature of the water-oil interface in the junction at the end of the filling period (see FIG. 8 top panel A) of droplet formation cycle, is evaluated by shape fitting. Computer vision algorithm is used to automatically extract droplet volume V using a combination of Gaussian filter smoothing, followed by mathematical morphology processing steps (hole filling and filtering, object dilation & erosion, etc.), followed by circle radius fitting. This procedure was done on the image captured downstream in the broader channel section (see FIG. 8 top panel A), where droplets become spherical.

Figure 9:
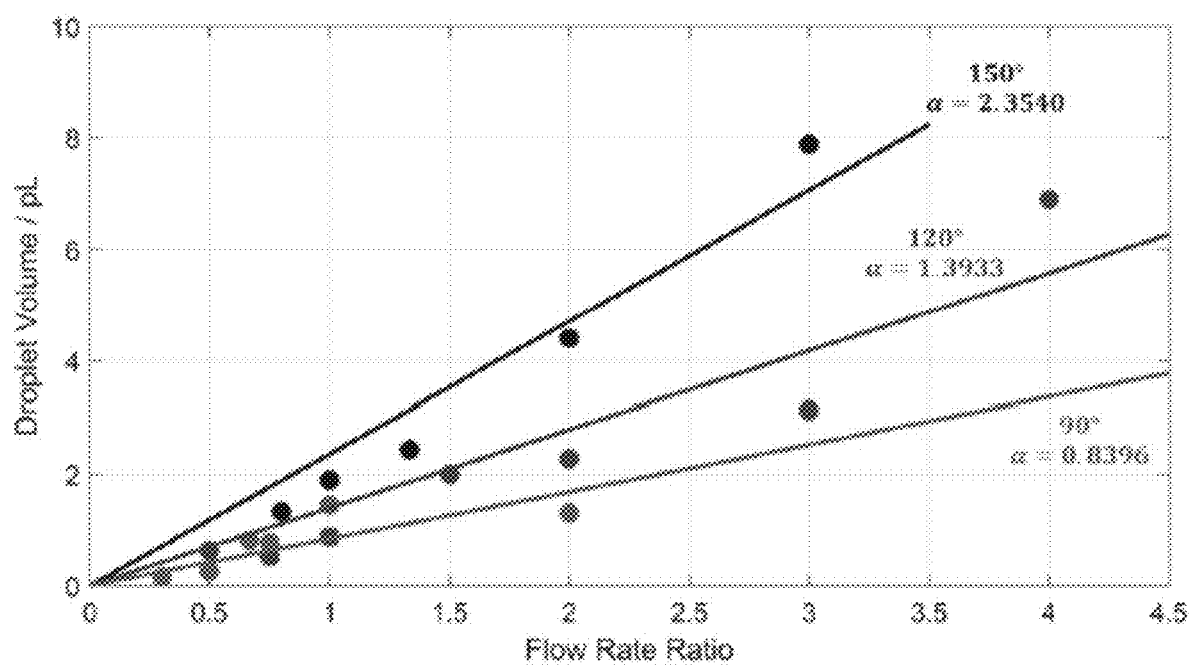
FIG. 9. Relationship between droplet volume and flow rate ratio shows dependence on T-junction angle for angles 90°, 120° and 150°.

Results and Discussion: Droplet volume: At low capillary numbers $Ca_c<0$ ($10^{-2}$), droplet generation falls into squeezing regime, where a formation cycle is comprised of filling period and squeezing period [7], and the droplet volume linearly scales with the ratio of flow rates of the dispersed and continuous phase $q_d/q_c$, i.e. $V=\beta+\alpha q_d/q_c$ [8]. Such linear relationship is experimentally verified within our angled T-junctions, as shown in FIG. 9. Moreover, we also found the linear slope a as a function of junction angle ($\theta$). Larger $\theta$ results in larger $\alpha$, indicating that larger droplet volume is generated at specific ratio of flow rates.

Generation of larger droplets with increased angle $\theta$ can be explained by the change of droplet shape imposed by the junction geometry. During squeezing period, droplets would grow to obstruct continuous phase stream, touching the walls of the main channel [9]. FIGS. 10A-10D shows that the filling radius R is decreasing with increasing junction angle that results in longer squeezing time, thus leading to larger droplet volume.

Transition between squeezing and jetting regimes: In squeezing regime of droplet generation at low Ca, viscous stress is less dominant than the droplet confinement by channel walls. Further increase in Ca would switch the droplet generation into jetting regime [10]. As a result, an extended liquid jet appears (See FIG. 8 bottom panel B) that emits polydisperse droplets. Thus, there exists a critical capillary number, above which transition from squeezing to jetting regimes takes place.

Figure 11:
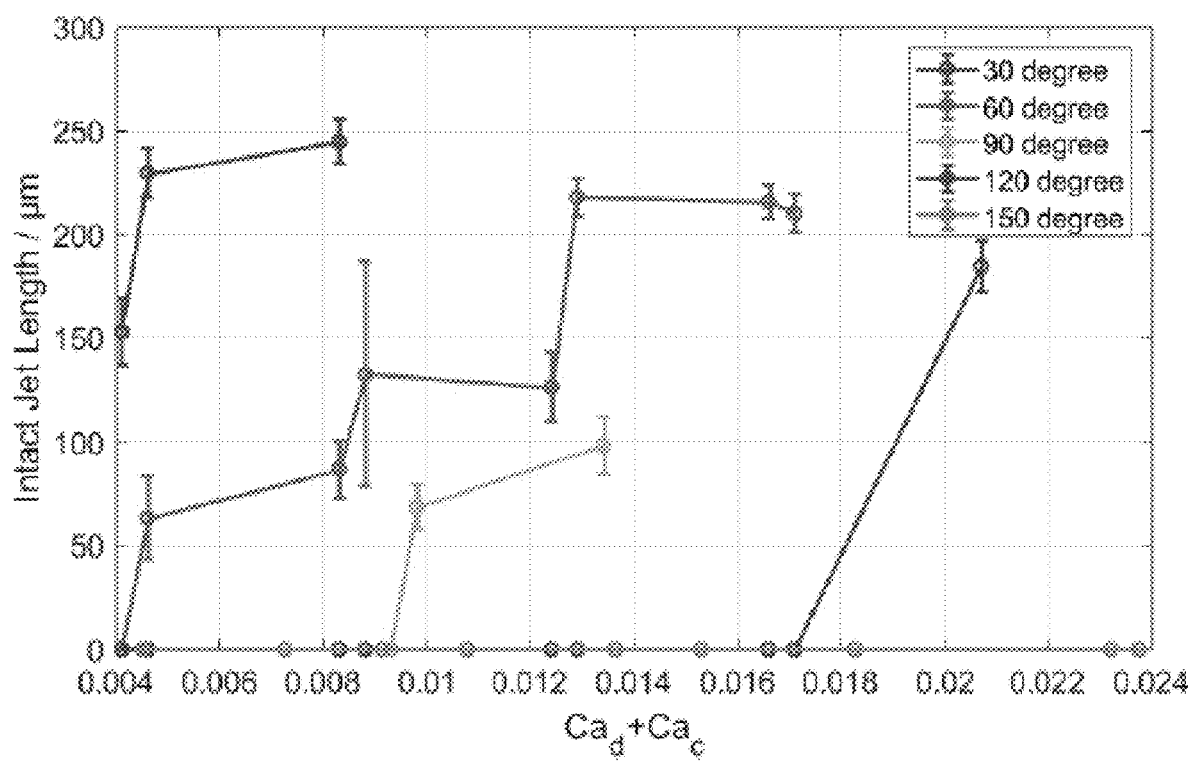
FIG. 11. Jetting length as a function of capillary number for various angles of the T-junction showing transition from squeezing to jetting regimes.

FIG. 11 shows dependence of intact jet length as a function of capillary numbers for various T-junction angles. Transition between the two regimes was characterized by intact jet length (the length from the dispersed nozzle to the jet end) measured at different Ca numbers. Below critical Ca number, no liquid jet was observed that corresponds to squeezing regime. Beyond critical Ca, the jet appears and its length increases with Ca. It can be seen from the plot that critical capillary numbers increase with $\theta$. Hence, the droplet generation regime is more likely to be squeezing rather than jetting for a given flow ratio at larger $\theta$.

Figure 10A:
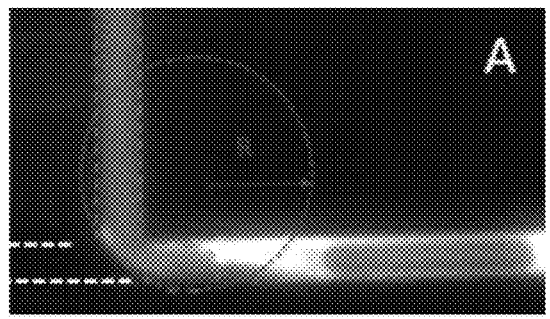
FIGS. 10A-10D. Fitted filling radius R of the water-oil interface within T-junctions of different intersection angles θ.
Figure 10B:
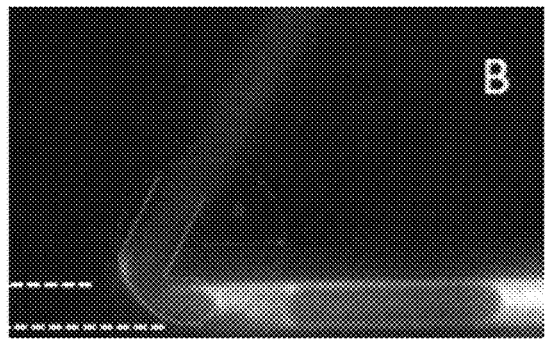
Figure 10C:
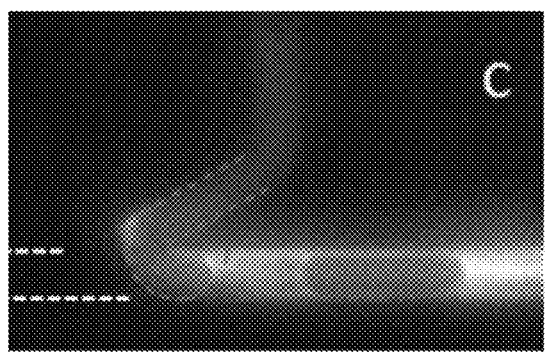
Figure 10D:
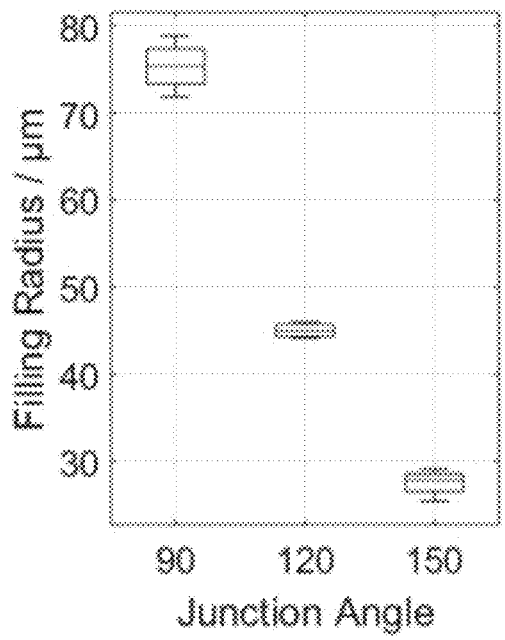
Figure 12A:
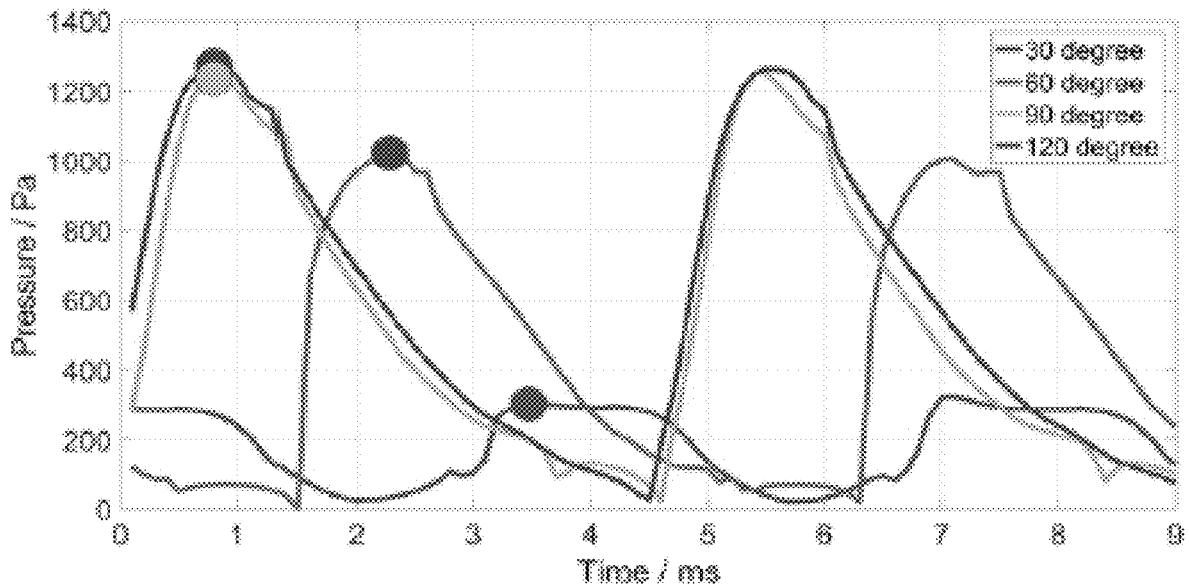
FIG. 12A: Plot of the differential pressure $\Delta P = P_{water} - P_{oil}$ at the T-junction as a function of time during droplet formation in a squeezing regime for several T-junction angles. The dots denote the maximum ΔP in the corresponding cycle.
Figure 12B:
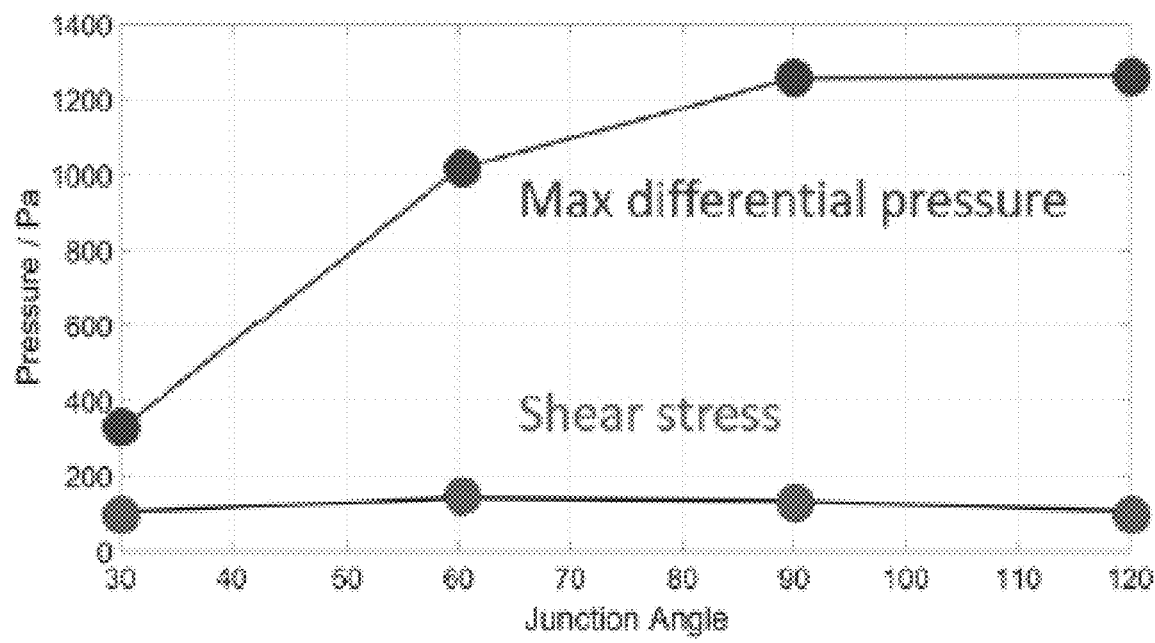
FIG. 12B: Plot of the maximum differential pressure versus shear stress during droplet formation for various T-junction angles.

This observation can be explained by consideration of the relative magnitude between viscous stress and maximum differential pressure as a function of angle $\theta$. As shown in FIG. 10D, larger $\theta$ results in smaller radius of curvature of the water-oil interface at the junction, which in turn leads to higher Laplace pressure (interfacial tension), determined by the Young-Laplace equation [11] given as:

$$\Delta P \sim \gamma \frac{2}{R}, \quad (4)$$

where R is the principal radii of curvature and $\gamma$ is the surface tension. Finite element analysis based on model of FIG. 5 verified that, in squeezing regime, the maximum differential pressure between two phases $\Delta P = P_{water} - P_{oil}$ at the T-junction increases with increasing junction angle, as illustrated in FIG. 12A. Correspondingly, at larger angles, we found that viscous shear stress is smaller than $\Delta P$, as seen in FIG. 12B. Since $\Delta P$ is equal to interfacial tension forces at equilibrium, this implies that viscous stress is less likely to overcome interfacial tension forces at larger angles. It's known that when viscous stress overcomes interfacial tension forces, the transition from squeezing to jetting regimes is initiated [12]. The viscous stress is dominated by interfacial tension at larger junction angles, and therefore the squeezing regime is preferred over jetting.

Conclusion: We demonstrate generation of monodisperse droplets with volume controllable within 1-20 pL volume range in silicon channels fabricated by $XeF_2$ etching of Si through μm-size holes in overcladding $SiO_2$ layer. Further, we found the generation process is modulated by T-junction angle ($\theta$). We found that larger $\theta$ results in larger droplet volume generated at given ratio of flow rates. The underlying mechanism is related to the droplet shape set by the junction geometry. As the filling radius is decreasing with increasing θ, squeezing time becomes longer. We also observed that there exists a critical capillary number, above which transition from squeezing to jetting regimes occurs. Such critical capillary number is found to increase with θ, i.e. the droplet generation regime is more likely to be squeezing rather than jetting for a given flow ratio at larger θ. Increase of θ results in higher Laplace pressure (interfacial tension), making viscous stress less likely to overcome interfacial tension forces for transition from squeezing to jetting regimes.

Integration of such angled T-junction into the neural probes outlined in Example 1 with efficient packaging provide a nanofluidic neural probe with potentially unprecedented spatial and temporal resolution.

REFERENCES FOR EXAMPLE 2

[1] Croushore, Callie A., and Jonathan V. Sweedler. "Microfluidic systems for studying neurotransmitters and neurotransmission." Lab on a Chip 13.9 (2013):1666-1676.
[2] Westerink, B. H.; Cremers, T. I. Handbook of microdialysis: methods, applications and perspectives; Elsevier, 2007; Vol. 16.
[3] Aris, Rutherford. "On the dispersion of a solute in a fluid flowing through a tube." Proceedings of the Royal Society of London. Series A. Mathematical and Physical Sciences 235.1200 (1956): 67-77.
[4] Zhu, Pingan, and Liqiu Wang. "Passive and active droplet generation with microfluidics: a review." Lab on a Chip 17.1 (2017): 34-75.
[5] T. Thorsen, R. W. Roberts, F. H. Arnold and S. R. Quake, Phys. Rev. Lett., 2001, 86, 4163.
[6] Bashir, Shazia, Julia M. Rees, and William B. Zimmerman. "Simulations of microfluidic droplet formation using the two-phase level set method." Chemical Engineering Science 66.20 (2011): 4733-4741.
[7] van Steijn, Volkert, Chris R. Kleijn, and Michiel T. Kreutzer. "Predictive model for the size of bubbles and droplets created in microfluidic T-junctions." Lab on a Chip 10.19 (2010): 2513-2518.
[8] Garstecki, Piotr, et al. "Formation of droplets and bubbles in a microfluidic T-junction—scaling and mechanism of break-up." Lab on a Chip 6.3 (2006):437-446.
[9] De Menech, M., et al. "Transition from squeezing to dripping in a microfluidic T-shaped junction." Journal of fluid mechanics 595 (2008): 141-161.
[10] Cubaud, Thomas, and Thomas G. Mason. "Capillary threads and viscous droplets in square microchannels." Physics of Fluids 20.5 (2008): 053302.
[11] Utada, Andrew S., Alberto Fernandez-Nieves, Howard A. Stone, and David A. Weitz. "Dripping to jetting transitions in coflowing liquid streams." Physical review letters 99, no. 9 (2007): 094502.
[12] Ferri, James K., et al. "Elastic nanomembrane metrology at fluid-fluid interfaces using axisymmetric drop shape analysis with anisotropic surface tensions: deviations from Young-Laplace equation." Soft Matter 8.40 (2012): 10352-10359.

Example 3: Neurochemical Nanodialysis Probe and Method of Fabrication

Also provided herein is a nanodialysis neural probe configured to: (i) extract analytes into picoliters (pL) of extracellular fluids (ECF) from a live brain tissue at high temporal and spatial resolution; (2) store the ECF; and then (3) directly transfer the stored ECF to a mass-spectrometer (MS) for analysis. Of course, any of a range of biological fluids can be sampled with the probes provided herein, particularly as the probe cross-section is so small that implantation can occur for a variety of tissues and organs without adverse unwanted injury and immune response. For example, the tissue can correspond to heart, lung, skin, kidney, bladder, liver, etc. with chemicals associated with extracellular fluid for those organs collected and analyzed. In other words, the probes and method are useful as a general platform for in vivo sampling of analytes or chemicals of interest.

Provided herein is a single chip silicon neural probe that can in-vivo sample analytes (e.g., chemicals), store them, and then directly deploy them for analysis. Other conventional neural probes cannot store and deploy these biological samples, which reduces the ability of those probes to provide reliable and sensitive temporal resolution of the samples. The probes provided herein are able to collect samples having low-concentration analytes, including pL sized samples, with high temporal and spatial resolution. Applications include collecting and analyzing analytes associated with the brain.

Figure 13:
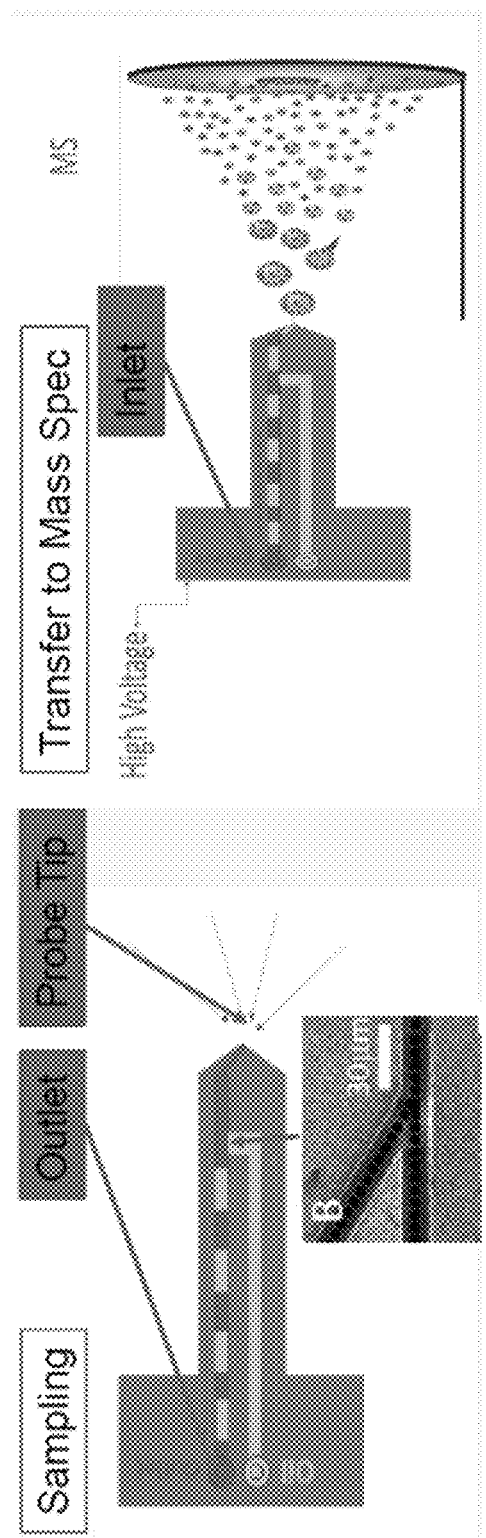
FIG. 13. Schematic illustration of a probe direct sampling a sample by application of a negative pressure at the outlet to draw in sample at the probe tip (left panel) or for analysis by application of a positive pressure at the outlet (e.g., functionally acting as an inlet, as labelled) and ejection of ionized droplets introduced to a mass spectrometer (right panel).

During sampling: a negative pressure is applied at outlet, which pulls the chemicals from the brain into the channels embedded at the probe distal tip (FIG. 13). The immiscible fluid (e.g., oil) at the T-junction segments the entering chemicals at a specific angle, so each separated droplet containing chemicals has high temporal resolution. During transfer, the previous outlet is used as an inlet to push the droplets back towards the probe tip. The probe tip then serves as an electrospray emitter: high voltage is applied to the wide base of the probe, ionizing the droplets before they are transferred to the mass spectrometry analysis.

Figure 14:
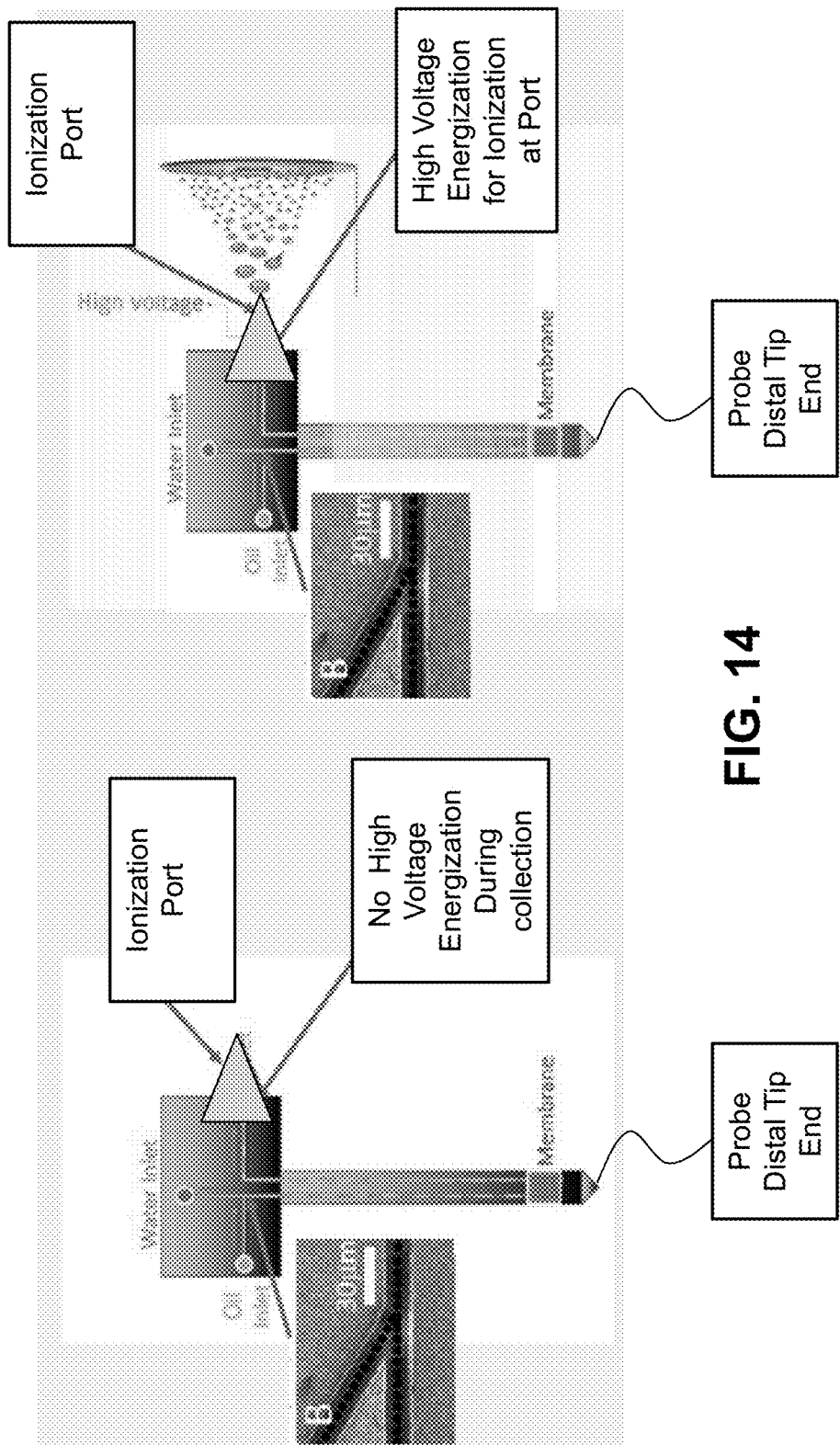
FIG. 14. Illustration of a probe using reverse flow to direct sample droplets to a separate ionization port, rather than the sample channels located at distal end of the probe (probe tip) of FIG. 13. In this manner, other sampling modes are achieved, including membrane dialysis.

Alternatively, in another embodiment, the reverse flow may direct the sample droplets to a separate electrospray ionization port rather than to the probe distal tip end (FIG. 14). This allows using other sampling methods such as membrane dialysis by incorporation of a membrane into the microfluidic channel.

Example 4: Fabrication Methods

Figure 6:
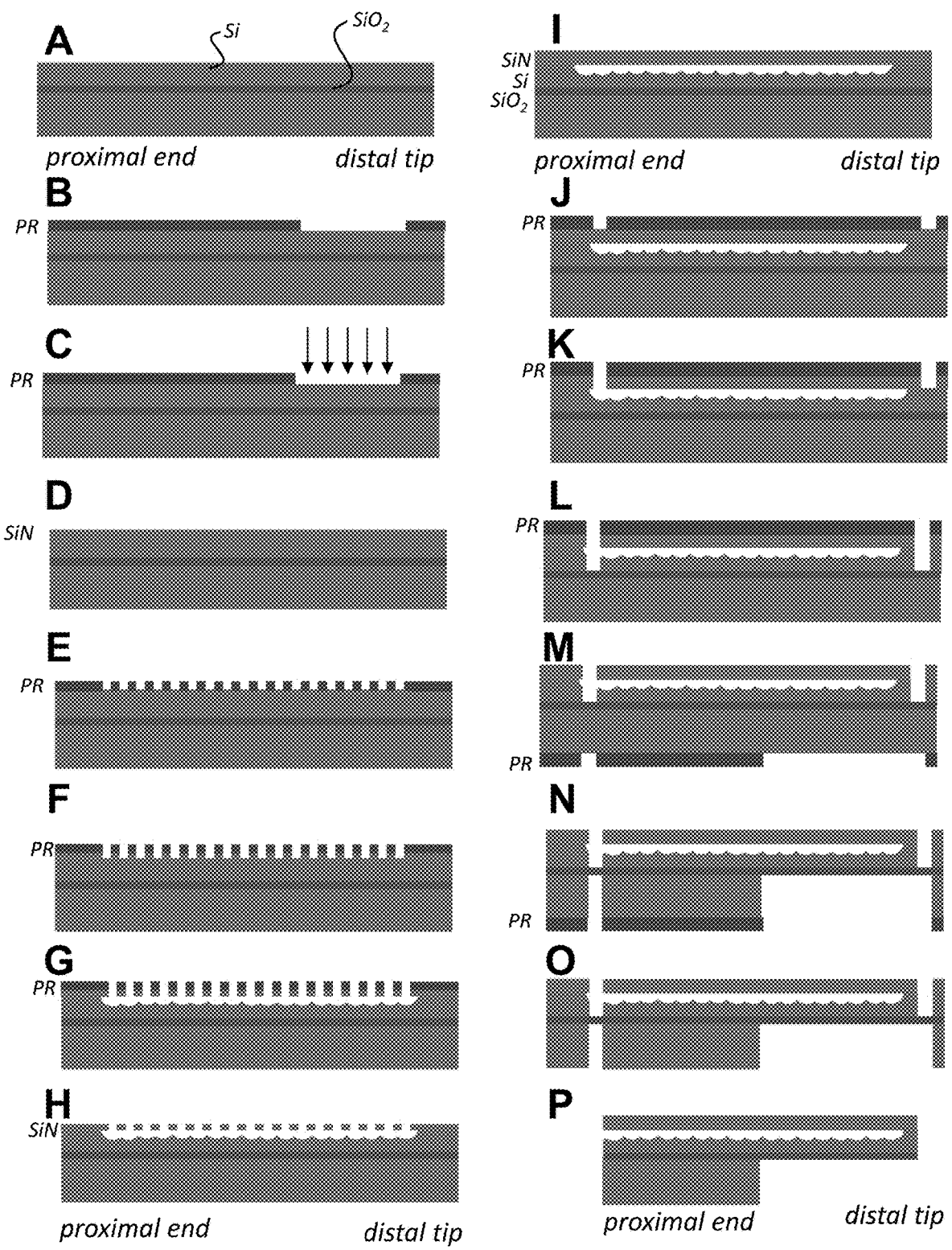
FIG. 6 (and corresponding panels A-P thereof) is another fabrication process flow for silicon nanofluidic channels. (A) Double-sided polished silicon or silicon on insulator (SOI) wafer with silicon device layer thickness less than or equal to 20 µm that is either heavily doped or undoped; (B) SOI wafer is spin-coated with photoresist (PR) on the top silicon device layer; (C) PR is patterned to provide an opening in the distal end of the probe body for doping; (D) Doping is provided through the PR opening to form a highly conductive silicon device layer with a sheet resistance less than or equal to 0.1 Ohm*cm for further energizing the electrospray emitter port; (E) the PR layer is tripped and the SOI wafer is oxidized or oxide (i.e. silicon oxide $SiO_2$ or silicon nitride SiN) is deposited to top device side of the SOI wafer, (E) PR layer is deposited and patterned with a series of round openings having less or equal to 1 mm diameter arranged in lines with separation distance less or equal to 10 µm to expose a mask pattern for formation of microfluidic interconnected channels; (F) Directional etching (i. e. by ICP-RIE) of oxide mask down to silicon device layer, (G) isotropic etching of silicon device layer through the oxide mask to the depth of less than the device layer thickness that enables nearby holes in silicon device layer to merge laterally into a continuous microfluidic channel, (H) PR stripping, (I) deposition of a layer of silicon oxide or silicon nitride of less than or equal to 5 mm thickness to overgrow the round openings in the mask layer, (J) Deposition of PR and its patterning on top-side silicon SOI wafer by lithography as the hard mask to define the probe perimeter, (K) Directional etching of oxide top layer (i.e. by ICP-RIE), (L) Directional etching of the silicon device layer down to the buried oxide (BOX) layer to define the device perimeter, (M) Stripping of the top-side PR, deposition of the bottom side PR layer and photolithography of the bottom side PR layer to define the proximal end perimeter, the distal end perimeter, and the electrospray port perimeter, (N) directional etching of the backside handle of SOI wafer to expose BOX layer to isolate the proximal end perimeter, to undercut the distal end perimeter, and to undercut the electrospray port perimeter from the rest of the wafer; (0) stripping of PR, (P) device release from wafer and packaging.
Figure 15A:
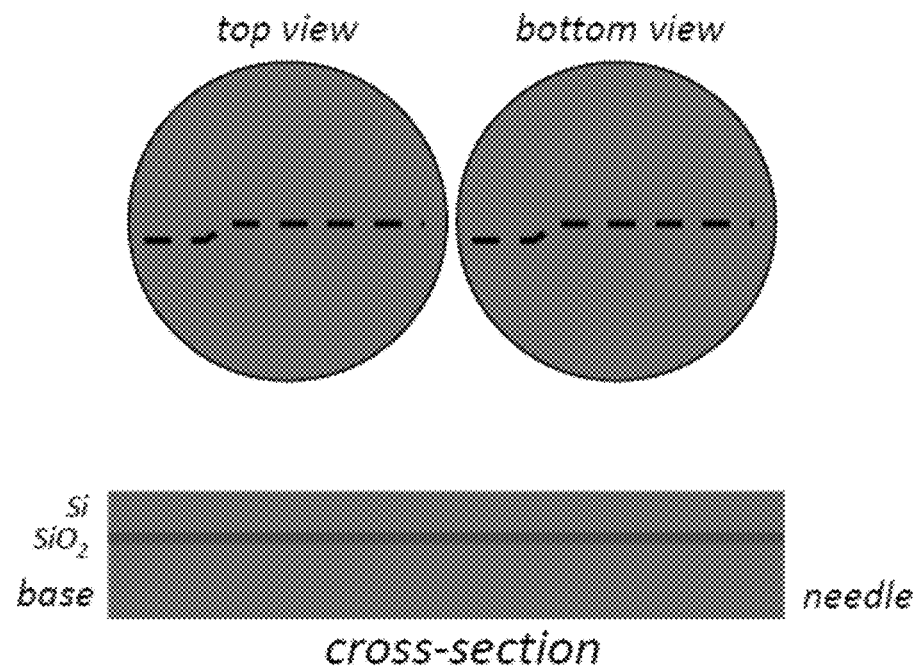
FIGS. 15A-15R corresponds to various steps of FIG. 6 used in a method of making a probe.
Figure 15B:
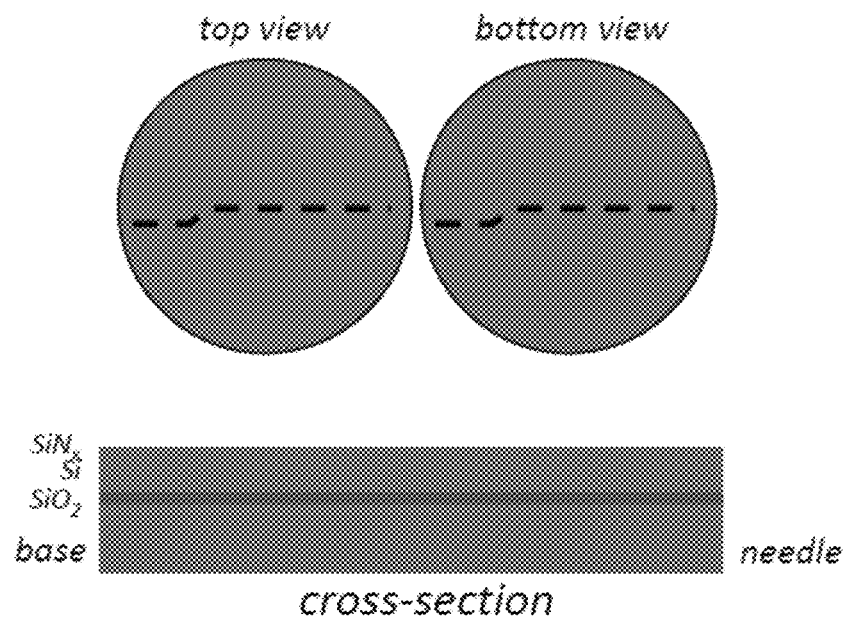
Figure 15C:
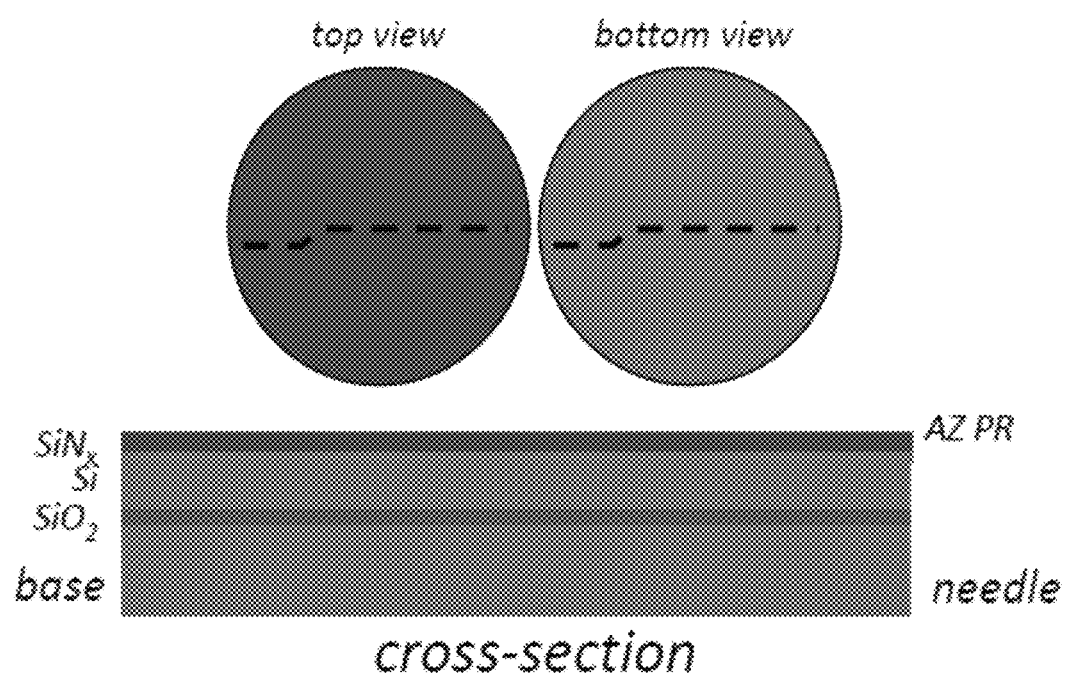
Figure 15D:
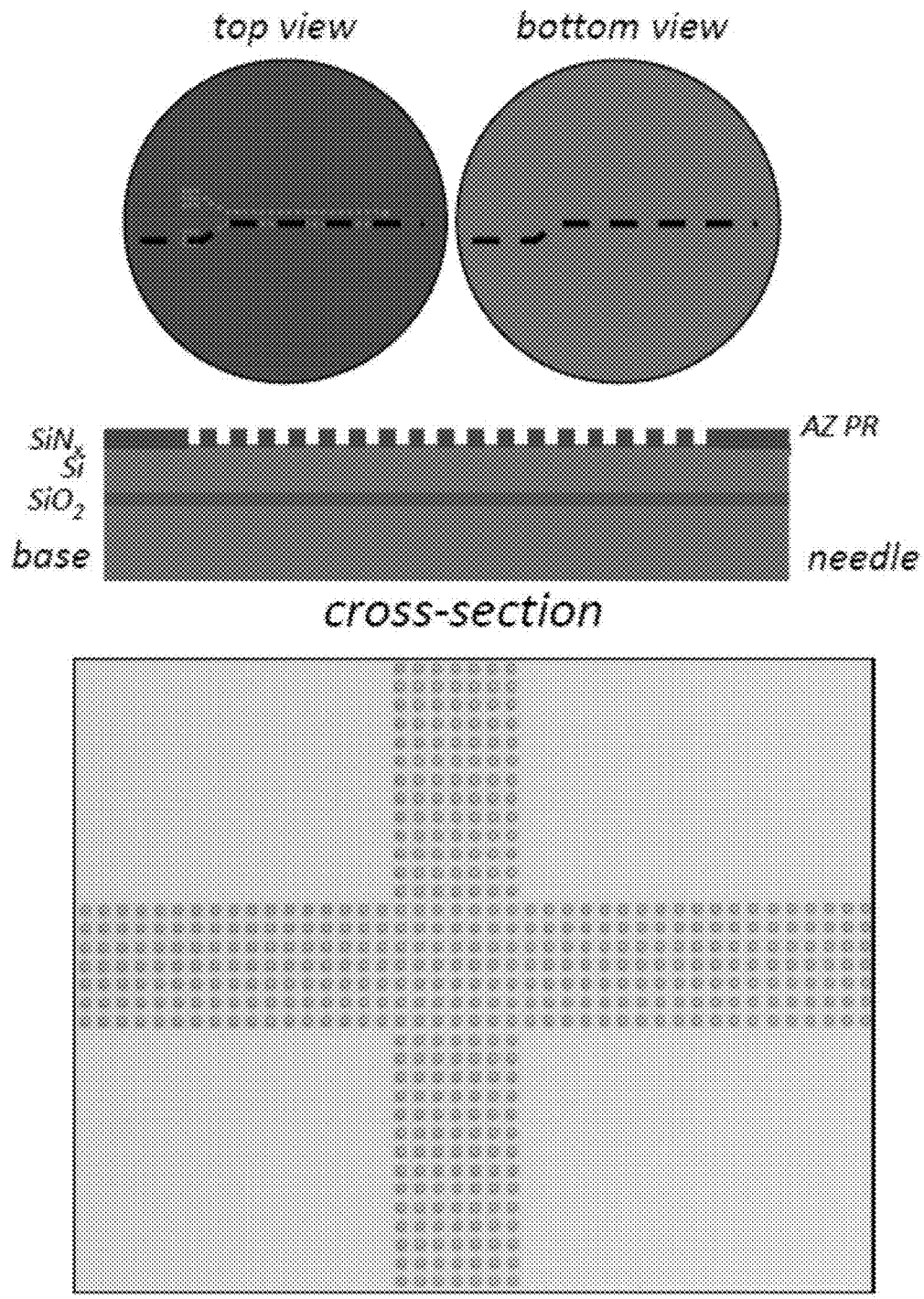
Figure 15E:
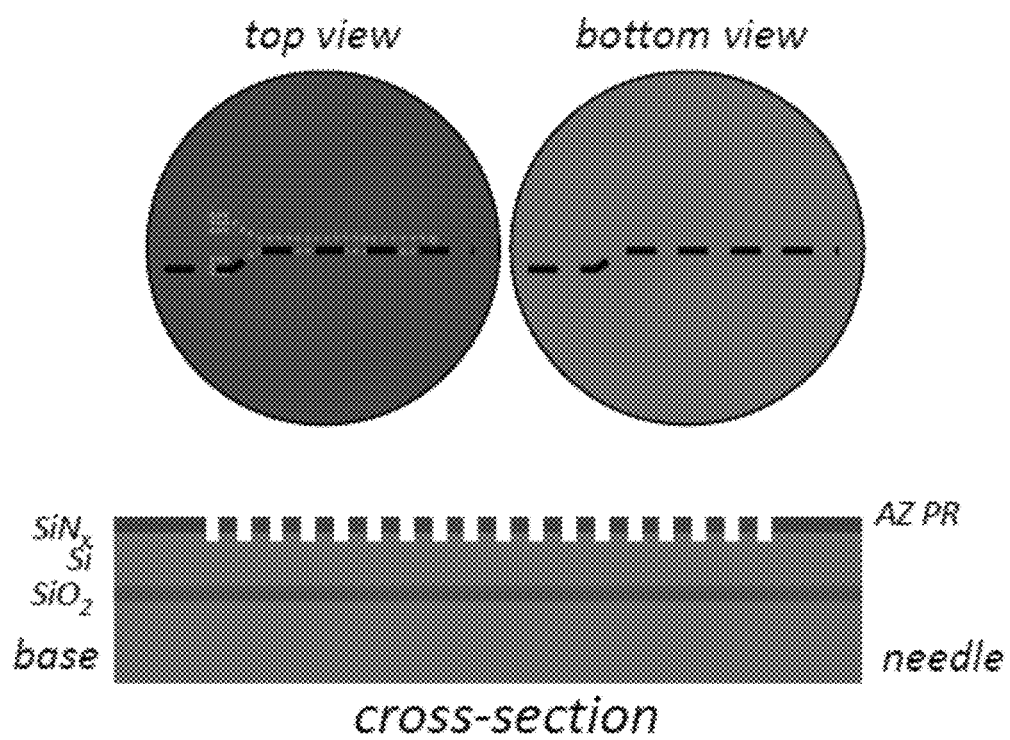
Figure 15F:
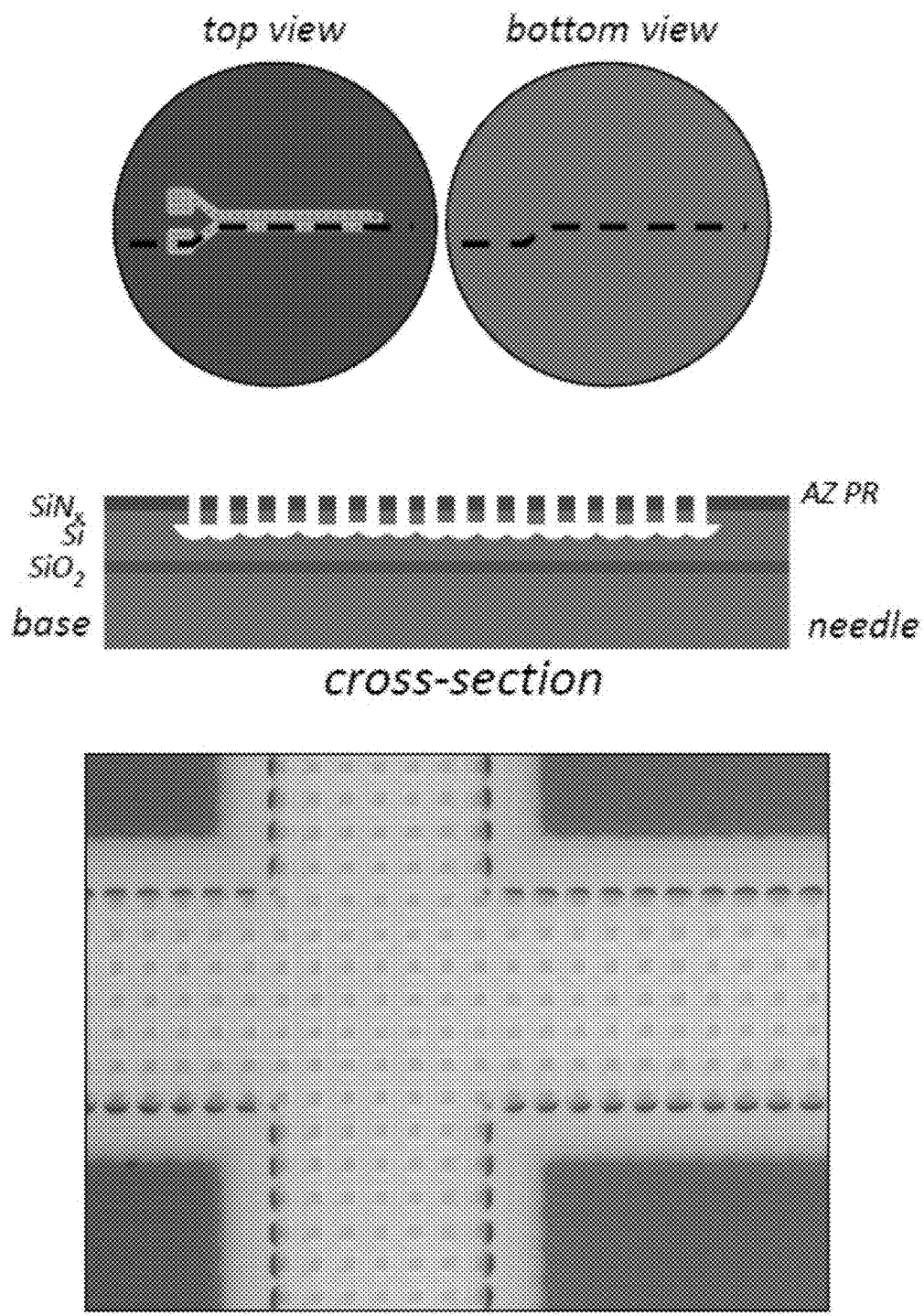
Figure 15G:
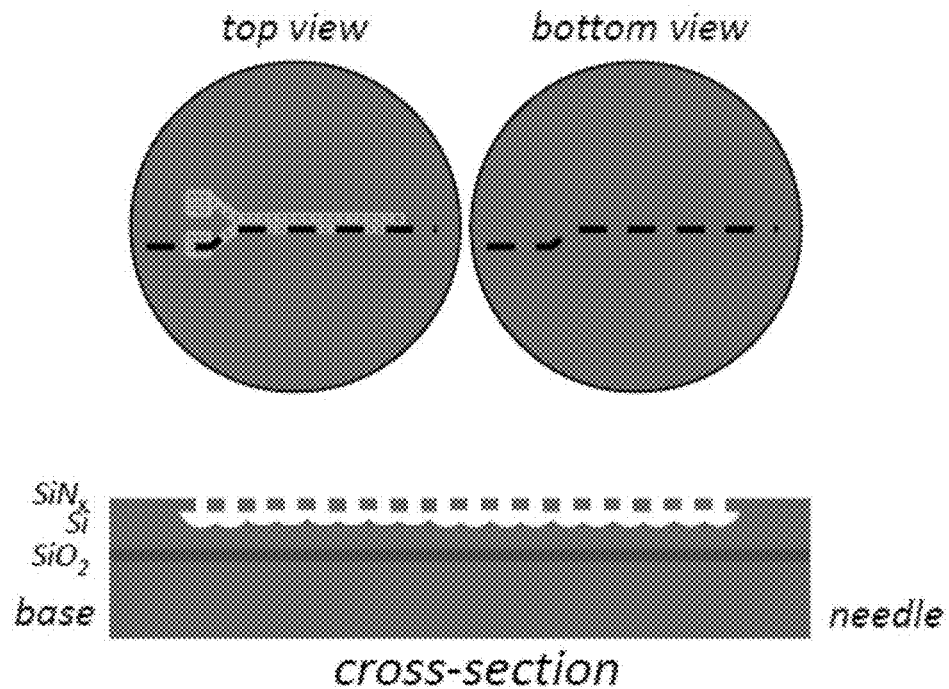
Figure 15H:
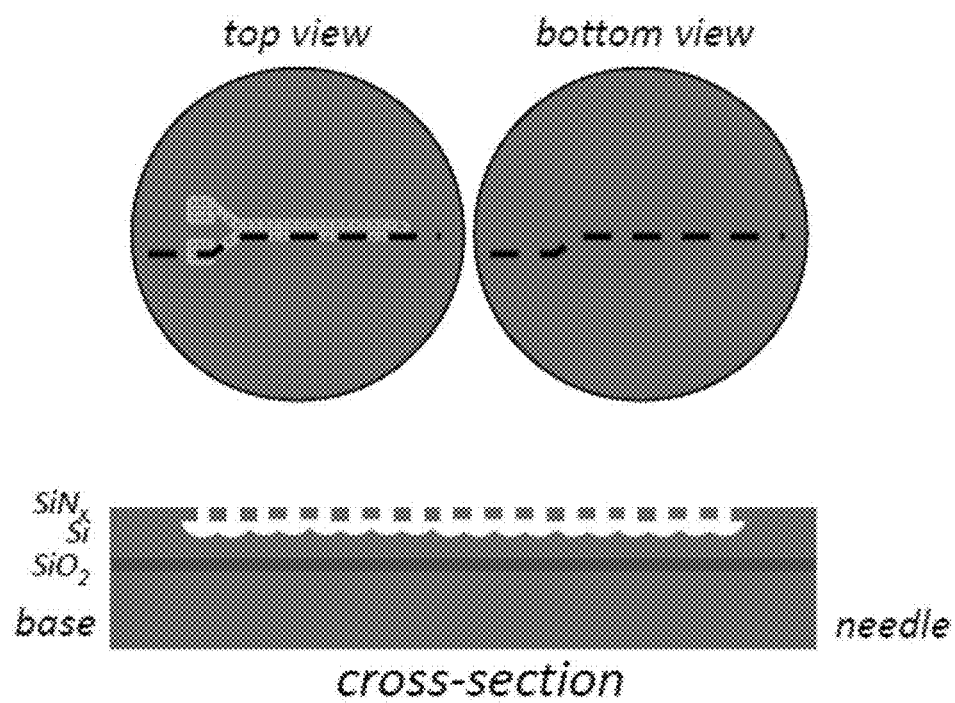
Figure 15I:
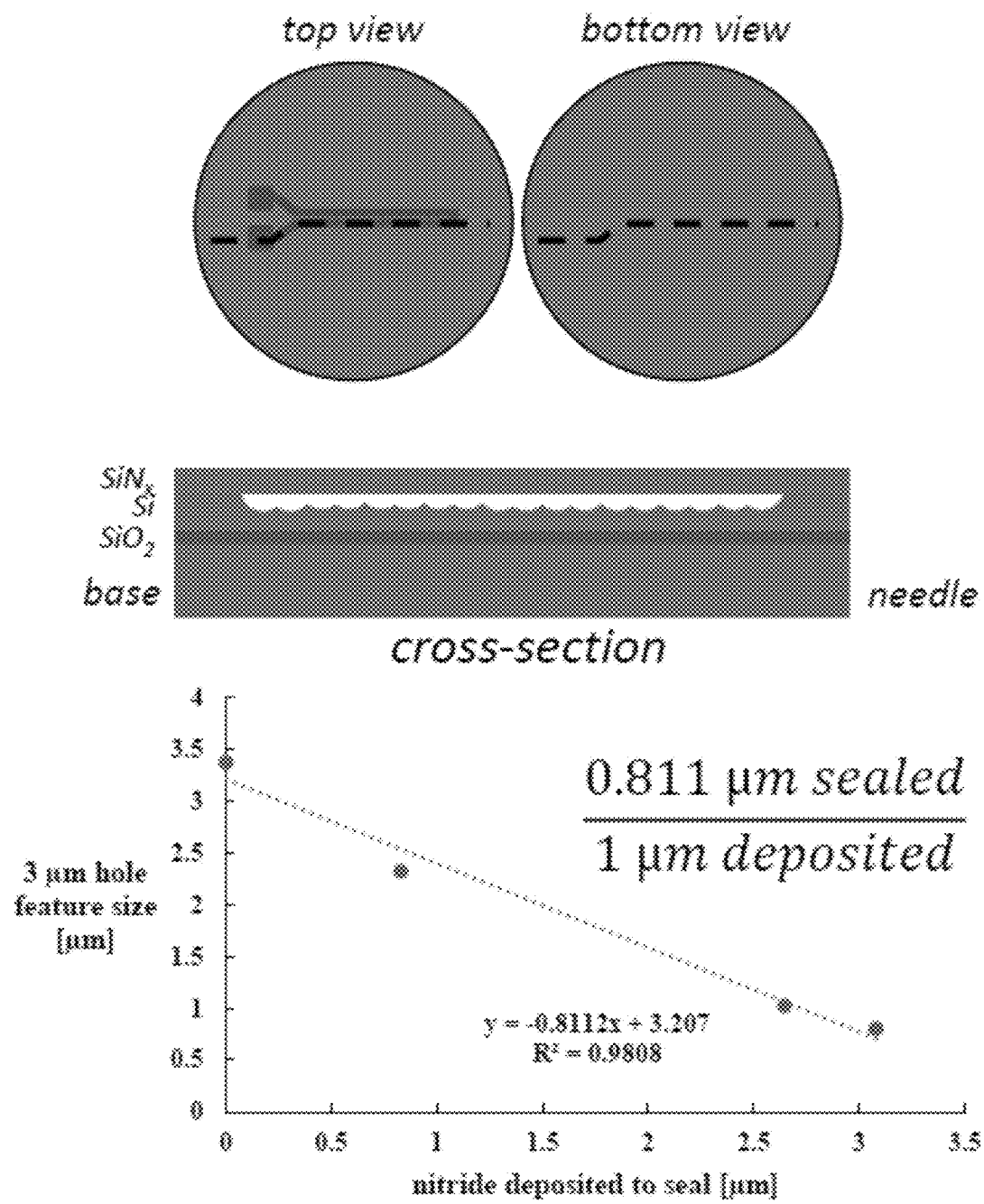
Figure 15J:
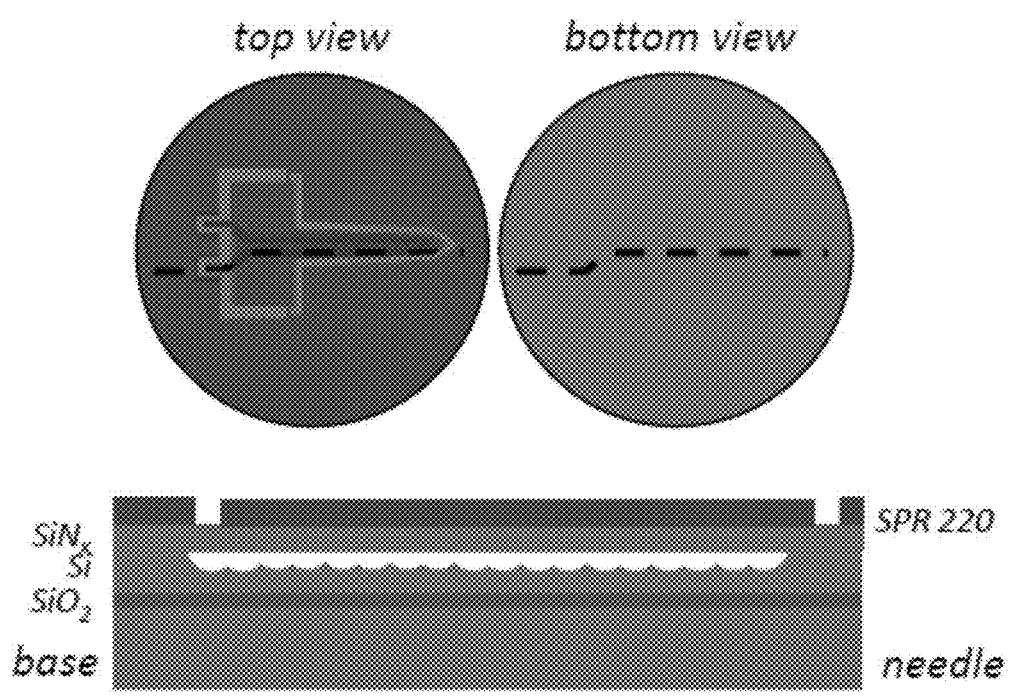
Figure 15K:
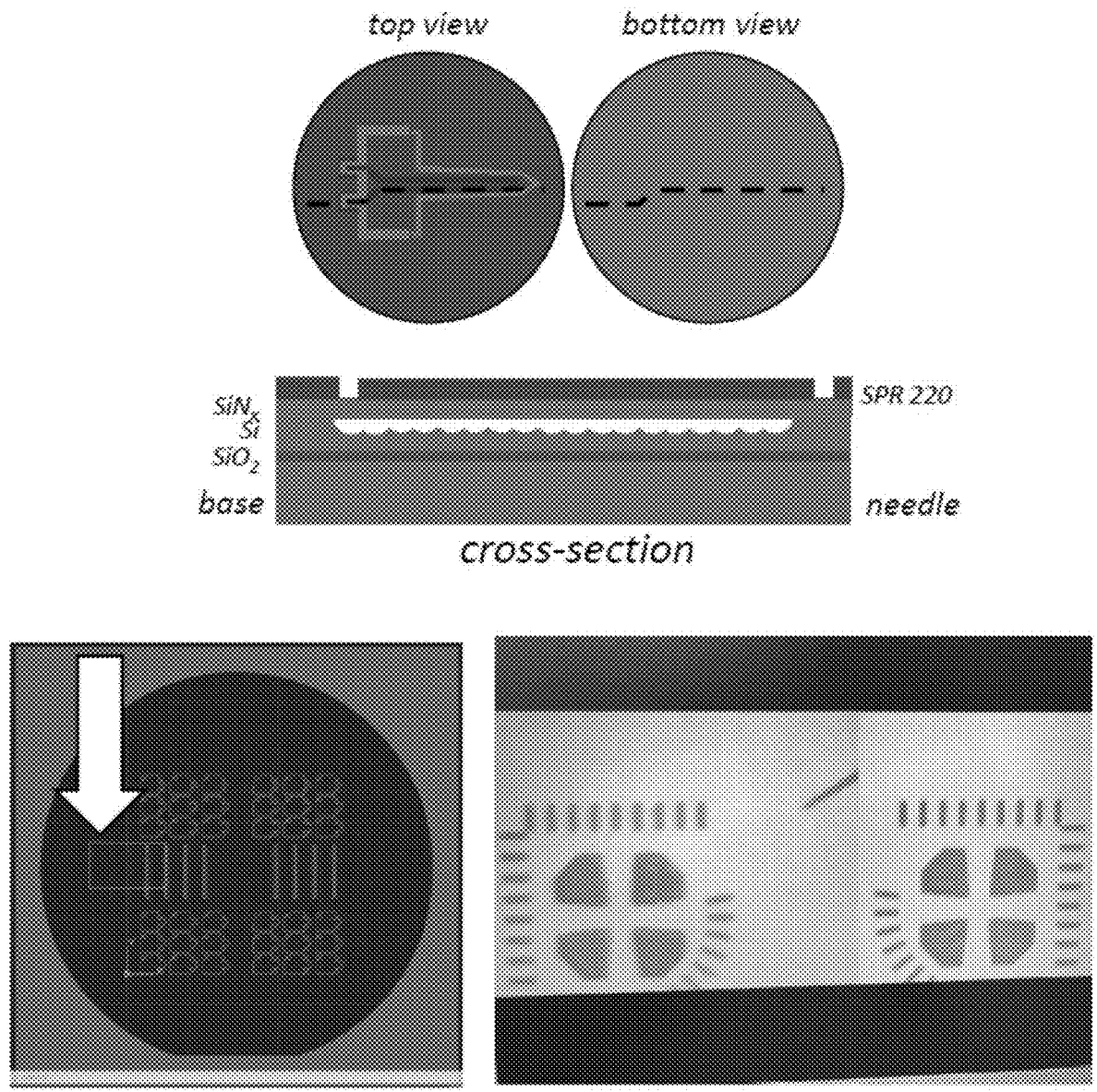
Figure 15L:
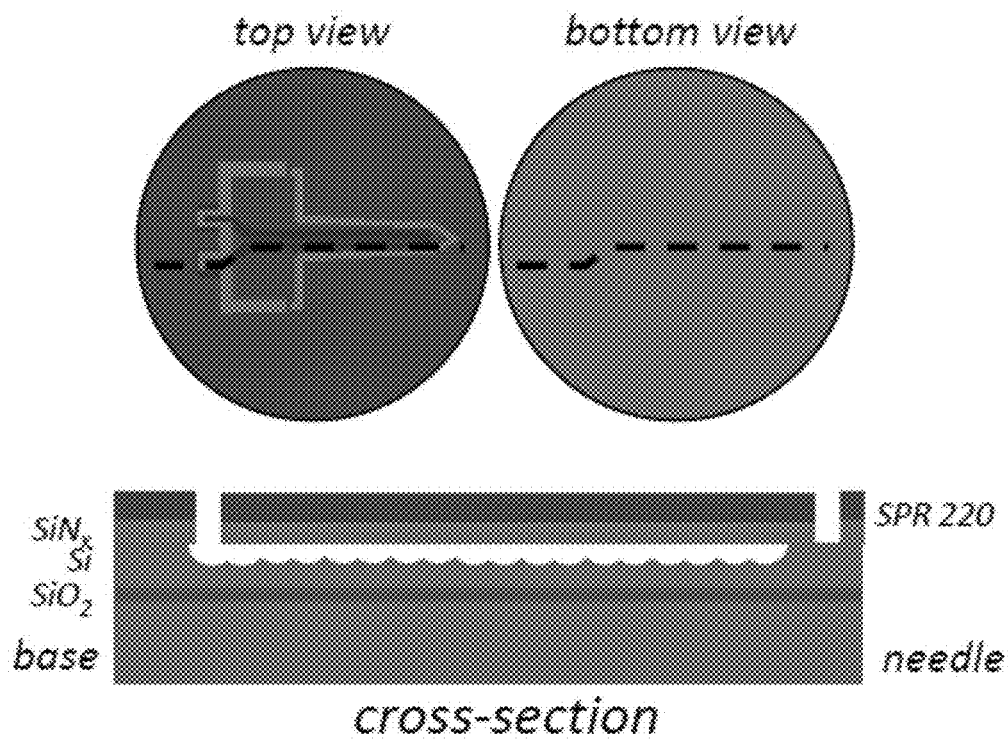

Also provided are methods of fabricating any of the probes and probe bodies described herein, including an implantable neural probe for in-vivo sampling of biological fluids (FIGS. 6 and 15A-15S). An exemplary fabrication method includes any one or more of the following steps:

Step 0: Materials Required (FIG. 15A)
1. Substrate: silicon-on-insulator (SOI) wafer with the following dimensions: 1. Dev: 5-30 µm, buried oxide layer BOX: 1-2 µm, Handle silicon wafer: >300 µm Step 1: Deposit $SiN_x$ hard mask (FIG. 15B)
Tool
STS PECVD
Recipe
1. Degrease/descum SOI wafer if needed (if fresh out cassette, just blow dust with $N_2$)
    Degrease: (Acetone, IPA, DI water, IPA, $N_2$ dry)
    Descum: Jupiter RIE 2:1 $O_2$:Ar plasma for 1 minute at 100 W
2. Dehydration bake, then cool wafer
    @ 110° C. for 2 [min]
3. Load wafer into STS PECVD
4. Deposit ~350 nm of $SiN_x$ using the low-stress mixed frequency recipe Step 2: Applying Photoresist (PR) for Channels (FIG. 15C)
Tool
Headway Spinner
HMDS vapor deposition tool
Recipe
1. Degrease/descum wafer
   Degrease: (Acetone, IPA, DI water, IPA, N$_2$ dry)
   Descum: Jupiter RIE, 2:1 O2:Ar plasma for 1 minute at 100 W
2. Dehydration bake, then cool wafer
   @ 110° C. for 2 [min]
3. Center wafer on spinner chuck and run the recipe to remove small particles from the wafer surface
4. Apply HMDS for adhesion promotion using the vapor deposition tool
5. Apply PR (typically 3 [mL]) onto the wafer
6. Spin-coat PR
   PR:
   AZ1512: {500, 5000, 2|5000, 5000, 20}
   AZ1505: {1000, 3000, 5|4000, 3000, 30}
7. Soft-Bake, then cool wafer
   AZ1512: 110° C. for 1 [min]
   AZ1505: 100° C. for 1 [min]
Step 3: Channel Photolithography (PL) (FIG. 15D)
Tool
Heidelberg pPG101
Recipe
1. Start exposure
   AZ1512: −11 foc, 1 mWat 100%
   AZ1505: −9 foc, 1.3 mWat 100%
3. Immerse wafer in developer
   AZ1512: 2 [min] in AZ 1:1 Developer
   AZ1505: 1 [min] in AZ 400K 1:4
4. DI Rinse; N$_2$ Dry
Notes
A 50-× optical image is illustrated in the bottom panel of FIG. 15D. False color, illustrating about 112 μm×84 μm, after development, before etching. AZ1512 PR, 1 mW dose.
Step 4: Etch SiNx (FIG. 15E)
Tool: —Oxford Freon ICP RIE (MNTL)
Recipe
1. Clean the back surface of the wafer with acetone and IPA until no particles can be observed
2. SiNx Low (etch rate ~180 nm/min)
Notes
Over-etch here to ensure residual PR is gone from the channel hole sites, and that the device side Si is exposed. E.g. for ~350 nm, etch for 600 nm.
Step 5: Etch Si to Define Channels (FIG. 15F)
Tool
Xactix XeF2 Etcher
Recipe
Number of cycles: 2
Etch time per cycle: 60 [s]
Pressure: 3 [T]
Temperature: 25 [° C.]
Notes
The bottom panel is a 100× optical image with false color and dimensions of about 56 μm×42 μm after 1 cycle XeF$_2$, AZ1512 PR, 1 mW dose.
Step 6: Strip Photoresist (FIG. 15G)
Tool
Wet Lab Hotplate
Any solvent hood
Recipe 1. Agitate wafer in AZ400T PR Stripper @ 90 [° C.] for 10 [min]
2. Optional sonicate wafer in IPA @ 25 [° C.] for 5 [min]
3. DI Rinse @ least 1 minute; N$_2$ Dry
4. Dehydration bake @ 110 [° C.] for 1 [min]
Notes
Membrane Deposition (FIG. 15H)
Tool—Wet Lab Hotplate
Recipe
1. Agitate wafer in AZ400T PR Stripper @ 90 [° C.] for 10 [min]
2. Sonicate wafer in IPA @ 25 [° C.] for 5 [min]
3. DI Rinse; N$_2$ Dry
4. Dehydration bake @ 110 [° C.] for 1 [min]
Notes
Step 7: Seal channels with SiN$_x$ (FIG. 15I)
Tool—STS PECVD (MNTL)
Recipe
1. Degrease SOI wafer
   (Acetone, IPA, DI water, IPA, N$_2$ dry)
2. Dehydration bake, then cool wafer
   @ 110° C. for 2 [min]
3. Load wafer into STS PECVD
4. Deposit 4 μm of SiNx using the low-stress mixed frequency recipe. Approximate deposition rate of 27 nm/min, stress rated around −30±25 MPa
Step 8.1: Applying SPR220 (FIG. 15J)
Tool/Chemical
Any spinner, hotplate
SPR 220 4.5 Photoresist (plasma resistant for DRIE)
Recipe
1. Degrease/descum wafer
   Degrease: (Acetone, IPA, DI water, IPA, N$_2$ dry)
   Descum: Jupiter, 2:1 O$_2$:Ar plasma for 1 minute at 100 W
2. Deposit 3.5 mL of SPR220 4.5 onto wafer
   Optional: Deposit 8 drops of AP8000 adhesion promoter before SPR220
3. Spincoat
1. Step 1: 500 rpm speed-250 rpm/s ramp-2 s duration
2. Step 2: 1500 rpm speed-500 rpm/s ramp-2 s duration
3. Step 3: 3000 rpm speed-750 rpm/s ramp-30 s duration
4. Softbake@ 60° C. for 2 mins
5. Softbake@ 110° C. for 1 min
6. Cool for 1 min
Notes
SPR is plasma resistant, and can protect the channels from DRIE during device and handle-side etching of the probe shape.
Step 8.2: Top Side Alignment SPR220 (FIG. 15K)
Tool/Chemical
Heidelberg pPG101 for direct writing
EVG 620 for photolihtogrpahy masks
Recipe
1. Expose with EVG620 using the following parameters:
   Dose: 210 mJ/cm$^2$
   Contact: V+H
   Separation: ~20-50 μm (farther if PR is stuck to mask)
2. Develop in AZ917 MIF developer
3. DI Rinse @ least 1 minute; N$_2$ Dry
Notes
Top side alignment requires locating alignment marks in the Si sample underneath the mask.
Step 9: Etch to Si Thru SiN$_x$ (FIG. 15L)
Tool
Oxford Freon ICP RIE
Recipe 1. MNTL-Si3N4 etch 180 nm/min low
2. Time: (Thickness/nominal etching rate)*1.3

Figure 15M:
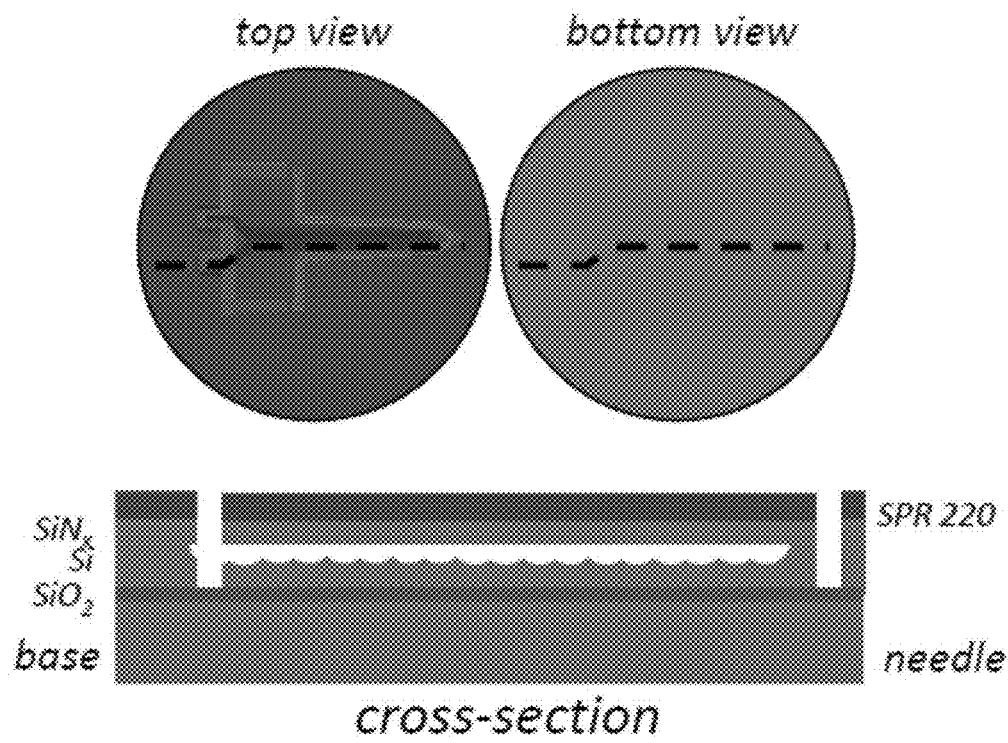
Figure 15N:
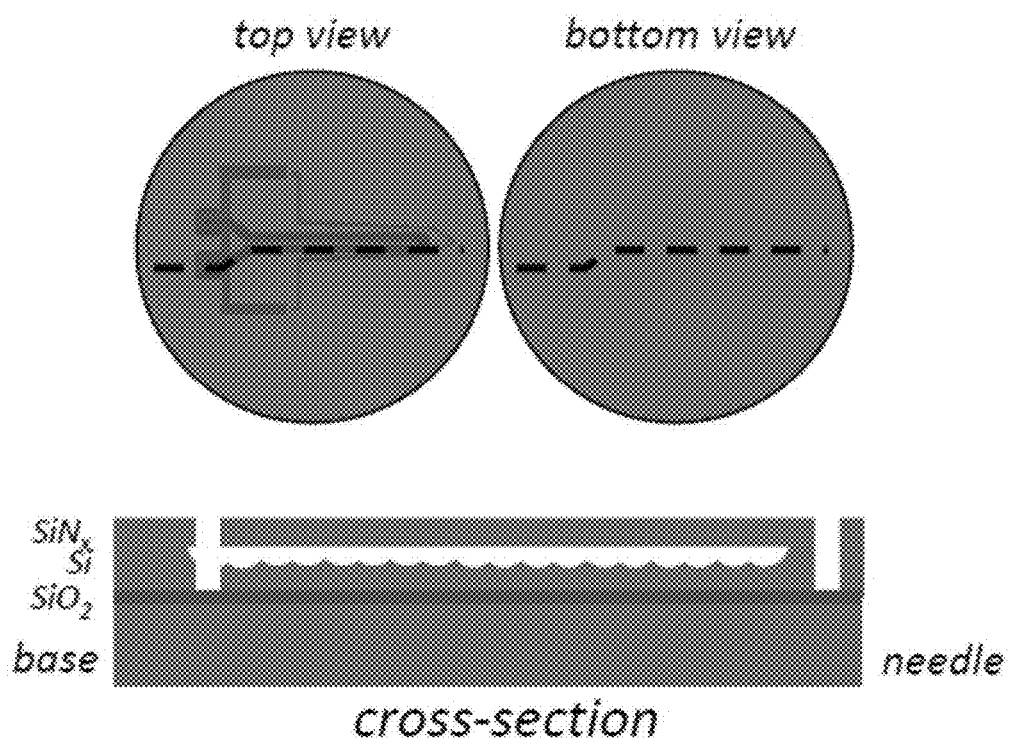
Figure 15O:
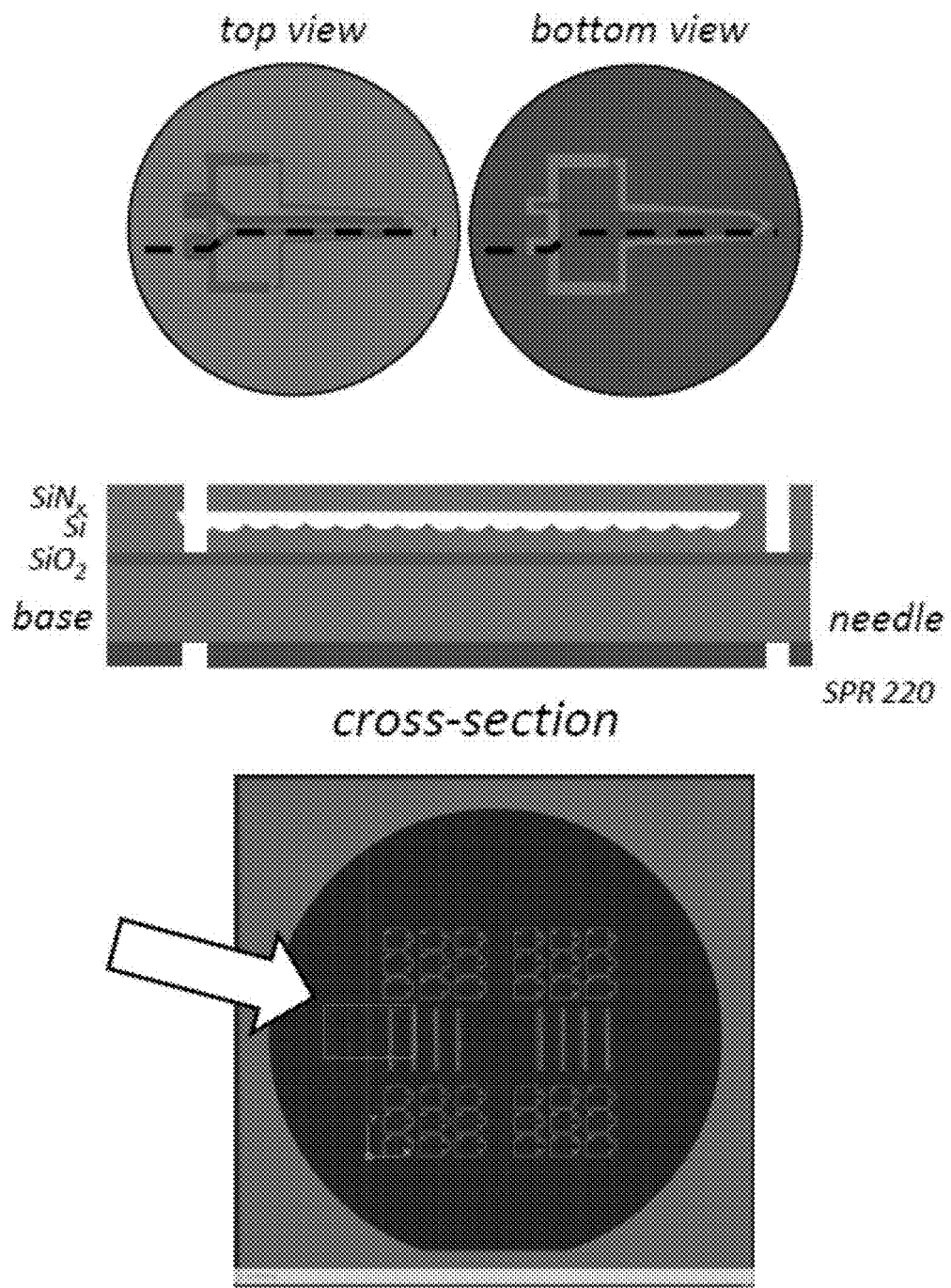
Figure 15P:
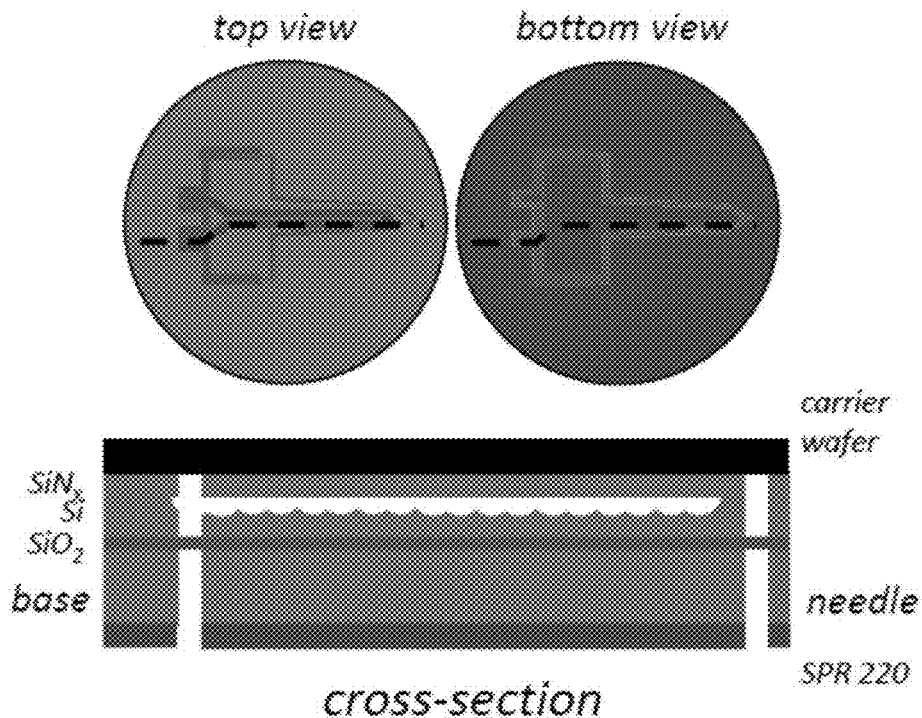
Figure 15Q:
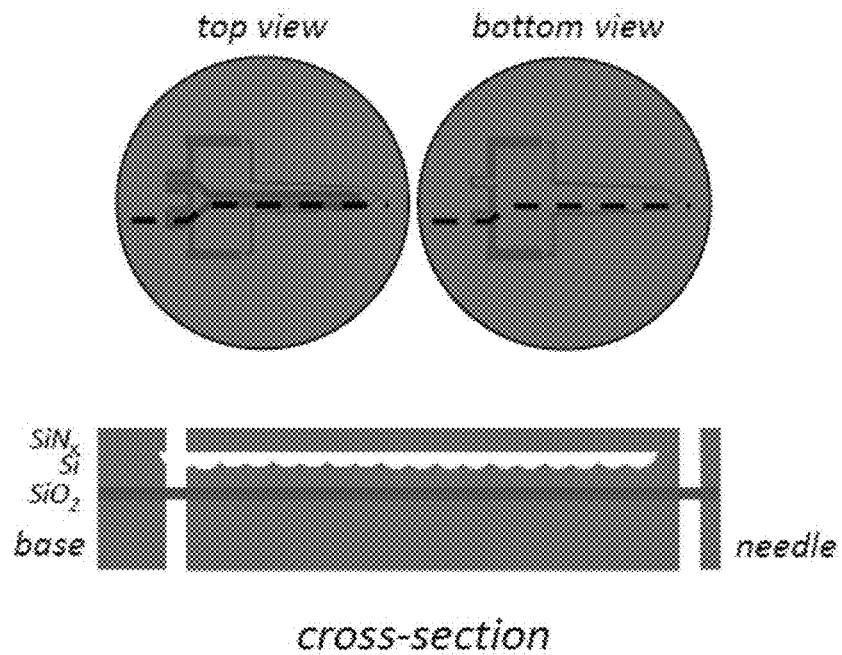

Step 10: Top DRIE (FIG. 15M)
Tool
STS Pegasus ICP-DRIE
Recipe
1. Customized to the device layer thickness:
Notes Step 11: Strip PR (FIG. 15N)
Tool
Wet Lab Hotplate
Any solvent hood
Recipe
1. Agitate wafer in AZ400T PR Stripper @ 90 [° C.] for 10 [min]
2. Sonicate wafer in IPA @ 25 [° C.] for 5 [min]
3. DI Rinse @ least 1 minute; $N_2$ Dry
4. Dehydration bake @ 110 [° C.] for 1 [min]
Notes Step 12: Backside Alignment on SPR 220 (FIG. 15O)
Tool—EVG 620 Mask Aligner
Recipe
1. Apply and expose SPR220 (see previous steps)
Notes Step 13: Bottom DRIE (FIG. 15P)
Tool—STS Pegasus ICP-DRIE (MNMS)
Notes
1. Carrier wafer is mandatory at this step Step 14: Strip RR (FIG. 15Q)
Tool—Wet Lab Hotplate
Any solvent hood
Recipe
1. Agitate wafer in AZ400T PR Stripper @ 90 [° C.] for 10 [min]
2. Sonicate wafer in IPA @ 25 [° C.] for 5 [min]
3. DI Rinse @ least 1 minute; $N_2$ Dry
4. Dehydration bake @ 110 [° C.] for 1 [min]

Figure 15R:
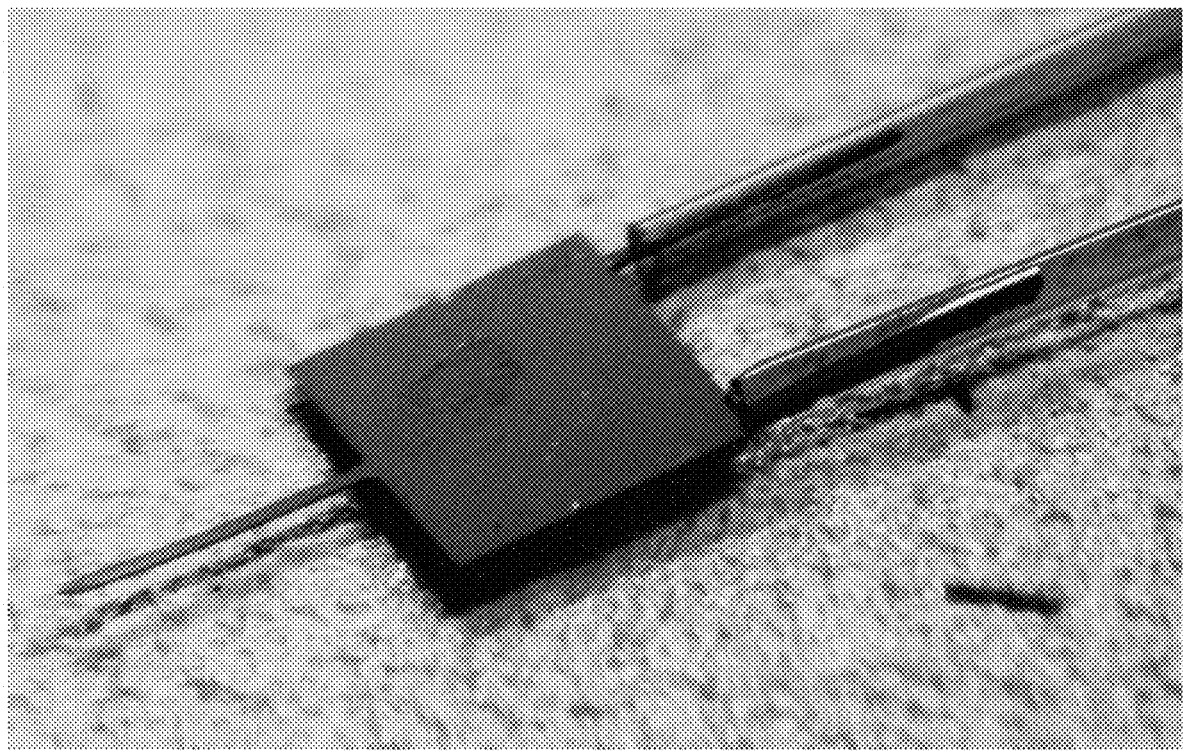
Figure 15R:
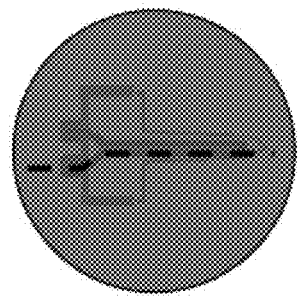
Figure 15R:
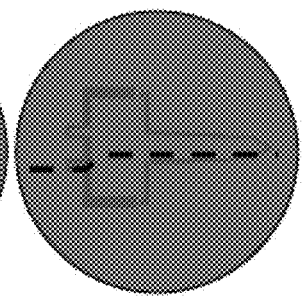
Figure 15R:

Step 15: Probe Release, Packaging and Plumbing (FIG. 15R)
1. Soak in warm water+force application. Top panel is an image of the probe released from support substrate, plumbed with pair of glass capillaries and packaged.

Probe release from the wafer is facilitated by having small bridges that connect the patterned/etched probe to the wafer. Fracture of the bridges provides for controlled release of the probe from the wafer, with the probe ready for final handling and implantation with minimal additional steps.

Example 5: Droplet-Assisted Phase Separation by Integrated Silicon Electrospray Nano-Emitter for Neurochemical Sensing We demonstrate a nano-electrospray ionization (n-ESI) emitter monolithically integrated on silicon chip. Chip contains an integrated T-junction droplet generator that enables segmentation of analytes flow in µm-scale microfluidic channels into a series of oil-isolated pL-volume aqueous droplets. Chip-integrated n-ESI emitter is designed to efficiently deliver segmented analytes for subsequent mass spectrometry (MS) analysis. Engineered emitter nozzle geometry enables spatial and temporal separation of electrosprayed oil and aqueous phases to monitor sampled neurochemicals on a droplet-by-droplet basis thus promising improved temporal and chemical sensitivity.

Development of miniaturized implantable microdialysis neural probes is essential for monitoring brain chemistry in health and disease. To improve temporal and chemical sensitivity, flow segmentation with droplet microfluidics, and hyphenation to various mass spectrometry (MS) methods have been explored [1]. However, lack of integration of various microfluidic components into a single device typically limits the achievable chemical sensitivity for a given time resolution [2]. Integration and miniaturization holds a promise to achieve ultra-slow nL/min flow rates and pL scale droplet volumes, that can help to overcome this fundamental tradeoff.

Figure 16:
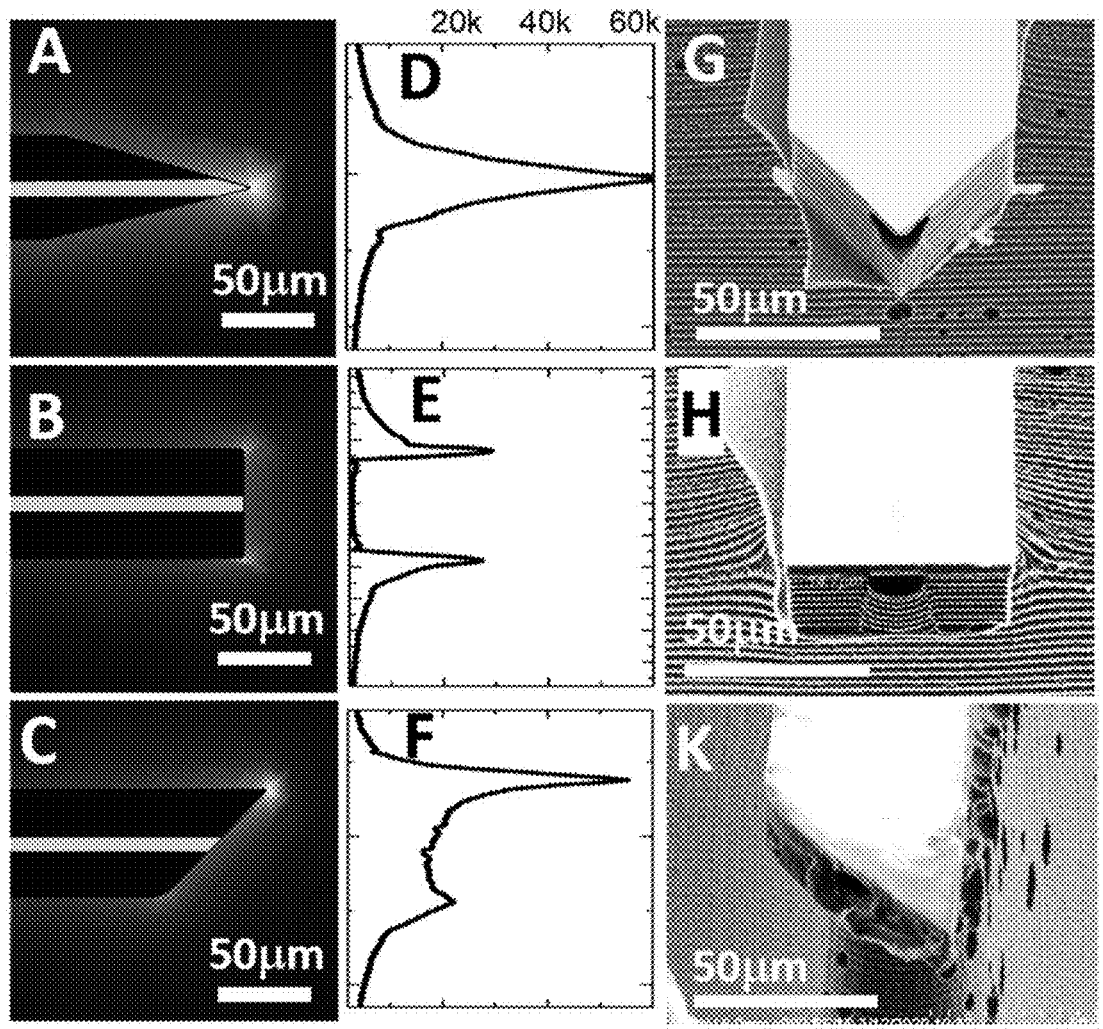
FIG. 16: Design of electrospray emitter nozzle (A-C), calculated electric field (in units of kV/cm) profiles (D-F), and SEM micrographs of fabricated suspended silicon emitters (G-K).

Design: Microfabrication of n-ESI emitters on highly-doped silicon-on-insulator (SOI) platform enables precise µm-scale control of relative positions of the concentrated electric fields and the outlet orifice of the buried microfluidic channels. FIG. 16 shows three different designs of the n-ESI emitter nozzle that explore this opportunity. First design (FIG. 16, panel A) with a sharpened nozzle tip concentrates electric field exactly at the outlet orifice of the microfluidic channel (shown by gray rectangle). Numerical modeling (FIG. 16, panels A and D) reveals formation of a single "hot spot" localized within just 25 µm at the nozzle tip with electric field strength over 60 kV/cm. Second design (FIG. 16, panels B and E) with a flat nozzle moves a pair of "hot spots" 30 µm away from the outlet orifice. However, the axial symmetry of this design results in a "hot spot" electric field strength dropped by a factor of 2. Third design (FIG. 16 panels C and F) with angled nozzle tip breaks the symmetry with a stronger "hot spot" restored to 55 kV/cm.

Figure 17A:
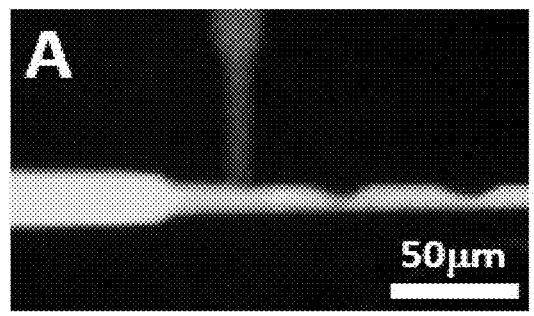
FIG. 17A: Fluorescence image of T-junction.
Figure 17B:
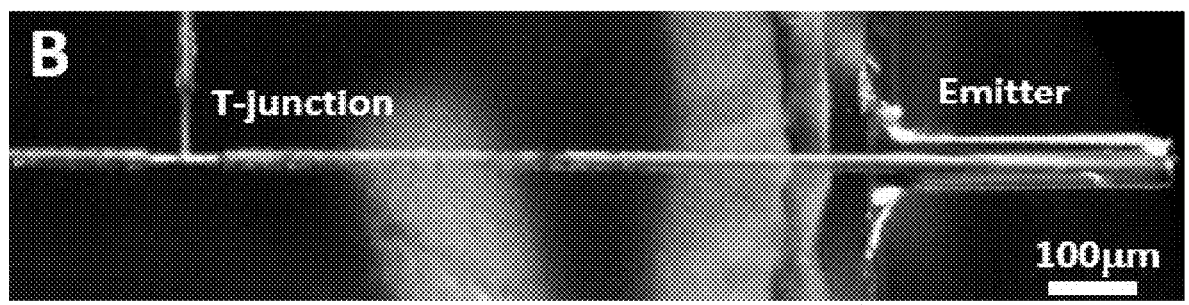
FIG. 17B: Microscope image of integrated chip.
Figure 17C:
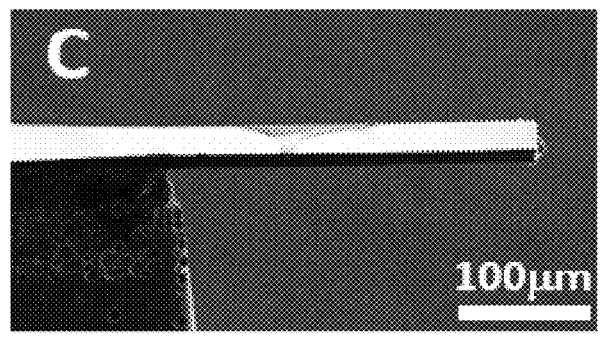
FIG. 17C: SEM image of suspended n-ESI emitter (flat end design).

Experimental: Integrated chip is fabricated on silicon-on-insulator (SOI) wafer with device layer (B-doped, 0.005 Ω-cm) with 15 µm thickness that is selected to minimize brain tissue damage during implantation. This dictates geometric scaling of buried microfluidic channels down to just 7 µm radius. Channels are formed by $XeF_2$ silicon etching through a series of µm-size holes defined by ICP RIE in deposited silicon nitride hard mask. Channels are then sealed by PECVD deposition of 4 µm-thick silicon nitride overcladding. DRIE Bosch etching through silicon substrate release suspended silicon emitters with final cross-section of just 15×60 µm² as shown in FIG. 16 panels G, H, K. A chip-integrated T-junction (FIGS. 17A and 17B) provides segmentation of aqueous phase (1 µM Fast Green FCF in DI water) into a series of 8 pL-volume plugs isolated by oil phase (Rhodamine in octanol) droplets. Droplet-segmented flow is delivered to the orifice of the n-ESI emitter (FIGS. 17B and 17C) at 5 nL/min flow rate resulting in a few Hz frequency of droplet ejection. To electrospray the segmented flow, a 2 kV voltage is applied across 4 mm gap between the neural probe and a grounded target to match the design parameters of FIG. 16. Electrospray formation is video-recorded in either fluorescence imaging mode and/or detecting the intensity distribution of laser light scattered by the spray plumes.

Figure 18:
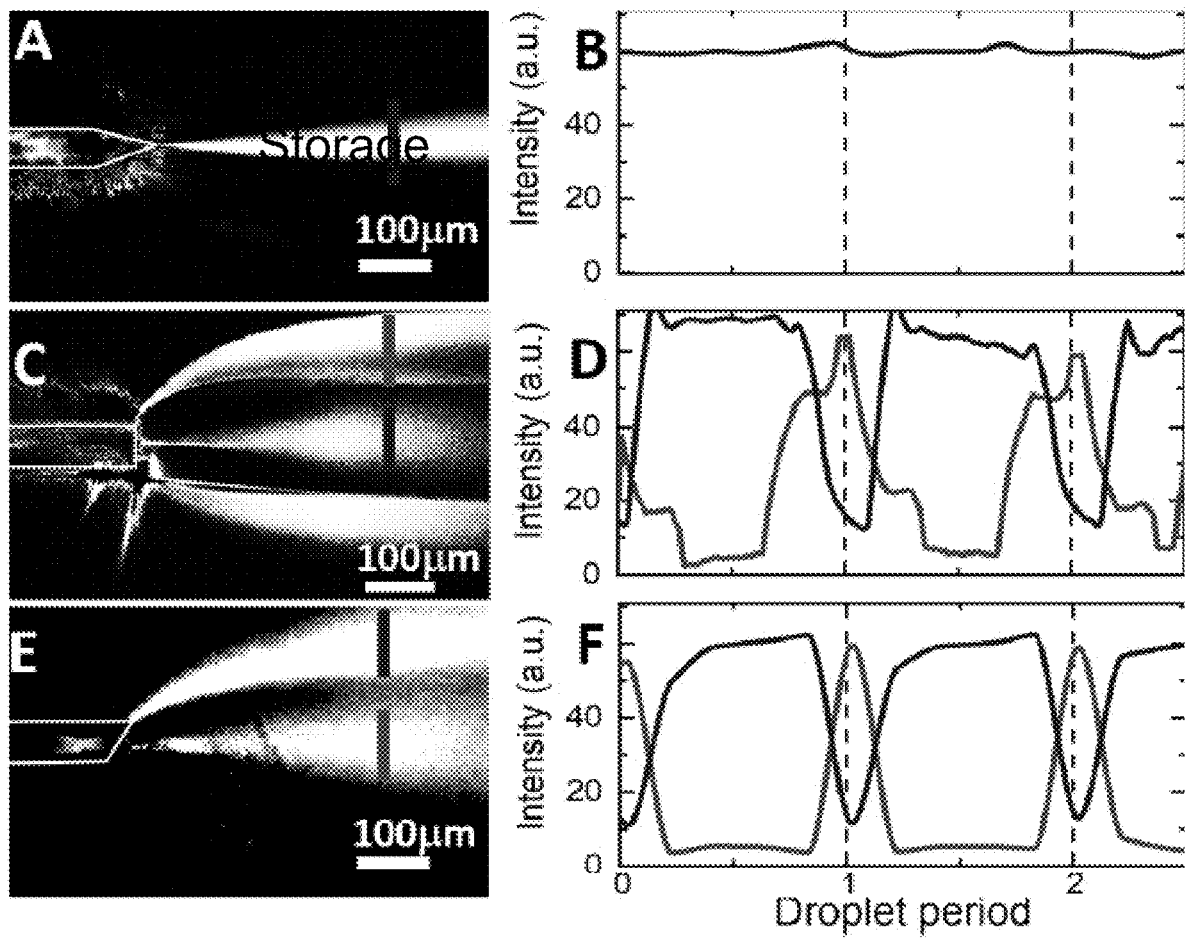
FIG. 18: Frame-averaged microscope images of the electrospray plumes for different tip designs (A, C, E), and corresponding temporal traces of plume scattered light intensity during several periods of segmented flow spraying (B, D, F). Aqueous droplet appears at the orifice at the beginning of each period.

Results and Discussion: FIG. 18 (panels A, C, E) show frame-averaged microscope images taken from a recorded video of the sprayed plumes for all three designs. Sharpened tip design of FIG. 18 (panel A) generates a single focused plume for both oil and water phases. Time series of scattered light intensity (FIG. 18 panel B) measured frame-by-frame at the position shown by a blue bar in FIG. 18 (panel A) demonstrates stability of the plume over several periods of segmented flow electrospraying. In contrast, a flat tip design of FIG. 18 panel C shows three separate plumes appearing at the edges and at the center of the nozzle. Time series of plumes intensity in FIG. 18 panel D demonstrates periodic switching between the edge plumes and the central plume with a period of the droplet-segmented flow. Close inspection of the video frames reveals that oil phase is sprayed at the edges, while aqueous plugs are sprayed in the central plume. This effect results from a significant difference in a threshold electric field strength for aqueous and oil phases that is needed for electrospraying. While aqueous phase with its low threshold can form a cone-jet electrospray at moment of ejection from a nozzle, oil phase with higher threshold can form a cone-jet only after spreading towards the "hot spots". This interpretation is validated by observation of two alternating switching cone-jets for angled nozzle tip design of FIG. 18 panel E. While outer edge plume is jetting at 45° when the oil plug is entering the nozzle, the aqueous phase is electrosprayed with a focused forward-directed plume.

This example demonstrates a silicon platform technology that enables on-chip integration of scaled microfluidic channels, miniaturized T-junction droplet generator, and an n-ESI emitter for efficient delivery of analytes to subsequent online mass spectrometry analysis. Engineering of emitter nozzle geometry allows to control location of electric field "hot spots" relative to the microfluidic channel outlet. This enables effective spatial and temporal separation of electrosprayed oil and aqueous phases of the segmented flow. Such phase separation is essential to avoid unwanted screening of targeted analyte ionization by oil phase, as well as interference of oil signals with analyte signals in a subsequent MS analysis. Droplet-by-droplet MS analysis with increased chemical sensitivity can enable detection of most important neurochemicals with high temporal resolution.

References for Example 5: [1] T. Ngernsutivorakul, et al., Anal. Chem. 90, 10943, 2018; [2] G. Petit-Pierre, et al., Nat. Commun. 8, 1239, 2017.

Figure 19A:
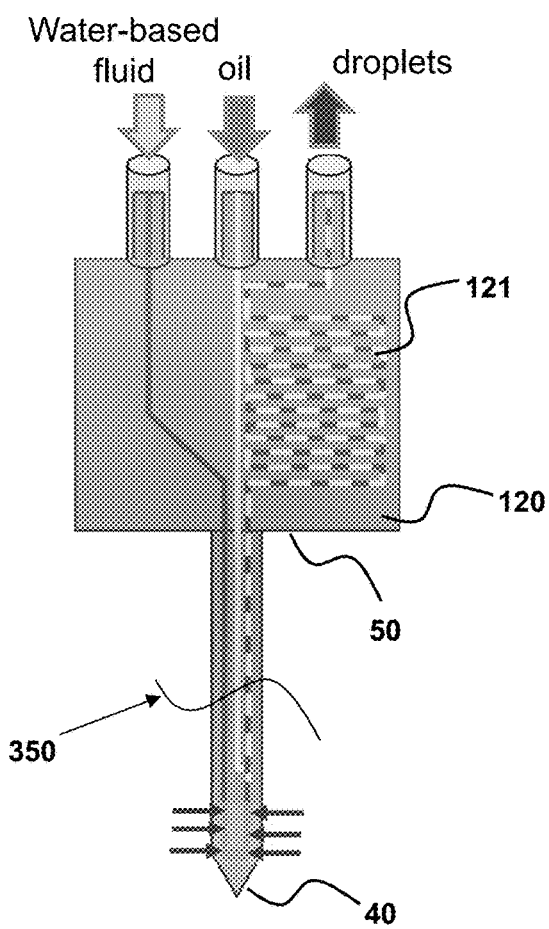
FIG. 19A illustrates a sampling configuration in a microdialysis embodiment. The arrows indicate direction of diffusion of an analyte in the biological fluid without fluid exchange. A fluid (e.g., aCSF) flows in the microfluidic channel toward an immiscible fluid (FC40) junction to from a train of fluid droplets containing analyte as indicated by the arrow for droplets.
Figure 19B:
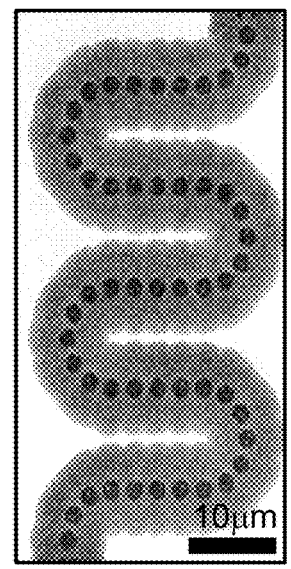
FIG. 19B is an SEM image of a portion of a serpentine channel for storage of the train of fluid droplets.
Figure 19C:
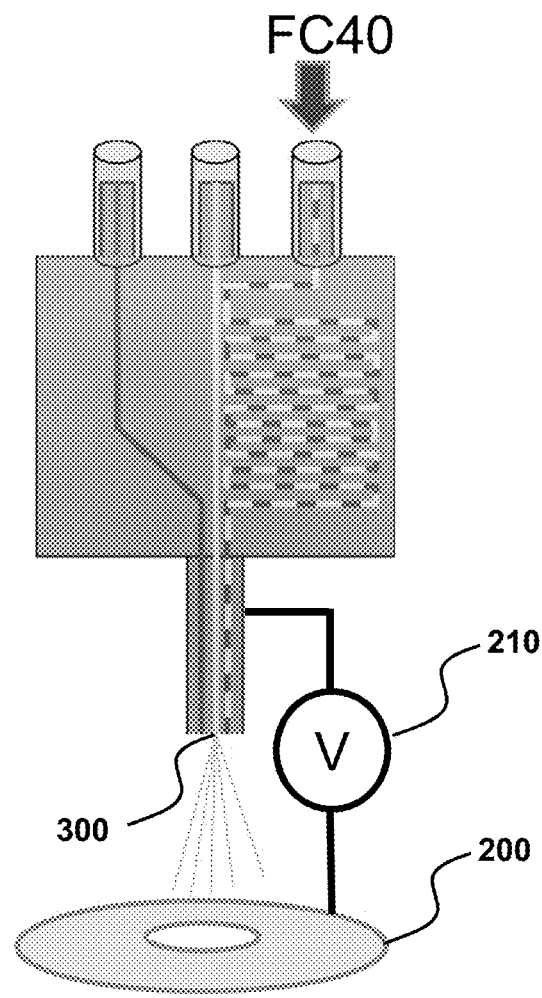
FIG. 19C illustrates fracture of the probe body fracture element to effectively form an ionization port for the analysis of the train of fluid droplets by, for example, MS.

Additional aspects of the systems and methods described herein are illustrated in FIGS. 19A-24. A fluid storage system 120 comprising a serpentine channel 121 is illustrated in FIG. 19A with an SEM illustrating formation of the serpentine channel in silicon provided in FIG. 19B. Referring to FIGS. 19A and 19C, an accessible location on the probe body (corresponding, in this example, to fracturable element 350) is positioned between the probe body distal tip end 40 and the proximal end 50, wherein an ionization port 300 is formed upon fracture for providing an ionized analyte to a mass spectrometer 200 (ESI-MS) by high-voltage source 210. The immiscible fluid may be an immiscible fluorocarbon oil, such as FC-40 (Fluorinert™ liquid FC-40).

Figure 20A:
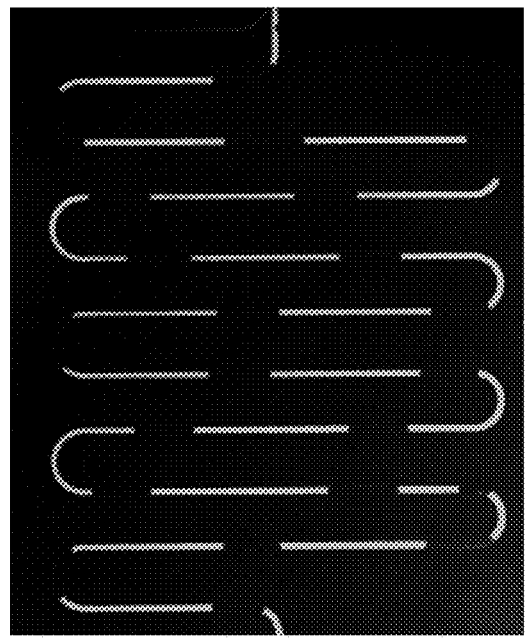
FIGS. 20A and 20B is a fluorescence micrograph of an integrated on-chip droplet storage device with 220 pL and 40 pL droplets, respectively, stored in a serpentine channel.
Figure 20B:
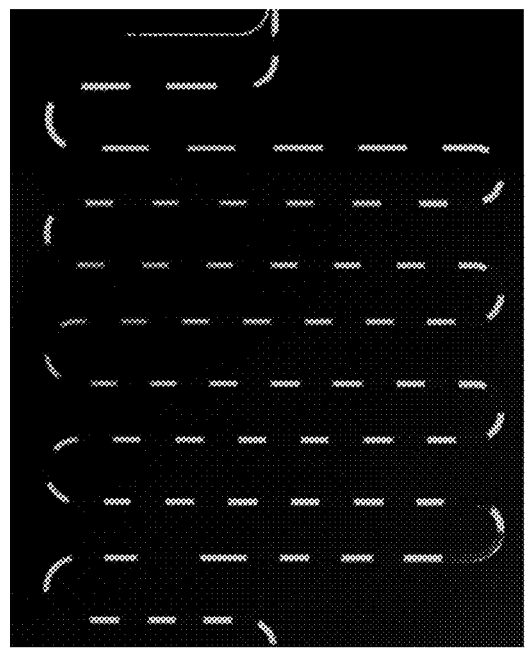

FIG. 20A-20B illustrates an exemplary fluid storage system comprising a serpentine microfluidic channel that can store 21 droplets of 200 pL (FIG. 20A) or 66 droplets of 40 pL each (FIG. 20B). Different droplet volumes are readily achieved by varying relative flow-rates at the immiscible fluid junction. After storing the droplets on-chip the droplets can be detected analyzed by optical microscopy, including fluorescence microscopy.

The fluid storage system may also be referred herein as a delay line with a given storage capacity. For example, the elongated serpentine structure microfluidic channel stores the oil droplet-water plug train. Changing the driving pressure of the connected pump (e.g., "flow-controller") controls flow and can stop the sampled droplet train and store them in the delay line. Since droplet generation frequency is highly controllable, each droplet represents a specific timestamp for the sampled analytes.

The total "recording time" of the delay line is governed by the total length of the delay line and the size of each droplet and plug between droplets. For example, if droplets are generated at a 1 Hz frequency, recording of 10 minutes of the chemical signal corresponds to 600 droplets.

Exemplary design parameters for the delay line include:

For a given channel cross-section, such as between 50 $\mu m^2$ and 150 $\mu m^2$ in the fabrication process described above, the maximum length is defined by the differential pressure that can be applied between the sampling site (membrane 118 of FIG. 1C or inlet 40 in FIG. 1A-1B) and outlet port 117.

With reasonable driving pressure of about 0 bar applied to the outlet port and keeping the inlet pressure close to intracranial pressure in the brain of 1 bar that produces differential pressure ($\Delta P$) of 1 bar.

For a given $\Delta P$ and flow rates (Q) (where Q=$\Delta P$/R, with R the hydrodynamic resistance of the channel, which increases with channel length and decrease in channel diameter) the number of droplets will be defined by their volume and frequency. For example, for a droplet volume of 1 pL in a channel with 5 $\mu m$ radius, the droplet linear length is about 20 $\mu m$. That will provide a storage of up to 2500 droplets in a 10 cm long channel that is folded (e.g., "serpentine") in a manner shown in FIG. 19B. Assuming that each droplet corresponds to 1 sec sampling time the droplet sequence corresponds to over 40 minutes of recording of the temporal profile of the chemical concentration.

Increasing the channel cross-section in the delay line region from 50 $\mu m^2$ to 2000 $\mu m^2$ will decrease the delay line hydrodynamic resistance, hence increasing the storage capacity for a given differential pressure. However, the minimal droplet size should also increase, to ensure that each droplet is plugging the whole cross-section of the channel.

Optimization of these parameters enables storage capacity between 1 minute to 20 hours of recording to be stored on the delay line with droplets varying between 1 pL and 50 pL.

Figure 21:
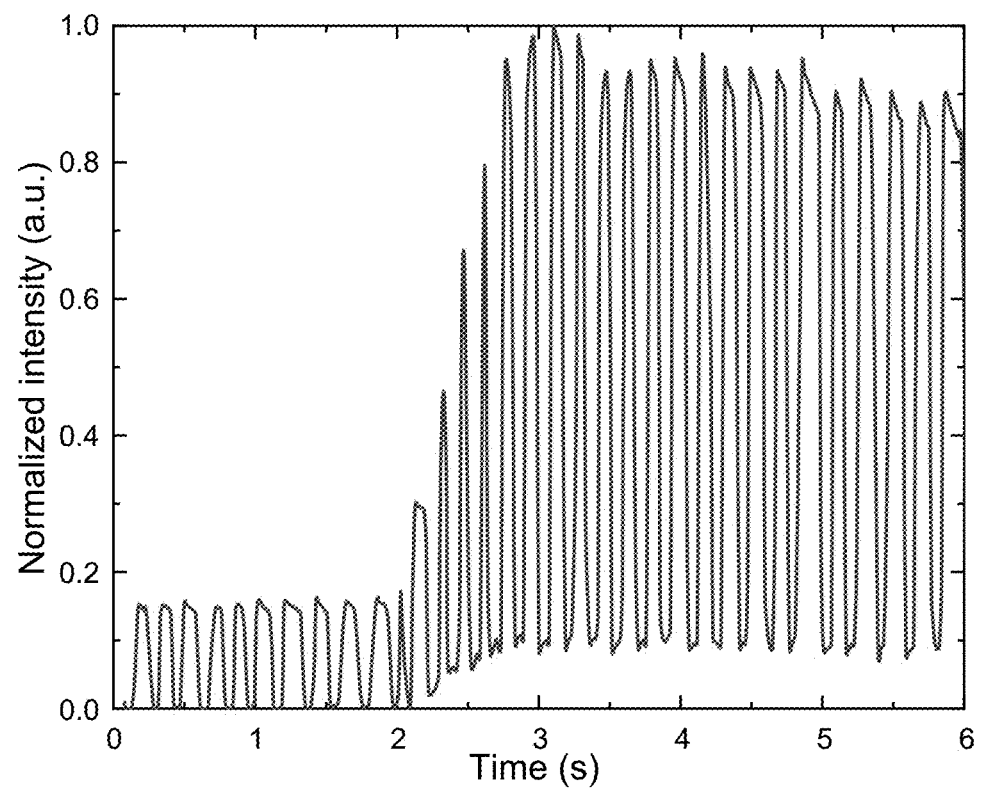
FIG. 21 illustrates droplet reading with reverse flow. Fluorescence intensity is measured on a droplet storage device when the flow is reversed. Time resolution is better than 1 s.

In addition, the silicon nitride cap layer in the fabrication process described above can withstand the differential pressure required for this application without breakage. Moreover, this cap layer is optically transparent. Accordingly, the probes and methods provided herein are compatible with a range of optical sensing techniques. Such optical detection can be used to measure chemical content of the droplets directly stored in the delay line. For example, fluorescence intensity can be used as a measure of the fluorescence dye concentration as shown in FIGS. 20A-20B and FIG. 21. Besides fluorescence, other optical methods can be used, for example Raman spectroscopy. This facilitates label-free detection.

Figure 22:
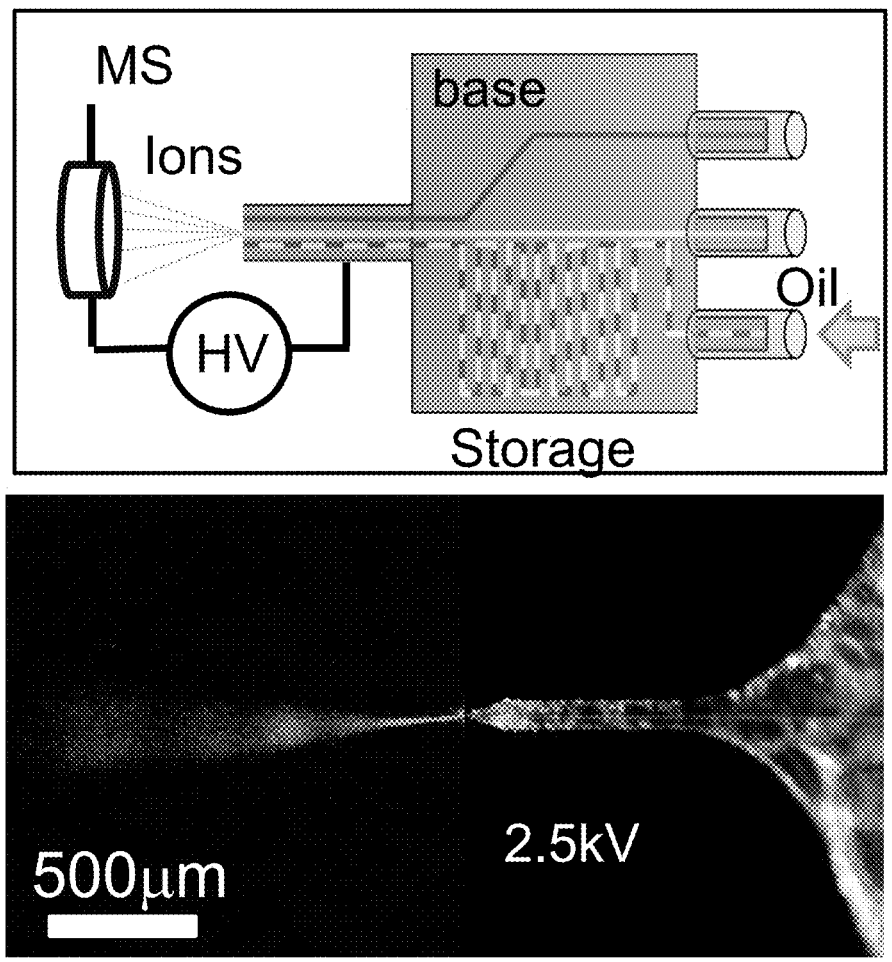
FIG. 22 illustrates direct infusion of ions into MS. The bottom panel illustrates an electrosprayed plume in front of a MS.
Figure 23:
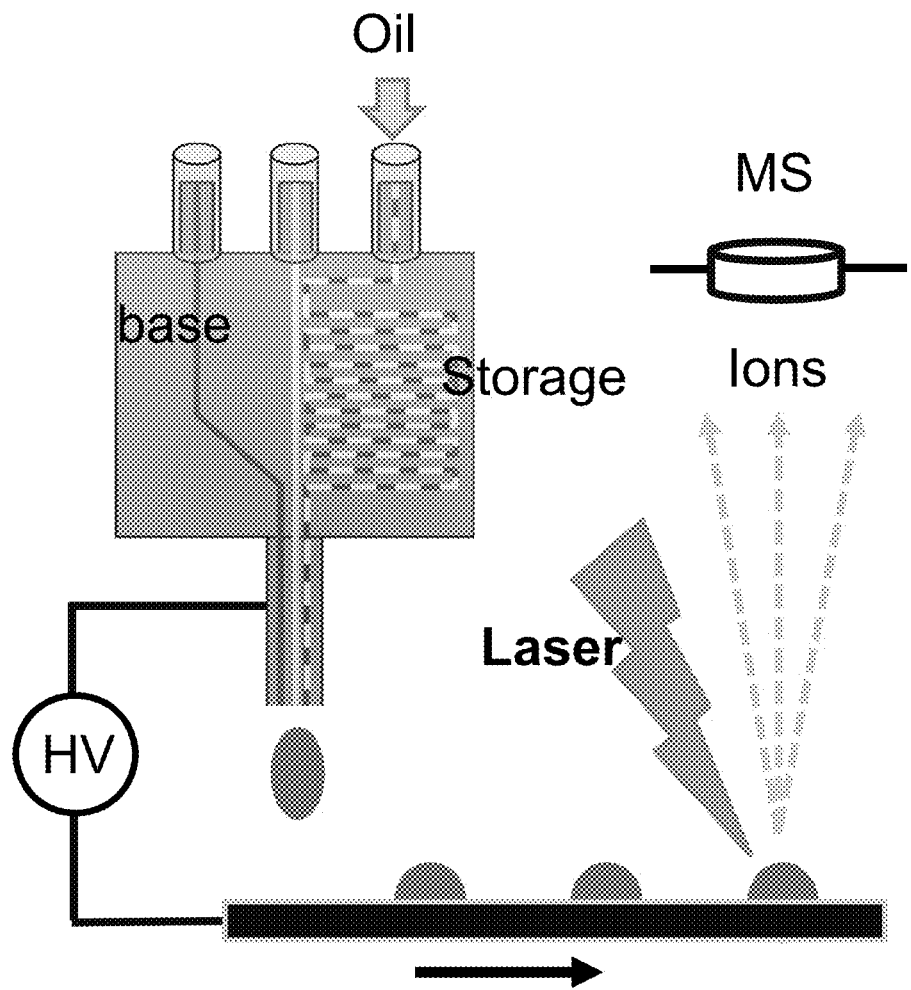
FIG. 23 illustrates deposition of droplets on a substrate. Droplet deposition on a substrate facilitates subsequent analysis using matrix-assisted laser desorption/ionization (MALDI).
Figure 24:
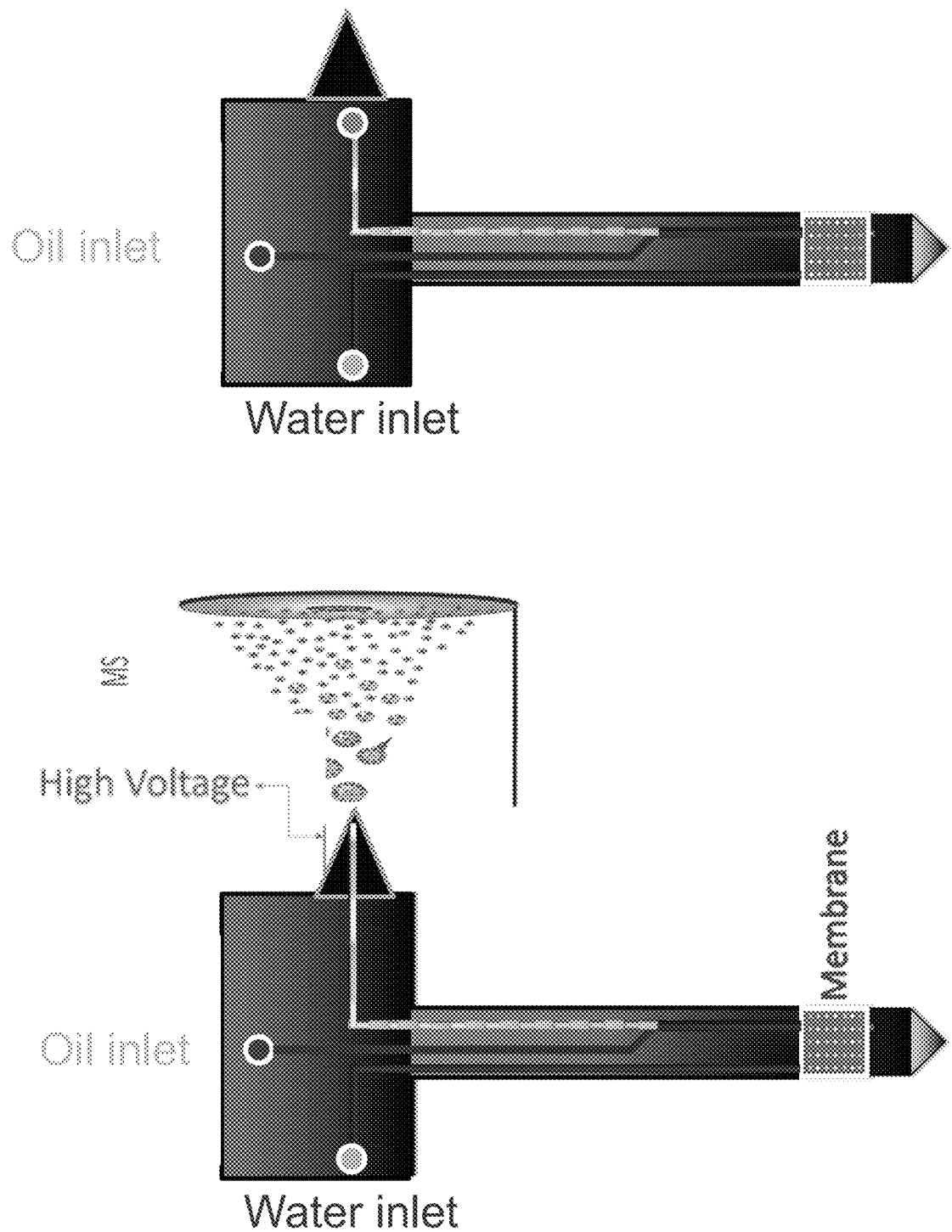
FIG. 24 illustrates collection of analyte for a probe having a membrane for microdialysis operation. The top panel illustrates collection. The bottom panel illustrates analysis with MS via application of a high voltage at the ionization port.

FIGS. 22-23 illustrate two examples of sample handling for MS analysis, depending on the type of MS analysis. FIG. 22 illustrates a direct infusion of ionized analytes into MS using electrospray ionization. FIG. 23 illustrates controlled electric-field assisted deposition of droplets on movable conductive substrate for subsequent matrix assisted laser desorption/ionization (MALDI) MS. Accordingly, the devices provided herein are compatible with both ESI-MS and MALDI-MS.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of components are intended to be exemplary, as it is known that one of ordinary skill in the art can name the same components differently.

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:
1. An implantable biomedical probe for sampling a biological fluid or an analyte of a biological fluid comprising:
   an integrated on-chip probe body having a distal tip end, a proximal end and a microfluidic channel extending between the distal tip end and the proximal end, wherein the microfluidic channel is embedded within a probe body cross-section configured for implantation into biological tissue with a cross-sectional area less than or equal to 10,000 $\mu m^2$;
   a microchannel opening at the distal tip end for providing the biological fluid or the analyte of the biological fluid to the microfluidic channel;
   an immiscible fluid microchannel that fluidically connects with the microfluidic channel to form a microfluidic junction for segmenting the biological fluid or the analyte of the biological fluid into a train of a sample-containing fluid, wherein adjacent sample-containing fluid segments from the microchannel opening are separated by an immiscible fluid configured to be introduced by the immiscible fluid microchannel;
   a fluid outlet positioned at the probe body proximal end and in fluidic contact with the microfluidic channel;
   a flow controller fluidically connected to the microfluidic channel and the immiscible fluid microchannel to control flow of the sample-containing fluid segments separated by the immiscible fluid in the microfluidic chan- nel and to collect the sample-containing fluid segments separated by the immiscible fluid in the microfluidic channel; and a fluid storage system for temporary storage of a train of the sample-containing fluid segments separated by the immiscible fluid, wherein the temporary storage maintains temporal collection of the biological fluid or the analyte of the biological fluid collected into the microfluidic channel;

wherein the integrated on-chip probe is configured to provide sampling, storage and sample emission or detection for the analyte of the biological fluid in a unitary material that forms the probe body.

2. The implantable biomedical probe of claim 1, wherein the fluid storage system comprises a serpentine channel having an effective channel length.

3. The implantable biomedical probe of claim 2, wherein the effective channel length is configured to provide a total collection time of the biological fluid or the analyte of the biological fluid up to 20 hours.

4. The implantable biomedical probe of claim 1, wherein the immiscible fluid comprises oil, the biological fluid is extracellular brain fluid and the analyte is a chemical in the extracellular brain fluid configured to enter the microfluidic channel by diffusion.

5. The implantable biomedical probe of claim 1, wherein each sample-containing fluid segment has a segment volume that is less than or equal to 50 pL.

6. The implantable biomedical probe of claim 1, wherein the microfluidic channel has an average diameter less than or equal to 50 µm.

7. The implantable biomedical probe of claim 1, further comprising a high-voltage source configured to electrically energize the probe body and to electrically eject and ionize the biological fluid from the fluid storage system.

8. The implantable biomedical probe of claim 7, having a sample collection mode and a sample analysis mode, wherein
the sample collection mode has a sample flow in a collection direction from the distal tip toward the proximal end; and
the sample analysis mode has a sample flow in an analysis direction opposite to the collection direction and from the proximal end toward the distal tip, and the distal tip end corresponds to a direct electrospray emitter configured to transfer the train of the sample-containing fluid segments into a mass spectrometer.

9. The implantable biomedical probe of claim 7, further comprising:
an ionization port in fluidic contact with the fluid storage system for ejection and ionization of the train of the sample-containing fluid segments.

10. The implantable biomedical probe of claim 9, wherein the ionization port is positioned at the probe body proximal end.

11. The implantable biomedical probe of claim 1, wherein the probe body or a portion thereof is formed from heavily-doped silicon.

12. The implantable biomedical probe of claim 1, further comprising a membrane in fluidic contact with the microfluidic channel for membrane dialysis.

13. The implantable biomedical probe of claim 1, wherein the sample emission comprises an ionization port for introduction of ions into a mass spectrometer and/or the sample detection comprises an optical detector configured to optically detect the analyte of the biological fluid in the fluid storage system.

14. The implantable biomedical probe of claim 1, configured to detect the analyte of the biological fluid at a concentration of less than or equal to 100 nM.

15. The implantable biomedical probe of claim 14, configured to detect two or more analytes in the biological fluid.

16. The implantable biomedical probe of claim 14, further comprising a mass spectrometer operably connected to an ESI emitter located on the probe body for analyte detection.

17. The implantable biomedical probe of claim 1, wherein the distal tip has a geometry and the microfluidic channel has a fluidic characteristic to provide a temporal resolution of 1 second or better and a spatial resolution of 100 µm or better.

18. The implantable biomedical probe of claim 1, wherein the unitary material comprises a silicon substrate, including a silicon-on-insulator (SOI) substrate.

19. The implantable biomedical probe of claim 1, further comprising an accessible element positioned between the probe body distal tip end and the proximal end, wherein an ionization port is formed upon access of the accessible element for providing an ionized analyte to a mass spectrometer.

20. A method of analyzing an analyte from a biological fluid, the method comprising the steps of:
implanting the implantable biomedical probe of claim 1 into a biological tissue;
collecting the analyte from the biological fluid in the microfluidic channel;
segmenting the collected analyte in a fluid sample in the microfluidic channel into a train of segmented analyte fluid samples having a sequence of segmented analyte fluid samples, with adjacent segmented analyte fluid samples separated by an immiscible fluid;
storing the train of segmented analyte fluid samples in the fluid storage system so that the sequence of segmented analyte fluid samples in the train is maintained;
electrically energizing the stored train of segmented analyte fluid samples to eject and/or ionize the analyte fluid sample from the fluid storage system and toward a mass spectrometer;
thereby analyzing the analyte in the biological fluid sample.

21. The method of claim 20, further comprising the steps of:
removing the implantable biomedical probe from the biological tissue; and
accessing an accessible location on the probe body at a location between the distal tip end and the proximal end to form an ionization port, wherein the step of electrically energizing ionizes the train of segmented analyte fluid samples that exits the implantable biomedical probe at the accessible location.

22. A method of making the implantable biomedical probe of claim 1, the method comprising the steps of making the integrated on-chip probe body by:
a) providing a silicon-on-insulator (SOI) wafer having a silicon device layer thickness less than or equal to 20 µm;
b) depositing a photoresist (PR) layer on top of the silicon device layer;
c) patterning the PR layer at a distal tip region of the probe body to define a locally doped region;
d) local doping of the silicon device layer to a sheet resistance that is less than or equal to 0.1 Ohm*cm;
e) stripping the PR layer;
f) depositing a mask layer formed of silicon oxide or silicon nitride on the silicon device layer surface;
g) depositing a PR layer on the mask layer;

h) patterning the PR layer on the mask layer with a series of round openings, the round openings having a diameter less than or equal to 1 μm, wherein the series of round openings are arranged in lines having a separation distance from adjacent lines less or equal to 10 μm to expose a mask pattern for formation of microfluidic interconnected channels;

i) etching the exposed mask pattern to expose a top surface of the silicon device layer;

j) etching the exposed pattern into the silicon device layer to a depth that is less than the silicon device layer thickness that enables adjacent holes in the silicon device layer to merge laterally into a microfluidic channel;

k) stripping the PR layer from the mask layer;

l) depositing a layer of silicon oxide or silicon nitride of less than or equal to 5 μm thickness to overgrow the round openings in the mask layer;

m) applying and patterning a PR on a top overgrown layer to define a device perimeter;

n) etching the top overgrown layer to expose a top silicon device layer;

o) etching the exposed silicon device layer to expose the SOI buried oxide layer (BOX);

p) stripping the PR on the top overgrown layer;

q) applying a PR to a backside handle silicon layer of the SOI;

r) patterning the PR on the backside handle silicon layer of the SOI to define a proximal end perimeter, a distal end perimeter, and an ionization port perimeter;

s) etching the backside handle to expose the BOX layer to isolate the proximal end perimeter, to undercut the distal end perimeter, and undercut the ionization port perimeter from the rest of the wafer;

t) stripping the PR on the backside SOI handle silicon layer to obtain the probe body supported on the wafer by bridges that connect the probe body to the wafer at the probe body corners; and u) releasing the probe body from the wafer by breaking the bridges at the probe body corners;

thereby making the integrated on-chip probe body of the implantable biomedical probe.

* * * * *